US007338965B2

(12) United States Patent
Moon et al.

(10) Patent No.: US 7,338,965 B2
(45) Date of Patent: Mar. 4, 2008

(54) 3,4-DISUBSTITUTED, 3,5-DISUBSTITUTED AND 3,4,5-SUBSTITUTED PIPERIDINES

(75) Inventors: Joseph B. Moon, Kalamazoo, MI (US); Shon R. Pulley, Hickory Corners, MI (US); Daniel H. Rich, Madison, WI (US); David L. Brown, Chesterfield, MO (US); Barbara Jagodzinska, Redwood City, CA (US); Varghese John, San Francisco, CA (US); John Jacobs, Kalamazoo, MI (US)

(73) Assignees: Pharmacia & Upjohn Company, Kalamazoo, MI (US); Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/299,746

(22) Filed: Nov. 19, 2002

(65) Prior Publication Data
US 2004/0034031 A1 Feb. 19, 2004

Related U.S. Application Data

(60) Provisional application No. 60/383,167, filed on May 24, 2002, provisional application No. 60/332,708, filed on Nov. 19, 2001.

(51) Int. Cl.
*A61K 31/445* (2006.01)
*C07D 211/42* (2006.01)

(52) U.S. Cl. .................. 514/327; 546/222; 546/217; 546/221

(58) Field of Classification Search ............... 546/222, 546/217, 221; 514/327
See application file for complete search history.

(56) References Cited

U.S. PATENT DOCUMENTS

| | | | | |
|---|---|---|---|---|
| 3,992,441 | A * | 11/1976 | Helland | ........................ 562/430 |
| 4,248,876 | A | 2/1981 | White | ........................ 514/327 |
| 4,745,122 | A | 5/1988 | Lassen | ........................ 514/321 |
| 4,997,836 | A * | 3/1991 | Sugihara et al. | ........ 514/252.13 |
| 5,142,056 | A | 8/1992 | Kempe et al. | |
| 5,475,138 | A | 12/1995 | Pal et al. | |
| 5,631,405 | A | 5/1997 | Pal et al. | |
| 5,708,004 | A | 1/1998 | Talley et al. | |
| 6,060,476 | A | 5/2000 | Vazquez et al. | |
| 6,136,824 | A | 10/2000 | MacLeod et al. | |
| 6,610,711 | B2 * | 8/2003 | Armer et al. | ................ 514/331 |

FOREIGN PATENT DOCUMENTS

| | | | |
|---|---|---|---|
| DE | 3640475 | * | 6/1988 |
| EP | 0 296 721 | | 12/1988 |
| EP | 0 316 718 A2 | | 5/1989 |
| EP | 0 979 819 A1 | | 2/2000 |
| WO | 97/09311 | | 3/1997 |
| WO | WO 97/09311 | * | 3/1997 |
| WO | 98/33795 | | 8/1998 |
| WO | 99/12532 | | 3/1999 |
| WO | WO 99/37651 A1 | * | 7/1999 |
| WO | WO 9959971 A1 | * | 11/1999 |
| WO | WO 00/02859 A1 | * | 1/2000 |
| WO | 00/20390 | | 4/2000 |
| WO | 02/066469 A2 | | 8/2002 |
| WO | 02/076440 A2 | | 10/2002 |
| WO | 02/088101 A2 | | 11/2002 |

OTHER PUBLICATIONS

Kamilova, A.Y. and Wolfe, M.S., Ann. Reports Med. Chem., vol. 38, 2003, pp. 41-50.*
Morgan, T.E. and G.A. Krafft, Ann. Reports Med. Chem., vol. 37, 2002, pp. 31-40.*
Olson, Richard E. et al, Ann. Reports Med. Chem., vol. 35, 2000, pp. 31-40.*
TCI America "Organic Chemicals Catalog 2002-2003", p. 971.*
International Search Report from corresponding International Patent Application PCT/US02/37037.
Bursavich, et al., "Solid-Phase Synthesis of Aspartic Peptidase Inhibitors: 3-Alkoxy-4-Aryl Piperidines," *Organic Letters*, vol. 3, 17:2625-2628 (2001).
Vieira, et al., "Substituted Piperidines-Highly Potent Renin Inhibitors Due to Induced Fit Adaptation of the Active Site," *Bioorganic & Medicinal Chemistry Letters*, 9:1397-1402 (1999).

(Continued)

*Primary Examiner*—Rita Desai
(74) *Attorney, Agent, or Firm*—McDonnell Boehnen Hulbert & Berghoff LLP

(57) ABSTRACT

The invention relates to substituted piperidine, piperazine, morpholine and thiomorpholine compounds useful in the treatment of Alzheimer's disease and more specifically to compounds that are capable of inhibiting beta-secretase, an enzyme that cleaves amyloid precursor protein to produce amyloid beta peptide (A-beta), a major component of the amyloid plaques found in the brains of Alzheimer's sufferers. One embodiment of the invention relates to compounds having the structure:

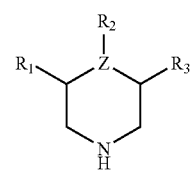

where Z is CR or N, and $R_1$, $R_2$ and $R_3$ are as described in the specification.

10 Claims, No Drawings

OTHER PUBLICATIONS

Bursavich, et al., "From Peptides to Non-Peptide Peptidomimetics: Design and Synthesis of New Piperidine Inhibitors of Aspartic Peptidases," *Organic Letters*, 3, 15:2317-2320 (2001).

Oefner, et al., "Renin Inhibition by Substituted Piperidines: A Novel Paradigm for the Inhibition of Monomeric Aspartic Proteinases," *Chemistry & Biology*, 6:127-131 (1999).

McErlane, et al., "Stereochemistry of 3-Methyl-4-phenylpiperidines Derived from Corresponding 4-Phenyl-4-piperidinols," *Canadian Journal of Chemistry*, 50:2149-2151 (1972).

Rogers, et al., "The Most Interesting members of the AH5183 Family of Drugs," *Cellular and Molecular Basis of Cholinergic Function*, 333-337 (1987).

Ghosh, et al., "Potent HIV-Protease Inhibitors: The Development of Tetrahydrofuranylgylicines as Novel P2-Ligands and Pyrazine Amides as P3-Ligands" *J. Med. Chem.* 36:2300-2310 (1993).

\* cited by examiner

SEQUENCE LISTING

<160> NUMBER OF SEQ ID NOS: 9

<210> SEQ ID NO 1
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green -continued

```
<400> SEQUENCE: 1

Ser Glu Val Asn Leu Asp Ala Glu Phe Arg Cys Lys Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 34
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
            20                  25                  30

Lys Lys

<210> SEQ ID NO 5
```

```
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial Sequence
```

-continued

```
<220> FEATURE:
<223> OTHER INFORMATION: synthetic peptide

<400> SEQUENCE: 8

Ser Glu Val Asn Leu Asp Ala Glu Phe
1               5

<210> SEQ ID NO 9
<211> LENGTH: 30
<212> TYPE: PRT
<213> ORGANISM: Artificial Sequence
<220> FEATURE:
<223> OTHER INFORMATION: synthetic peptide

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30
```

3,4-DISUBSTITUTED, 3,5-DISUBSTITUTED AND 3,4,5-SUBSTITUTED PIPERIDINES

BACKGROUND OF THE INVENTION

1. Field of the Invention

The invention relates to substituted piperidine and piperazine compounds useful in the treatment of Alzheimer's disease and more specifically to compounds that are capable of inhibiting beta-secretase, an enzyme that cleaves amyloid precursor protein to produce amyloid beta peptide (A-beta), a major component of the amyloid plaques found in the brains of Alzheimer's sufferers.

2. Description of Related Art

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years. Alzheimer's disease is characterized by two major pathologic observations in the brain: neurofibrillary tangles and beta amyloid (or neuritic) plaques, comprised predominantly of an aggregate of a peptide fragment know as A-beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A-beta in areas of the brain responsible for cognitive activities is a major factor in the development of AD. Beta-amyloid plaques are predominantly composed of amyloid beta peptide (A-beta, also sometimes designated betaA4). A-beta peptide is derived by proteolysis of the amyloid precursor protein (APP) and is comprised of 39-42 amino acids. Several proteases called secretases are involved in the processing of APP.

Cleavage of APP at the N-terminus of the A-beta peptide by beta-secretase and at the C-terminus by the gamma-secretase complex constitutes the beta-amyloidogenic pathway, i.e. the pathway by which A-beta is formed. Cleavage of APP by alpha-secretase produces alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sindha et al., 1999, *Nature* 402:537-554 (p501) and published PCT application WO00/17369.

Several lines of evidence indicate that progressive cerebral deposition of beta-amyloid peptide (A-beta) plays a seminal role in the pathogenesis of AD and can precede cognitive symptoms by years or decades. See, for example, Selkoe, 1991, *Neuron* 6:487. Release of A-beta from neuronal cells grown in culture and the presence of A-beta in cerebrospinal fluid (CSF) of both normal individuals and AD patients has been demonstrated. See, for example, Seubert et al., 1992, *Nature* 359:325-327.

It has been proposed that A-beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A-beta production, and is thus a therapeutic target for the treatment of AD. See for example, Sabbagh, M., et al., 1997, *Alz. Dis. Rev.* 3, 1-19.

BACE1 knockout mice fail to produce A-beta, and present a normal phenotype. When crossed with transgenic mice that over express APP, the progeny show reduced amounts of A-beta in brain extracts as compared with control animals (Luo et al., 2001 *Nature Neuroscience* 4:231-232). This evidence further supports the proposal that inhibition of beta-secretase activity and reduction of A-beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A-beta production, and/or are effective to reduce amyloid beta deposits or plaques, are needed for the treatment and prevention of disease characterized by amyloid beta deposits or plaques, such as AD.

SUMMARY OF THE INVENTION

The invention encompasses the substituted piperidine and piperazine compounds of the formulas shown below, pharmaceutical compositions containing the compounds and methods employing such compounds or compositions in the treatment of Alzheimer's disease and more specifically compounds that are capable of inhibiting beta-secretase, an enzyme that cleaves amyloid precursor protein to produce A-beta peptide, a major component of the amyloid plaques found in the brains of Alzheimer's sufferers.

In one aspect, the invention provides compounds of the formula I:

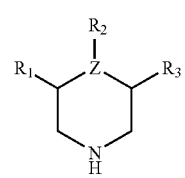

(I)

or a pharmaceutically acceptable salt or ester thereof,
wherein Z is CH or N;
wherein $R_1$ and $R_3$ are independently:

(I) $C_1$-$C_{10}$ alkyl, optionally substituted with one, two or three substituents independently selected from the group consisting of $C_1$-$C_3$ alkyl, —F, —Cl, —Br, —I, —OH, —SH, —C≡N, —CF$_3$, $C_1$-$C_3$ alkoxy, —O-phenyl, —NR$_{1-a}$R$_{1-b}$ where R$_{1-a}$ and R$_{1-b}$ are independently —H or $C_1$-$C_6$ alkyl, —OC═O NR$_{1-a}$R$_{1-b}$, —S(═O)$_2$ R$_{1-a}$, —NR$_{1-a}$C═O NR$_{1-a}$R$_{1-b}$, —C═O NR$_{1-a}$R$_{1-b}$, and —S(═O)$_2$ NR$_{1-a}$R$_{1-b}$, —(CH$_2$)$_{0-3}$— ($C_3$-$C_8$) cycloalkyl where cycloalkyl can be optionally substituted with one, two or three substituents selected from the group consisting of $C_1$-$C_3$ alkyl, —F, —Cl, —Br, —I, —OH, —SH, —C≡N, —CF$_3$, $C_1$-$C_6$ alkoxy, —O-phenyl, —CO—OH, —CO—O—($C_1$-$C_4$ alkyl), —NR$_{1-a}$R$_{1-b}$; $C_1$-$C_3$ alkoxy-(R$_{1-aryl}$), $C_1$-$C_3$ alkoxy-(R$_{1-heteroaryl}$), (II) —(CH$_2$)$_{n1}$—(R$_{1-aryl}$) where n$_1$ is zero or one and where R$_{1-aryl}$ is phenyl, 1-naphthyl, 2-naphthyl and indanyl, indenyl, dihydronaphthyl, tetralinyl optionally substituted with one, two, three or four of the following independently selected substituents on the aryl ring:

(1) $C_1$-$C_6$ alkyl optionally substituted with one, two or three substituents independently selected from the group consisting of $C_1$-$C_3$ alkyl, —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$(aryl-$C_{1-6}$ alkyl), —SO$_2$(heteroaryl-$C_{1-6}$ alkyl), —NR$_{1-a}$R$_{1-b}$, —C≡N, —CF$_3$, $C_1$-$C_3$ alkoxy, $C_1$-$C_3$ alkoxy-(R$_{1-aryl}$), $C_1$-$C_3$ alkoxy-(R$_{1-heteroaryl}$), (2) $C_2$-$C_6$ alkenyl with one or two double bonds, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$(aryl-$C_{1-6}$ alkyl), —SO$_2$(heteroaryl-$C_{1-6}$ alkyl), —C≡N, —CF$_3$, $C_1$-$C_3$ alkoxy, —NR$_{1-a}$R$_{1-b}$, $C_1$-$C_3$ alkoxy-(R$_{1-aryl}$), $C_1$-$C_3$ alkoxy-(R$_{1-heteroaryl}$), (3) $C_2$-$C_6$ alkynyl with one or two triple bonds, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$(aryl-$C_{1-6}$ alkyl), —SO$_2$(heteroaryl-$C_{1-6}$ alkyl), —C≡N, —CF$_3$, $C_1$-$C_3$ alkoxy, —NR$_{1-a}$R$_{1-b}$, $C_1$-$C_3$ alkoxy-(R$_{1-aryl}$), $C_1$-$C_3$ alkoxy-(R$_{1-heteroaryl}$), (4) —F, Cl, —Br and —I, (5) —$C_1$-$C_6$ alkoxy optionally substituted with one, two or three —F, (6) —NR$_{N-2}$R$_{N-3}$ where R$_{N-2}$ and R$_{N-3}$ are as defined below, (7) —OH, (8) —C≡N, (9) $C_3$-$C_7$ cycloalkyl, optionally substituted with one, two or three substituents selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$ (aryl-$C_{1-6}$ alkyl), —SO$_2$(heteroaryl-$C_{1-6}$ alkyl), —C≡N, —CF$_3$, $C_1$-$C_3$ alkoxy, —NR$_{1-a}$R$_{1-b}$, $C_1$-$C_3$ alkoxy-(R$_{1-aryl}$), $C_1$-$C_3$ alkoxy-(R$_{1-heteroaryl}$),

(10) —CO—($C_1$-$C_4$ alkyl),

(11) —SO$_2$—NR$_{1-a}$R$_{1-b}$,

(12) —CO—NR$_{1-a}$R$_{1-b}$,

(13) —SO$_2$—($C_1$-$C_4$ alkyl), (III) —(CH$_2$)$_{n1}$—(R$_{1-heteroaryl}$) where n$_1$ is as defined above and where R$_{1-heteroaryl}$ is selected from the group consisting of:

pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, where the R$_{1-heteroaryl}$ group is bonded to —(CH$_2$)$_{n1}$— by any ring atom of the parent R$_{1-heteroaryl}$ group substituted by hydrogen such that the new bond to the R$_{1-heteroaryl}$ group replaces the hydrogen atom and its bond, where heteroaryl is optionally substituted with one, two, three or four of:

(1) $C_1$-$C_6$ alkyl optionally substituted with one, two or three substituents independently selected from the group consisting of $C_1$-$C_3$ alkyl, —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$(aryl-$C_{1-6}$ alkyl), —SO$_2$(heteroaryl-$C_{1-6}$ alkyl), —NR$_{1-a}$R$_{1-b}$, —C≡N, —CF$_3$, $C_1$-$C_3$ alkoxy, $C_1$-$C_3$ alkoxy-(R$_{1-aryl}$), $C_1$-$C_3$ alkoxy-(R$_{1-heteroaryl}$), (2) $C_2$-$C_6$ alkenyl with one or two double bonds, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —SO$_2$($C_{1-6}$ alkyl), —SO$_2$(aryl-$C_{1-6}$ alkyl), —SO$_2$(heteroaryl- $C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$), (3) $C_2$-$C_6$ alkynyl with one or two triple bonds, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$), (4) —F, —Cl, —Br and —I, (5) —$C_1$-$C_6$ alkoxy optionally substituted with one, two, or three —F, (6) —$NR_{N-2}R_{N-3}$, (7) —OH, (8) —C≡N, (9) $C_3$-$C_7$ cycloalkyl, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$),

(10) —CO—($C_1$-$C_4$ alkyl),

(11) —$SO_2$—$NR_{1-a}R_{1-b}$,

(12) —CO—$NR_{1-a}R_{1-b}$,

(13) —$SO_2$—($C_1$-$C_4$ alkyl), with the proviso that when $n_1$ is zero, $R_{1-heteroaryl}$ is not bonded to the carbon chain by nitrogen, (IV) —$(CH_2)_{n1}$—($R_{1-heterocycle}$) where n, is as defined above and $R_{1-heterocycle}$ is selected from the group consisting of:

morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl dihydropyrazinyl dihydropyridinyl dihydropyrimidinyl, dihydrofuryl, dihydropyranyl, tetrahydrothienyl S-oxide, tetrahydrothienyl S,S-dioxide, homothiomorpholinyl S-oxide, where the $R_{1-heterocycle}$ group is bonded by any atom of the parent $R_{1-heterocycle}$ group substituted by hydrogen such that the new bond to the $R_{1-heterocycle}$ group replaces the hydrogen atom and its bond, where heterocycle is optionally substituted with one, two, three or four:

(1) $C_1$-$C_6$ alkyl optionally substituted with one, two or three substituents independently selected from the group consisting of $C_1$-$C_3$ alkyl, —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —$NR_{1-a}R_{1-b}$, —C≡N, —$CF_3$, $C_1$-$C_3$ alkoxy, $C_1$-$C_3$ alkoxy-($R_{1-aryl}$), $C_1$-$C_3$ alkoxy-($R_1$-heteroaryl), (2) $C_2$-$C_6$ alkenyl with one or two double bonds, optionally substituted with one, two or three substituents independently selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$), (3) $C_2$-$C_6$ alkynyl with one or two triple bonds, optionally substituted with one, two or three substituents independently selected from the group consisting of —F, —Cl, —Br, —I, —OH—SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$), (4) —F, —Cl, —Br and —I, (5) —$C_1$-$C_6$ alkoxy optionally substituted with one, two, or three —F, (6) —$NR_{N-2}R_{N-3}$, (7) —OH, (8) —C≡N, (9) $C_3$-$C_7$ cycloalkyl, optionally substituted with one, two or three substituents selected from the group consisting of —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$),

(10) —CO—($C_1$-$C_4$ alkyl),

(11) —$SO_2$—$NR_{1-a}R_{1-b}$,

(12) —CO—$NR_{1-a}R_{1-b}$,

(13) —$SO_2$—($C_1$-$C_4$ alkyl),

(14) ═O, with the proviso that when n, is zero $R_{1-heterocycle}$ is not bonded to the carbon chain by nitrogen;

(V) —H;

(VI) $R_{N-1}$—$X_N$— where $X_N$ is selected from the group consisting of:

(A) —CO—, (B) —$SO_2$— where $R_{N-1}$ is selected from the group consisting of:

(A) $R_{N-aryl}$ where $R_{N-aryl}$ is phenyl, 1-naphthyl, 2-naphthyl, tetralinyl, indanyl, dihydronaphthyl or 6,7,8,9-tetrahydro-5H-benzo[a]cycloheptenyl, optionally substituted with one, two or three of the following substituents which can be the same or different and are:

(1) $C_1$-$C_6$ alkyl, optionally substituted with one, two or three substituents selected from the group consisting of $C_1$-$C_3$ alkyl, —F, —Cl, —Br, —I, —OH, —SH, —S($C_{1-6}$ alkyl), —S(aryl-$C_{1-6}$ alkyl), —S(heteroaryl-$C_{1-6}$ alkyl), —S═O($C_{1-6}$ alkyl), —S═O(aryl-$C_{1-6}$ alkyl), —S═O(heteroaryl-$C_{1-6}$ alkyl), —$SO_2$($C_{1-6}$ alkyl), —$SO_2$(aryl-$C_{1-6}$ alkyl), —$SO_2$(heteroaryl-$C_{1-6}$ alkyl), —C≡N, —$CF_3$, $C_1$-$C_3$ alkoxy, —$NR_{1-a}R_{1-b}$, $C_1$-$C_3$ alkoxy-($R_{1-aryl}$), $C_1$-$C_3$ alkoxy-($R_{1-heteroaryl}$), (2) —OH, (3) —$NO_2$, (4) —F, —Cl, —Br, —I, (5) —CO—OH, (6) —C≡N,
(7) —(CH$_2$)$_{0-4}$—CO—NR$_{N-2}$R$_{N-3}$ where R$_{N-2}$ and R$_{N-3}$ are the same or different and are selected from the group consisting of:
  (a) —H,
  (b) —C$_1$-C$_6$ alkyl optionally substituted with one substitutent selected from the group consisting of:
    (i) —OH,
    (ii) —NH$_2$,
  (c) —C$_1$-C$_6$ alkyl optionally substituted with one to three groups independently selected from —F, —Cl, —Br, and —I,
  (d) —C$_3$-C$_7$ cycloalkyl,
  (e) —(C$_1$-C$_2$ alkyl)-(C$_3$-C$_7$ cycloalkyl),
  (f) —(C$_1$-C$_6$ alkyl)-O—(C$_1$-C$_3$ alkyl),
  (g) —C$_2$-C$_6$ alkenyl with one or two double bonds,
  (h) —C$_2$-C$_6$ alkynyl with one or two triple bonds,
  (i) —C$_1$-C$_6$ hydrocarbyl chain with one double bond and one triple bond,
  (j) —R$_{1-aryl}$,
  (k) —R$_{1-heteroaryl}$,
(8) —(CH$_2$)$_{0-4}$—CO—(C$_1$-C$_{12}$ alkyl),
(9) —(CH$_2$)$_{0-4}$—CO—(C$_2$-C$_{12}$ alkenyl with one, two or three double bonds),
(10) —(CH$_2$)$_{0-4}$—CO—(C$_2$-C$_{12}$ alkynyl with one, two or three triple bonds),
(11) —(CH$_2$)$_{0-4}$—CO— (C$_3$-C$_7$ cycloalkyl),
(12) —(CH$_2$)$_{0-4}$—CO—R$_{1-aryl}$,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of C$_1$-C$_6$ alkyl,
(16) —(CH$_2$)$_{0-4}$—CO—O—R$_{N-5}$ where R$_{N-5}$ is selected from the group consisting of:
  (a) C$_1$-C$_6$ alkyl,
  (b) —(CH$_2$)$_{0-2}$—(R$_{1-aryl}$),
  (c) C$_2$-C$_6$ alkenyl containing one or two double bonds,
  (d) C$_2$-C$_6$ alkynyl containing one or two triple bonds,
  (e) C$_3$-C$_7$ cycloalkyl,
  (f) —(CH$_2$)$_{0-2}$—(R$_{1-heteroaryl}$),
(17) —(CH$_2$)$_{0-4}$—SO$_2$—NR$_{N-2}$R$_{N-3}$,
(18) —(CH$_2$)$_{0-4}$—SO—(C$_1$-C$_8$ alkyl),
(19) —(CH$_2$)$_{0-4}$—SO$_2$ (C$_1$-C$_{12}$ alkyl),
(20) —(CH$_2$)$_{0-4}$—SO$_2$-(C$_3$-C$_7$ cycloalkyl),
(21) —(CH$_2$)$_{0-4}$—N(H or R$_{N-5}$)—CO—O—R$_{N-5}$ where R$_{N-5}$ can be the same or different,
(22) —(CH$_2$)$_{0-4}$—N(H or R$_{N-5}$)—CO—N(R$_{N-5}$)$_2$, where each R$_{N-5}$ is independently defined herein,
(23) —(CH$_2$)$_{0-4}$—N—CS—N(R$_{N-5}$)$_2$, where each R$_{N-5}$ is independently defined herein,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$-C$_6$ alkyl),
(28) —(CH$_2$)$_{0-4}$—O—P(O)—(OR$_{N-1}$)$_2$ where R$_{N-1}$ is —H or C$_1$-C$_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$)$_2$,
(32) —(CH$_2$)$_{0-4}$—O—(R$_{N-5}$)$_2$—COOH,
(33) —(CH$_2$)$_{0-4}$—S—(R$_{N-5}$)$_2$,
(34) —(CH$_2$)$_{0-4}$—O—(C$_1$-C$_6$ alkyl optionally substituted with one, two, three, four, or five of —F),
(35) C$_3$-C$_7$ cycloalkyl,
(36) C$_2$-C$_6$ alkenyl having one or two double bonds and which is optionally substituted with C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_3$ alkoxy, —NR$_{1-a}$R$_{1-b}$, C$_1$-C$_3$ alkoxy-(R$_{1-aryl}$), C$_1$-C$_3$ alkoxy-(R$_{1-heteroaryl}$),
(37) C$_2$-C$_6$ alkynyl with one or two triple bonds optionally substituted with C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_3$ alkoxy, —NR$_{1-a}$R$_{1-b}$, C$_1$-C$_3$ alkoxy-(R$_{1-aryl}$), C$_1$-C$_3$ alkoxy-(R$_{1-heteroaryl}$),
(38) —(CH$_2$)$_{0-4}$—N(—H or R$_{N-5}$)—SO$_2$—R$_{N-2}$, or
(39) —(CH$_2$)$_{0-4}$—C$_3$-C$_7$ cycloalkyl,
(B) —R$_{N-heteroaryl}$ where R$_{N-heteroaryl}$ carries the same definition as R$_{1-heteroaryl}$, where the R$_{N-heteroaryl}$ group is bonded by any atom of the parent R$_{N-heteroaryl}$ group substituted by hydrogen such that the new bond to the R$_{N-heteroaryl}$ group replaces the hydrogen atom and its bond, where heteroaryl is optionally substituted with one, two, three, or four groups independently selected from:
(1) C$_1$-C$_6$ alkyl, optionally substituted with one, two or three substituents selected from the group consisting of C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_3$ alkoxy, and —NR$_{1-a}$R$_{1-b}$, C$_1$-C$_3$ alkoxy-(R$_{1-aryl}$) C$_1$-C$_3$ alkoxy-(R$_{1-heteroaryl}$),
(2) —OH,
(3) —NO$_2$,
(4) —F, —Cl, —Br, —I,
(5) —CO—OH,
(6) —C≡N,
(7) —(CH$_2$)$_{0-4}$—CO—NR$_{N-2}$R$_{N-3}$,
(C) R$_{N-aryl}$—W—R$_{N-aryl}$,
(D) R$_{N-aryl}$—W—R$_{N-heteroaryl}$,
(E) R$_{N-aryl}$—W—R$_{N-heterocycle}$, where R$_{N-heterocycle}$ is the same as R$_{N-heterocycle}$,
(F) R$_{N-heteroaryl}$—W—R$_{N-aryl}$,
(G) R$_{N-heteroaryl}$—W—R$_{N-heteroaryl}$,
(H) R$_{N-heteroaryl}$—W—R$_{N-heterocycle}$,
(I) R$_{N-heterocycle}$—W—R$_{N-aryl}$,
(J) R$_{N-heterocycle}$—W—R$_{N-heteroaryl}$,
(K) R$_{N-heterocycle}$—W—R$_{N-heterocycle}$, and
where W is
(1) —(CH$_2$)$_{0-4}$—,
(2) —O—, (3) —S(O)$_{0-2}$—,
(4) —N(R$_{N-5}$)—, or
(5) —CO—;

(VII) —(CR$_{C-x}$R$_{C-y}$)$_{0-4}$R$_{C-aryl}$ where R$_{C-x}$ and R$_{C-y}$ are
—H,
C$_1$-C$_4$ alkyl optionally substituted with one or two —OH,
C$_1$-C$_4$ alkoxy optionally substituted with one, two, or three of
—F,
—(CH$_2$)$_{0-4}$—C$_3$-C$_7$ Cycloalkyl,
C$_2$-C$_6$ alkenyl containing one or two double bonds,
C$_2$-C$_6$ alkynyl containing one or two triple bonds,
phenyl, and where R$_{C-x}$ and R$_{C-y}$ are taken together with the carbon to which they are attached to form a carbocycle of three, four, five, six and seven carbon atoms, optionally where one carbon atom is replaced by a heteroatom selected from the group consisting of —O—, —S—, —SO$_2$—, —NR$_{N-2}$— and R$_{C-aryl}$ is the same as R$_{N-aryl}$;

(VIII) —(CR$_{C-x}$R$_{C-y}$)$_{0-4}$—R$_{C-aryl}$—R$_{C-aryl}$,
(IX) —(CR$_{C-x}$R$_{C-y}$)$_{0-4}$—R$_{C-aryl}$—R$_{C-heteroaryl}$,
(X) —(CR$_{C-x}$R$_{C-y}$)$_{0-4}$—R$_{C-heteroaryl}$—R$_{C-aryl}$,
(XI) —(CR$_{C-x}$R$_{C-y}$)-4—R$_{C-heteroaryl}$—R$_{C-heteroaryl}$),
(XII) —(CR$_{C-x}$R$_{C-y}$)$_{0-4}$—R$_{C-aryl}$—R$_{C-heterocycle}$ and R$_{C-heterocycle}$ is the same as R$_{N-heterocycle}$,
(XIII) —(CR$_{C-x}$R$_{C-y}$)$_{0-4}$—R$_{C-heteroaryl}$—R$_{C-heterocycle}$,
(XIV) —(CR$_{C-x}$R$_{C-y}$)$_{0-4}$—R$_{C-heterocycle}$—R$_{C-aryl}$,
(XV) —(CR$_{C-x}$R$_{C-y}$)$_{0-4}$—R$_{C-heterocycle}$—R$_{C-heteroaryl}$
(XVI) —(CR$_{C-x}$R$_{C-y}$)$_{0-4}$—R$_{C-heterocycle}$—R$_{C-heterocycle}$
(XVII) —[C(R$_{C-1}$) (R$_{C-2}$)]$_{1-3}$—CO—N—(R$_{C-3}$)$_2$ where R$_{C-1}$ and R$_{C-2}$ are the same or different and are selected from the group consisting of:
(A) —H,
(B) —C$_1$-C$_6$ alkyl, optionally substituted with one, two or three substituents selected from the group consisting of C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_6$ alkoxy, —O-phenyl, —NR$_{1-a}$R$_{1-b}$, C$_1$-C$_3$ alkoxy-(R$_{1-aryl}$), C$_1$-C$_3$ alkoxy-(R$_{1-heteroaryl}$),
(C) C$_2$-C$_6$ alkenyl with one or two double bonds, optionally substituted with one, two or three substituents selected from the group consisting of C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_6$ alkoxy, —O-phenyl, —NR$_{1-a}$R$_{1-b}$, C$_1$-C$_3$ alkoxy-(R$_{1-aryl}$), C$_1$-C$_3$ alkoxy-(R$_{1-heteroaryl}$),
(D) —(CH$_2$)$_{0-4}$—C$_3$-C$_7$ cycloalkyl, optionally substituted with one, two or three substituents selected from the group consisting of C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_6$ alkoxy, —O-phenyl, —NR$_{1-a}$R$_{1-b}$, C$_1$-C$_3$ alkoxy-(R$_{1-aryl}$), C$_1$-C$_3$ alkoxy-(R$_{1-heteroaryl}$),
(E) —(C$_1$-C$_4$ alkyl)-R$_{C'-aryl}$ where R$_{C'-aryl}$ is as defined for R$_{1-aryl}$,
(F) —(C$_1$-C$_4$ alkyl)-R$_{C-heteroaryl}$,
(G) —(C$_1$-C$_4$ alkyl)-R$_{C-heterocycle}$,
(H) —R$_{C-heteroaryl}$,
(I) —R$_{C-heterocycle}$, and
(J) —R$_{C'-aryl}$, and where R$_{C-3}$ is the same or different and is:
(A) —H,
(B) —C$_1$-C$_6$ alkyl optionally substituted with one, two or three substituents selected from the group consisting of C$_1$-C$_3$ alkyl, —F, —Cl, —Br, —I, —OH, —SH, —S(C$_{1-6}$ alkyl), —S(aryl-C$_{1-6}$ alkyl), —S(heteroaryl-C$_{1-6}$ alkyl), —S=O(C$_{1-6}$ alkyl), —S=O(aryl-C$_{1-6}$ alkyl), —S=O(heteroaryl-C$_{1-6}$ alkyl), —SO$_2$(C$_{1-6}$ alkyl), —SO$_2$(aryl-C$_{1-6}$ alkyl), —SO$_2$(heteroaryl-C$_{1-6}$ alkyl), —C≡N, —CF$_3$, C$_1$-C$_6$ alkoxy, —O-phenyl, and —NR$_{1-a}$R$_{1-b}$, C$_1$-C$_3$ alkoxy-(R$_{1-aryl}$), C$_1$-C$_3$ alkoxy-(R$_{1-heteroaryl}$),
(C) —(CH$_2$)$_{0-4}$—C$_3$-C$_7$ cycloalkyl,
(D) —(C$_1$-C$_4$ alkyl)-R$_{C'-aryl}$,
(E) —(C$_1$-C$_4$ alkyl)-R$_{C-heteroaryl}$, or
(F) —(C$_1$-C$_4$ alkyl)-R$_{C-heterocycle}$;
(XVIII) —(CH$_2$)$_o$-Q-(CH$_2$)$_p$—B, where o and p are independently integers of 1-4, Q is O, S, SO, SO$_2$, NR$_1$, and B is C$_{1-6}$ alkyl, aryl, heteroaryl, or heterocycle;
(XIX) —O—R$_9$, —S—R$_9$, —NH—R$_9$, or N(R$_9$)$_2$;
(XX) —OC(=O)—R$_9$
(XXI) —C(=O)O—R$_9$
(XXII) —N(R$_8$)C(=O) —R$_9$
(XXIII) —C(=O)N(R$_8$)—R$_9$
(XXIV) —SO$_2$N(R$_8$)C(=O) —R$_9$
(XXV) —C(=O)N(R$_8$)SO$_2$—R$_9$
(XXVI) —SO$_2$—R$_9$;

wherein R$_8$ is defined as H or C$_1$-C$_6$ alkyl optionally substituted with one to three groups independently selected from —OH, —NH$_2$, —F, —Cl, —Br, and —I;
wherein R$_9$ is defined as (I)-(XVIII) above
and wherein R$_2$ is is C$_1$ to C$_6$ alkyl, cyclohexyl, cyclopentyl, pyridinyl, phenyl, isoxazole, pyrazole, furan, thiophene, and other five and six membered heterocycles containing carbon, nitrogen, oxygen and sulfur, said C$_1$ to C$_6$ alkyl, cyclohexyl, cyclopentyl, pyridinyl, phenyl, furan, thiophene may be optionally substituted with one, two or three radicals selected from CF$_3$, OCF$_3$, hydroxyl, halo, C$_{1-2}$-alkyl, C$_{1-2}$-haloalkyl, cyano, carboxyl, C$_{1-2}$-alkoxycarbonyl, C$_{1-2}$-hydroxyalkyl, thioalkyl, aminosulfonyl, C$_{1-2}$-alkylaminosulfonyl, methyl C$_{1-2}$-haloalkoxy, amino, C$_{1-2}$-alkylamino, phenylamino, nitro, C$_{1-2}$-alkoxy-C$_{1-2}$-alkyl, C$_{1-2}$-alkylsulfinyl, C$_{1-2}$-alkoxy and C$_{1-3}$-alkylthio.

In another aspect of the invention, at least one of R$_1$, R$_2$ or R$_3$ is H; in a further embodiment, at least two of R$_1$, R$_2$ or R$_3$ is H.

The invention also includes a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula I.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease, such as those listed above.

In an embodiment, this method of treatment can prevent a disease, such as those listed above, from developing.

In an embodiment, this method of treatment can employ therapeutically effective amounts: for oral administration from about 0.1 mg/day to about 3,000, preferably about 1,000 mg/day; for parenteral, sublingual, intranasal, intrathecal administration from about 0.5 to about 500 mg/day, preferably about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The invention also includes a pharmaceutical composition which includes a compound of formula I or a pharmaceutically acceptable salt or ester thereof; and an inert diluent or edible carrier.

The invention also includes the use of a compound of formula I or a pharmaceutically acceptable salt or ester thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of formula (I) can be employed where the disease is Alzheimer's disease.

In an embodiment, this use of a compound of formula (I) can help prevent or delay the onset of Alzheimer's disease.

In an embodiment, this use of a compound of formula (I) can be employed where the disease is mild cognitive impairment.

In an embodiment, this use of a compound of formula (I) can be employed where the disease is Down's syndrome.

In an embodiment, this use of a compound of formula (I) can be employed where the disease is Hereditary Cerebral Hemorrhage with Amyloidosis of the Dutch-Type.

In an embodiment, this use of a compound of formula (I) can be employed where the disease is cerebral amyloid angiopathy.

In an embodiment, this use of a compound of formula (I) can be employed where the disease is degenerative dementias.

In an embodiment, this use of a compound of formula (I) can be employed where the disease is diffuse Lewy body type of Alzheimer's disease.

In an embodiment, this use of a compound of formula (I) employs a pharmaceutically acceptable salt selected from the group consisting of salts of the following acids hydrochloric, hydrobromic, hydroiodic, nitric, sulfuric, phosphoric, citric, methanesulfonic, $CH_3—(CH_2)_n—COOH$ where n is 0 thru 4, $HOOC—(CH_2)_n—COOH$ where n is as defined above, $HOOC—CH=CH—COOH$, and phenyl-COOH.

The invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of a compound of formula I or a pharmaceutically acceptable salt or ester thereof.

The invention also includes a method for inhibiting beta-secretase activity, including exposing said beta-secretase to an effective inhibitory amount of a compound of formula I or a pharmaceutically acceptable salt or ester thereof.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound of formula I or a pharmaceutically acceptable salt or ester thereof.

In an embodiment, this method employs a cleavage site: between Met652 and Asp653, numbered for the APP-751 isotype; between Met 671 and Asp 672, numbered for the APP-770 isotype; between Leu596 and Asp597 of the APP- 695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The invention also includes a method for inhibiting production of amyloid beta peptide (A beta) in a cell, including administering to said cell an effective inhibitory amount of a compound of formula I or a pharmaceutically acceptable salt or ester thereof.

In an embodiment, this method includes administering to an animal.

In an embodiment, this method includes administering to a human.

The invention also includes a method for inhibiting the production of beta-amyloid plaque in an animal, including administering to said animal an effective inhibitory amount of a compound of formula I or a pharmaceutically acceptable salt or ester thereof.

In an embodiment, this method includes administering to a human.

The invention also includes a method for treating or preventing a disease characterized by beta-amyloid deposits in the brain including administering to a patient an effective therapeutic amount of a compound of formula I or a pharmaceutically acceptable salt or ester thereof.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The invention also includes a composition including beta-secretase complexed with a compound of formula I or a pharmaceutically acceptable salt or ester thereof.

The invention also includes a method for producing a beta-secretase complex including exposing beta-secretase to a compound of formula I or a pharmaceutically acceptable salt or ester thereof, in a reaction mixture under conditions suitable for the production of said complex.

In an embodiment, this method employs exposing in vitro.

In an embodiment, this method employs a reaction mixture that is a cell.

The invention also includes a component kit including component parts capable of being assembled, in which at least one component part includes a compound of formula (I) enclosed in a container.

In an embodiment, this component kit includes lyophilized compound, and at least one further component part includes a diluent.

The invention also includes a container kit including a plurality of containers, each container including one or more unit dose of a compound of formula I or a pharmaceutically acceptable salt or ester thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The invention also includes an agent kit including a compound of formula I or a pharmaceutically acceptable salt or ester thereof; and one or more therapeutic agents selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The invention also includes a composition including: a compound of formula I or a pharmaceutically acceptable salt or ester thereof; and an inert diluent or edible carrier.

In an embodiment, this composition includes a carrier that is an oil.

The invention also includes a composition including: a compound of formula I or a pharmaceutically acceptable salt or ester thereof; and a binder, excipient, disintegrating agent, lubricant, or gildant.

The invention also includes a composition including: a compound of formula I or a pharmaceutically acceptable salt ester thereof; disposed in a cream, ointment, or patch.

The invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

The invention includes a method for treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment, comprising administering to such patient a therapeutically effective amount of a compound of formula (I), or a pharmaceutically acceptable salt or ester thereof, wherein Z, $R_1$, $R_2$ and $R_3$ are as defined above and below.

The invention further encompasses a method for making a compound of formula (I), or a pharmaceutically acceptable salt or ester thereof, wherein Z, $R_1$, $R_2$ and $R_3$ are as defined as above or below.

DETAILED DESCRIPTION OF THE INVENTION

The invention relates to compounds of formula I, or a pharmaceutically acceptable salt or ester thereof. The invention encompasses all steroisomers of formula I and of the other compounds disclosed herein.

Further in accordance with the embodiment of the invention described above, compounds of Formula I include those where $R_1$ and $R_3$ are independently:

(I) —$(CH_2)_{n1}$—($R_{1-aryl}$), where $n_1$ is zero or one and where $R_{1-aryl}$ is phenyl, 1-naphthyl, 2-naphthyl, indanyl, indenyl, dihydronaphthalyl, or tetralinyl optionally substituted with one, two, three, or four of the following substituents on the aryl ring:
  (A) $C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$, $C_1$-$C_3$ alkoxy-($R_{1-aryl}$), $C_1$-$C_3$ alkoxy-($R_{1-heteroaryl}$),
  (B) $C_2$-$C_6$ alkenyl with one or two double bonds, optionally substituted with one, two or three substituents selected from the group consisting of —F, —Cl, —Br, —I, —OH, —SH, —C≡N, —$CF_3$, $C_1$-$C_3$ alkoxy, and —$NR_{1-a}R_{1-b}$, $C_1$-$C_3$ alkoxy-($R_{1-aryl}$), $C_1$-$C_3$ alkoxy-($R_{1-heteroaryl}$),
  (C) $C_2$-$C_6$ alkynyl with one or two triple bonds, optionally substituted with one, two or three substituents selected from the group consisting of —F, —Cl, —Br, —I, —OH, —SH, —C≡N, —$CF_3$, $C_1$-$C_3$ alkoxy, and —$NR_{1-a}R_{1-b}$, $C_1$-$C_3$ alkoxy-($R_{1-aryl}$), $C_1$-$C_3$ alkoxy-($R_{1-heteroaryl}$),
  (D) —F, Cl, —Br, or —I,
  (E) —$C_1$-$C_6$ alkoxy optionally substituted with one, two, or three —F,
  (F) —$NR_{N-2}R_{N-3}$, where $R_{N-2}$ and $R_{N-3}$ are independently selected from the group consisting of:
    (1) —H,
    (2) —$C_1$-$C_6$ alkyl optionally substituted with one substituent selected from the group consisting of:
      (a) —OH, and
      (b) —$NH_2$,
    (3) —$C_1$-$C_6$ alkyl optionally substituted with one to three —F, —Cl, —Br, or —I,
    (4) —$C_3$-$C_7$ cycloalkyl,
    (5) —($C_1$-$C_2$ alkyl)—($C_3$-$C_7$ cycloalkyl),
    (6) —($C_1$-$C_6$ alkyl) —O—($C_1$-$C_3$ alkyl),
    (7) —$C_2$-$C_6$ alkenyl with one or two double bonds,
    (8) —$C_2$-$C_6$ alkynyl with one or two triple bonds,
    (9) —$C_1$-$C_6$ alkyl chain with one double bond and one triple bond,
    (10) —$R_{1-aryl}$, where $R_{1-aryl}$ is as defined above, and
    (11) —$R_{1-heteroaryl}$,
  (G) —OH,
  (H) —C≡N
  (I) $C_3$-$C_7$ cycloalkyl, optionally substituted with one, two or three substituents selected from the group consisting of —F, —Cl, —Br, —I, —OH, —SH, —C≡N, —$CF_3$, —$NR_{1-a}R_{1-b}$, $C_1$-$C_3$ alkoxy, $C_1$-$C_3$ alkoxy-($R_{1-aryl}$), $C_1$-$C_3$ alkoxy-($R_{1-heteroaryl}$),
  (K) —CO—($C_1$-$C_4$ alkyl),
  (L) —$SO_2$—$NR_{1-a}R_{1-b}$,
  (M) —CO—$NR_{1-a}R_{1-b}$, or
  (N) —$SO_2$—($C_1$-$C_4$ alkyl), or (II) —$(CH_2)_{n1}$—($R_{1-heteroaryl}$), where $n_1$ is zero or one and where $R_{1-heteroaryl}$ is selected from the group consisting of: pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl,
  where the $R_{1-heteroaryl}$ group is bonded to —$(CH_2)_{n1}$— by any ring atom of the parent $R_{1-heteroaryl}$ group substituted by hydrogen such that the new bond to the $R_{1-heteroaryl}$ group replaces the hydrogen atom and its bond, where heteroaryl is optionally substituted with one, two, three, or four of:
  (1) $C_1$-$C_6$ alkyl optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1-a}R_{1-b}$, $C_1$-$C_3$ alkoxy, $C_1$-$C_3$ alkoxy-($R_{1-aryl}$), $C_1$-$C_3$ alkoxy-($R_{1-heteroaryl}$),
  (2) $C_2$-$C_6$ alkenyl with one or two double bonds, optionally substituted with one, two or three substituents selected from the group consisting of —F, —Cl, —Br, —I, —OH, —SH, —CO—N, —$CF_3$, $C_1$-$C_3$ alkoxy, and —$NR_{1-a}R_{1-b}$, where $R_{1-a}$ and $R_{1-b}$ are —H or $C_1$-$C_6$ alkyl, $C_1$-$C_3$ alkoxy, $C_1$-$C_3$ alkoxy-($R_{1-aryl}$), $C_1$-$C_3$ alkoxy-($R_{1-heteroaryl}$),
  (3) $C_2$-$C_6$ alkynyl with one or two triple bonds, optionally substituted with one, two or three substituents selected from the group consisting of —F, —Cl, —Br, —I, —OH, —SH, —C≡N, —$CF_3$, $C_1$-$C_3$ alkoxy, and —$NR_{1-a}R_{1-b}$, where $R_{1-a}$ and $R_{1-b}$ are —H or $C_1$-$C_6$ alkyl, $C_1$-$C_3$ alkoxy, $C_1$-$C_3$ alkoxy-($R_{1-aryl}$), $C_1$-$C_3$ alkoxy-($R_{1-heteroaryl}$),
  (4) —F, Cl, —Br, or —I,
  (5) —$C_1$-$C_6$ alkoxy optionally substituted with one, two, or three —F,
  (6) —$NR_{N-2}R_{N-3}$,
  (7) —OH,
  (8) —C≡N,
  (9) $C_3$-$C_7$ cycloalkyl, optionally substituted with one, two or three substituents selected from the group consisting of —F, —Cl, —Br, —I, —OH, —SH, —C≡N, —$CF_3$, $C_1$-$C_3$ alkoxy, and —$NR_{1-a}R_{1-b}$, where $R_{1-a}$ and $R_{1-b}$ are —H or $C_1$-$C_6$ alkyl, $C_1$-$C_3$ alkoxy, $C_1$-$C_3$ alkoxy-($R_{1\text{-}aryl}$), $C_1$-$C_3$ alkoxy-($R_{1\text{-}heteroaryl}$),
- (10) —CO—($C_1$-$C_4$ alkyl),
- (11) —SO$_2$—NR$_{1\text{-}a}$R$_{1\text{-}b}$,
- (12) —CO—NR$_{1\text{-}a}$R$_{1\text{-}b}$, or
- (13) —SO$_2$—($C_1$-$C_4$ alkyl), with the proviso that when $n_t$ is zero $R_{1\text{-}heteroaryl}$ is not bonded to the carbon chain by nitrogen.

In another embodiment, $R_1$ and $R_3$ are independently:
phenyl, 1-naphthyl, 2-naphthyl, tetralinyl, indanyl, dihydronaphthyl or 6,7,8,9-tetrahydro-5H-benzo[a]cycloheptenyl, each of which is optionally substituted with one, two or three of the following substituents which can be the same or different and are:
- (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$, $C_1$-$C_3$ alkoxy-($R_{1\text{-}aryl}$), $C_1$-$C_3$ alkoxy-($R_{1\text{-}heteroaryl}$),
- (2) —OH,
- (3) —NO$_2$,
- (4) —F, —Cl, —Br, or —I,
- (5) —CO—OH,
- (6) —C≡N,
- (7) —(CH$_2$)$_{0\text{-}4}$—CO—NR$_{N\text{-}2}$R$_{N\text{-}3}$,
- (8) —(CH$_2$)$_{0\text{-}4}$—CO—($C_1$-$C_{12}$ alkyl),
- (9) —(CH$_2$)$_{0\text{-}4}$—CO—($C_2$-$C_{12}$ alkenyl with one, two or three double bonds),
- (10) —(CH$_2$)$_{0\text{-}4}$—CO—($C_2$-$C_{12}$ alkynyl with one, two or three triple bonds),
- (11) —(CH$_2$)$_{0\text{-}4}$—CO—($C_3$-$C_7$ cycloalkyl),
- (12) —(CH$_2$)$_{0\text{-}4}$—CO—R$_{1\text{-}aryl}$,
- (13) —(CH$_2$)$_{0\text{-}4}$—CO—R$_{1\text{-}heteroaryl}$,
- (14) —(CH$_2$)$_{0\text{-}4}$—CO—R$_{1\text{-}heterocycle}$,
- (15) —(CH$_2$)$_{0\text{-}4}$—CO—R$_{N\text{-}4}$ where R$_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
- (16) —(CH$_2$)$_{0\text{-}4}$—CO—O—R$_{N\text{-}5}$ where R$_{N\text{-}5}$ is selected from the group consisting of:
  - (a) $C_1$-$C_6$ alkyl,
  - (b) —(CH$_2$)$_{0\text{-}2}$—($R_{1\text{-}aryl}$),
  - (c) $C_2$-$C_6$ alkenyl containing one or two double bonds,
  - (d) $C_2$-$C_6$ alkynyl containing one or two triple bonds,
  - (e) $C_3$-$C_7$ cycloalkyl, and
  - (f) —(CH$_2$)$_{0\text{-}2}$—($R_{1\text{-}heteroaryl}$)
- (17) —(CH$_2$)$_{0\text{-}4}$—SO$_2$—NR$_{N\text{-}2}$R$_{N\text{-}3}$,
- (18) —(CH$_2$)$_{0\text{-}4}$—SO—($C_1$-$C_8$ alkyl),
- (19) —(CH$_2$)$_{0\text{-}4}$—SO$_2$—($C_1$-$C_{12}$ alkyl),
- (20) —(CH$_2$)$_{0\text{-}4}$—SO$_2$—($C_3$-$C_7$ cycloalkyl),
- (21) —(CH$_2$)$_{0\text{-}4}$—N(H or R$_{N\text{-}5}$)—CO—O—R$_{N\text{-}5}$ where R$_{N\text{-}5}$ can be the same or different,
- (22) —(CH$_2$)$_{0\text{-}4}$—N(H or R$_{N\text{-}5}$)—CO—N(R$_{N\text{-}5}$)$_2$, where R$_{N\text{-}5}$ can be the same or different,
- (23) —(CH$_2$)$_{0\text{-}4}$—N—CS—N(R$_{N\text{-}5}$)$_2$, where R$_{N\text{-}5}$ can be the same or different,
- (24) —(CH$_2$)$_{0\text{-}4}$—N(—H or R$_{N\text{-}5}$)—CO—R$_{N\text{-}2}$ where R$_{N\text{-}5}$ and R$_{N\text{-}2}$ can be the same or different,
- (25) —(CH$_2$)$_{0\text{-}4}$—NR$_{N\text{-}2}$R$_{N\text{-}3}$ where R$_{N\text{-}2}$ and R$_{N\text{-}3}$ can be the same or different,
- (26) —(CH$_2$)$_{0\text{-}4}$—R$_{N\text{-}4}$,
- (27) —(CH$_2$)$_{0\text{-}4}$—O—CO—($C_1$-$C_6$ alkyl),
- (28) —(CH$_2$)$_{0\text{-}4}$—O—P(O)—(OR$_{N\text{-}aryl\text{-}1}$)$_2$ where R$_{N\text{-}aryl\text{-}1}$ is —H or $C_1$-$C_4$ alkyl,
- (29) —(CH$_2$)$_{0\text{-}4}$—O—CO—N(R$_{N\text{-}5}$)$_2$,
- (30) —(CH$_2$)$_{0\text{-}4}$—O—CS—N(R$_{N\text{-}5}$)$_2$,
- (31) —(CH$_2$)$_{0\text{-}4}$—O—(R$_{N\text{-}5}$)$_2$,
- (32) —(CH$_2$)$_{0\text{-}4}$—O—(R$_{N\text{-}5}$)$_2$—COOH,
- (33) —(CH$_2$)$_{0\text{-}4}$—S—(R$_{N\text{-}5}$)$_2$,
- (34) —(CH$_2$)$_{0\text{-}4}$—O—($C_1$-$C_6$ alkyl optionally substituted with one, two, three, four, or five —F),
- (35) $C_3$-$C_7$ cycloalkyl,
- (36) $C_2$-$C_6$ alkenyl with one or two double bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1\text{-}a}$R$_{1\text{-}b}$, $C_1$-$C_3$ alkoxy-($R_{1\text{-}aryl}$), $C_1$-$C_3$ alkoxy-($R_{1\text{-}heteroaryl}$),
- (37) $C_2$-$C_6$ alkynyl with one or two triple bonds optionally substituted with $C_1$-$C_3$ alkyl, —F, —Cl, —Br, —I, —OH, —SH, —C≡N, —CF$_3$, $C_1$-$C_3$ alkoxy, or —NR$_{1\text{-}a}$R$_{1\text{-}b}$, $C_1$-$C_3$ alkoxy-($R_{1\text{-}aryl}$), $C_1$-$C_3$ alkoxy-($R_{1\text{-}heteroaryl}$),
- (38) —(CH$_2$)$_{0\text{-}4}$—N(—H or R$_{N\text{-}5}$)—SO$_2$—R$_{N\text{-}2}$ where R$_{N\text{-}5}$ and R$_{N\text{-}2}$ can be the same or different, or
- (39) —(CH$_2$)$_{0\text{-}4}$—$C_3$-$C_7$ cycloalkyl.

In yet another embodiment, $R_1$ and $R_3$ are independently R$_{N\text{-}1}$C(O)—; and R$_{N\text{-}1}$ is R$_{N\text{-}heteroaryl}$ where R$_{N\text{-}heteroaryl}$ is selected from the group consisting of:
pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl,carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, where the R$_{N\text{-}heteroaryl}$ group is bonded by any atom of the parent R$_{N\text{-}heteroaryl}$ group substituted by hydrogen such that the new bond to the R$_{N\text{-}heteroaryl}$ group replaces the hydrogen atom and its bond, where heteroaryl is optionally substituted with one, two, three, or four of:
- (1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1\text{-}a}$R$_{1\text{-}b}$, $C_1$-$C_3$ alkoxy-($R_{1\text{-}aryl}$), $C_1$-$C_3$ alkoxy-($R_{1\text{-}heteroaryl}$),
- (2) —OH,
- (3) —NO$_2$,
- (4) —F, —Cl, —Br, or —I
- (5) —CO—OH,
- (6) —C≡N,
- (7) —(CH$_2$)$_{0\text{-}4}$—CO—NR$_{N\text{-}2}$R$_{N\text{-}3}$,
- (8) —(CH$_2$)$_{0\text{-}4}$—CO—($C_1$-$C_{12}$ alkyl),
- (9) —(CH$_2$)$_{0\text{-}4}$—CO—($C_2$-$C_{12}$ alkenyl with one, two or three double bonds),

(10) —$(CH_2)_{0-4}$—CO—($C_2$-$C_{12}$ alkynyl with one, two or three triple bonds),
(11) —$(CH_2)_{0-4}$—CO—($C_3$-$C_7$ cycloalkyl),
(12) —$(CH_2)_{0-4}$—CO—$R_{1\text{-}aryl}$,
(13) —$(CH_2)_{0-4}$—CO—$R_{1\text{-}heteroaryl}$,
(14) —$(CH_2)_{0-4}$—CO—$R_{1\text{-}heterocycle}$,
(15) —$(CH_2)_{0-4}$—CO—$R_{N\text{-}4}$,
(16) —$(CH_2)_{0-4}$—CO—O—$R_{N\text{-}5}$,
(17) —$(CH_2)_{0-4}$—$SO_2$—$NR_{N\text{-}2}R_{N\text{-}3}$,
(18) —$(CH_2)_{0-4}$—SO—($C_1$-$C_8$ alkyl),
(19) —$(CH_2)_{0-4}$—$SO_2$—($C_1$-$C_{12}$ alkyl),
(20) —$(CH_2)_{0-4}$—$SO_2$—($C_3$-$C_7$ cycloalkyl),
(21) —$(CH_2)_{0-4}$—N(H or $R_{N\text{-}5}$)—CO—O—$R_{N\text{-}5}$ where $R_{N\text{-}5}$ can be the same or different,
(22) —$(CH_2)_{0-4}$—N(H or $R_{N\text{-}5}$)—CO—N($R_{N\text{-}5}$)$_2$, where $R_{N\text{-}5}$ can be the same or different,
(23) —$(CH_2)_{0-4}$—N—CS—N($R_{N\text{-}5}$)$_2$, where $R_{N\text{-}5}$ can be the same or different,
(24) —$(CH_2)_{0-4}$—N(—H or $R_{N\text{-}5}$)—CO—$R_{N\text{-}2}$ where $R_{N\text{-}5}$ and $R_{N\text{-}2}$ can be the same or different,
(25) —$(CH_2)_{0-4}$—$NR_{N\text{-}2}R_{N\text{-}3}$ where $R_{N\text{-}2}$ and $R_{N\text{-}3}$ can be the same or different,
(26) —$(CH_2)_{0-4}$—$R_{N\text{-}4}$,
(27) —$(CH_2)_{0-4}$—O—CO—($C_1$-$C_6$ alkyl),
(28) —$(CH_2)_{0-4}$—O—P(O)—($OR_{N\text{-}aryl\text{-}1}$)$_2$ where $R_{N\text{-}aryl\text{-}1}$ is —H or $C_1$-$C_4$ alkyl,
(29) —$(CH_2)_{0-4}$—O—CO—N($R_{N\text{-}5}$)$_2$,
(30) —$(CH_2)_{0-4}$—O—CS—N($R_{N\text{-}5}$)$_2$,
(31) —$(CH_2)_{0-4}$—O—($R_{N\text{-}5}$)$_2$,
(32) —$(CH_2)_{0-4}$—O—($R_{N\text{-}5}$)$_2$—COOH,
(33) —$(CH_2)_{0-4}$—S—($R_{N\text{-}5}$)$_2$,
(34) —$(CH_2)_{0-4}$—O—($C_1$-$C_6$ alkyl optionally substituted with one, two, three, four, or five —F),
(35) $C_3$-$C_7$ cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$, $C_1$-$C_3$ alkoxy-($R_{1\text{-}aryl}$), $C_1$-$C_3$ alkoxy-($R_{1\text{-}heteroaryl}$),
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$, $C_1$-$C_3$ alkoxy-($R_{1\text{-}aryl}$), $C_1$-$C_3$ alkoxy-($R_{1\text{-}heteroaryl}$),
(38) —$(CH_2)_{0-4}$—N(—H or $R_{N\text{-}5}$)—$SO_2$—$R_{N\text{-}2}$ where $R_{N\text{-}5}$ and $R_{N\text{-}2}$ can be the same or different, or
(39) —$(CH_2)_{0-4}$—$C_3$-$C_7$ cycloalkyl.

In a further embodiment, $R_1$ and $R_3$ are independently $R_{N\text{-}2}C(O)$—; and $R_{N\text{-}1}$ is phenyl, 1-naphthyl, or 2-naphthyl, each of which is optionally substituted with one, two or three of the following substituents which can be the same or different and are:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —$CF_3$, $C_1$-$C_3$ alkoxy, and —$NR_{1\text{-}a}R_{1\text{-}b}$, $C_1$-$C_3$ alkoxy-($R_{1\text{-}aryl}$), $C_1$-$C_3$ alkoxy-($R_{1\text{-}heteroaryl}$),
(2) —OH,
(3) —$NO_2$,
(4) —F, —Cl, —Br, or —I,
(5) —CO—OH,
(6) —C≡N,
(7) —$(CH_2)_{0-4}$—CO—$NR_{N\text{-}2}R_{N\text{-}3}$,
(8) —$(CH_2)_{0-4}$—CO—($C_1$-$C_{12}$ alkyl),
(9) —$(CH_2)_{0-4}$—CO—($C_2$-$C_{12}$ alkenyl with one, two or three double bonds),
(10) —$(CH_2)_{0-4}$—CO—($C_2$-$C_{12}$ alkynyl with one, two or three triple bonds),
(11) —$(CH_2)_{0-4}$—CO—($C_3$-$C_7$ cycloalkyl),
(12) —$(CH_2)_{0-4}$—CO—$R_{1\text{-}aryl}$,
(13) —$(CH_2)_{0-4}$—CO—$R_{1\text{-}heteroaryl}$,
(14) —$(CH_2)_{0-4}$—CO—$R_{1\text{-}heterocycle}$,
(15) —$(CH_2)_{0-4}$—CO—$R_{N\text{-}4}$ where $R_{N\text{-}4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: $C_1$-$C_6$ alkyl,
(16) —$(CH_2)_{0-4}$—CO—O—$R_{N\text{-}5}$ where $R_{N\text{-}5}$ is selected from the group consisting of:
  (a) $C_1$-$C_6$ alkyl,
  (b) —$(CH_2)_{0-2}$—($R_{1\text{-}aryl}$),
  (c) $C_2$-$C_6$ alkenyl containing one or two double bonds,
  (d) $C_2$-$C_6$ alkynyl containing one or two triple bonds,
  (e) $C_3$-$C_7$ cycloalkyl, and
  (f) —$(CH_2)_{0-2}$—($R_{1\text{-}heteroaryl}$),
(17) —$(CH_2)_{0-4}$—$SO_2$—$NR_{N\text{-}2}R_{N\text{-}3}$,
(18) —$(CH_2)_{0-4}$—SO—($C_1$-$C_8$ alkyl),
(19) —$(CH_2)_{0-4}$—$SO_2$—($C_1$-$C_{12}$ alkyl),
(20) —$(CH_2)_{0-4}$—$SO_2$—($C_3$-$C_7$ cycloalkyl),
(21) —$(CH_2)_{0-4}$—N(H or $R_{N\text{-}5}$)—CO—O—$R_{N\text{-}5}$ where $R_{N\text{-}5}$ can be the same or different,
(22) —$(CH_2)_{0-4}$—N(H or $R_{N\text{-}5}$)—CO—N($R_{N\text{-}5}$)$_2$, where $R_{N\text{-}5}$ can be the same or different,
(23) —$(CH_2)_{0-4}$—N—CS—N($R_{N\text{-}5}$)$_2$, where $R_{N\text{-}5}$ can be the same or different,
(24) —$(CH_2)_{0-4}$—N(—H or $R_{N\text{-}5}$)—CO—$R_{N\text{-}2}$ where $R_{N\text{-}5}$ and $R_{N\text{-}2}$ can be the same or different,
(25) —$(CH_2)_{0-4}$—$NR_{N\text{-}2}R_{N\text{-}3}$ where $R_{N\text{-}2}$ and $R_{N\text{-}3}$ can be the same or different,
(26) —$(CH_2)_{0-4}$—$R_{N\text{-}4}$,
(27) —$(CH_2)_{0-4}$—O—CO—($C_1$-$C_6$ alkyl),
(28) —$(CH_2)_{0-4}$—O—P(O)—($OR_{N\text{-}aryl}$)$_2$ where $R_{N\text{-}aryl\text{-}1}$ is —H or $C_1$-$C_4$ alkyl,
(29) —$(CH_2)_{0-4}$—O—CO—N($R_{N\text{-}5}$)$_2$,
(30) —$(CH_2)_{0-4}$—O—CS—N($R_{N\text{-}5}$)$_2$,
(31) —$(CH_2)_{0-4}$—O—($R_{N\text{-}5}$)$_2$,
(32) —$(CH_2)_{0-4}$—O—($R_{N\text{-}5}$)$_2$—COOH,
(33) —$(CH_2)_{0-4}$—S—($R_{N\text{-}5}$)$_2$,
(34) —$(CH_2)_{0-4}$—O—($C_1$-$C_6$ alkyl optionally substituted with one, two, three, four, or five —F),
(35) $C_3$-$C_7$ Cycloalkyl,
(36) $C_2$-$C_6$ alkenyl with one or two double bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$, $C_1$-$C_3$ alkoxy-($R_{1\text{-}aryl}$), $C_1$-$C_3$ alkoxy-($R_{1\text{-}heteroaryl}$),
(37) $C_2$-$C_6$ alkynyl with one or two triple bonds optionally substituted with $C_1$-$C_3$ alkyl, —F, —Cl, —Br, —I, —OH, —SH, —C≡N, —$CF_3$, $C_1$-$C_3$ alkoxy, or —$NR_{1\text{-}a}R_{1\text{-}b}$, $C_1$-$C_3$ alkoxy-($R_{1\text{-}aryl}$), $C_1$-$C_3$ alkoxy-($R_{1\text{-}heteroaryl}$),
(38) —$(CH_2)_{0-4}$—N(—H or $R_{N\text{-}5}$)—$SO_2$—$R_{N\text{-}2}$ where $R_{N\text{-}5}$ and $R_{N\text{-}2}$ can be the same or different, or
(39) —$(CH_2)_{0-4}$—$C_3$-$C_7$ cycloalkyl.

In still another embodiment, $R_1$ and $R_3$ are independently $R_{N\text{-}1}C(O)$—; and
$R_{N\text{-}1}$ is phenyl optionally substituted with one, two or three of the following substituents which can be the same or different and are:
(1) $C_1$-$C_6$ alkyl, optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (2) —OH,
(3) —NO$_2$,
(4) —F, —Cl, —Br, or —I,
(5) —CO—OH,
(6) —C≡N,
(7) —(CH$_2$)$_{0-4}$—CO—NR$_{N-2}$R$_{N-3}$,
(8) —(CH$_2$)$_{0-4}$—CO—(C$_1$-C$_{12}$ alkyl),
(9) —(CH$_2$)$_{0-4}$—CO—(C$_2$-C$_{12}$ alkenyl with one, two or three double bonds),
(10) —(CH$_2$)$_{0-4}$—CO—(C$_2$-C$_{12}$ alkynyl with one, two or three triple bonds),
(11) —(CH$_2$)$_{0-4}$—CO—(C$_3$-C$_7$ cycloalkyl),
(12) —(CH$_2$)$_{0-4}$—CO—R$_{1-aryl}$,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: C$_1$-C$_6$ alkyl,
(16) —(CH$_2$)$_{0-4}$—CO—O—R$_{N-5}$ where R$_{N-5}$ is selected from the group consisting of:
 (a) C$_1$-C$_6$ alkyl,
 (b) —(CH$_2$)$_{0-2}$—(R$_{1-aryl}$),
 (c) C$_2$-C$_6$ alkenyl containing one or two double bonds,
 (d) C$_2$-C$_6$ alkynyl containing one or two triple bonds,
 (e) C$_3$-C$_7$ cycloalkyl, and
 (f) —(CH$_2$)$_{0-2}$—(R$_{1-heteroaryl}$),
(17) —(CH$_2$)$_{0-4}$—SO$_2$—NR$_{N-2}$R$_{N-3}$,
(18) —(CH$_2$)$_{0-4}$—SO—(C$_1$-C$_8$ alkyl),
(19) —(CH$_2$)$_{0-4}$—SO$_2$—(C$_1$-C$_{12}$ alkyl),
(20) —(CH$_2$)$_{0-4}$—SO$_2$—(C$_3$-C$_7$ cycloalkyl),
(21) —(CH$_2$)$_{0-4}$—N(H or R$_{N-5}$)—CO—O—R$_{N-5}$ where R$_{N-5}$ can be the same or different,
(22) —(CH$_2$)$_{0-4}$—N(H or R$_{N-5}$)—CO—N(R$_{N-5}$)$_2$, where R$_{N-5}$ can be the same or different,
(23) —(CH$_2$)$_{0-4}$—N—CS—N(R$_{N-5}$)$_2$, where R$_{N-5}$ can be the same or different,
(24) —(CH$_2$)$_{0-4}$—N(—H or R$_{N-5}$)—CO—R$_{N-2}$ where R$_{N-5}$ and R$_{N-2}$ can be the same or different,
(25) —(CH$_2$)$_{0-4}$—NR$_{N-2}$R$_{N-3}$ where R$_{N-2}$ and R$_{N-3}$ can be the same or different,
(26) —(CH$_2$)$_{0-4}$—R$_{N-4}$,
(27) —(CH$_2$)$_{0-4}$—O—CO—(C$_1$-C$_6$ alkyl),
(28) —(CH$_2$)$_{0-4}$—O—P(O)—(OR$_{N-aryl-1}$)$_2$ where R$_{N-aryl-1}$ is —H or C$_1$-C$_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$)$_2$,
(32) —(CH$_2$)$_{0-4}$—O—(R$_{N-5}$)$_2$—COOH,
(33) —(CH$_2$)$_{0-4}$—S—(R$_{N-5}$)$_2$,
(34) —(CH$_2$)$_{0-4}$—O—(C$_1$-C$_6$ alkyl optionally substituted with one, two, three, four, or five —F),
(35) C$_3$-C$_7$ cycloalkyl,
(36) C$_2$-C$_6$ alkenyl with one or two double bonds optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$, C$_1$-C$_3$ alkoxy-(R$_{1-aryl}$), C$_1$-C$_3$ alkoxy-(R$_{1-heteroaryl}$),
(37) C$_2$-C$_6$ alkynyl with one or two triple bonds optionally substituted with C$_1$-C$_3$ alkyl, —F, —Cl, —Br, —I, —OH, —SH, —C≡N, —CF$_3$, C$_1$-C$_3$ alkoxy, or —NR$_{1-a}$R$_{1-b}$, C$_1$-C$_3$ alkoxy-(R$_{1-aryl}$), C$_1$-C$_3$ alkoxy-(R$_{1-heteroaryl}$),
(38) —(CH$_2$)$_{0-4}$—N(—H or R$_{N-5}$)—SO$_2$—R$_{N-2}$ where R$_{N-5}$ and R$_{N-2}$ can be the same or different, or
(39) —(CH$_2$)$_{0-4}$—C$_3$-C$_7$ cycloalkyl.

In another embodiment, R$_1$ and R$_3$ are independently R$_{N-2}$C(O)—; and

R$_{N-1}$ is phenyl of which is optionally substituted with one, two or three of the following substituents which can be the same or different and are:
(1) C$_1$-C$_6$ alkyl, optionally substituted with one, two or three substituents selected from the group consisting of C$_1$-C$_3$ alkyl, —F, —Cl, —Br, —I, —OH, —SH, —C≡N, —CF$_3$, C$_1$-C$_3$ alkoxy, and —NR$_{1-a}$R$_{1-b}$, C$_1$-C$_3$ alkoxy-(R$_{1-aryl}$), C$_1$-C$_3$ alkoxy-(R$_{1-heteroaryl}$),
(2) —OH,
(3) —NO$_2$,
(4) —F, —Cl, —Br, or —I,
(5) —CO—OH,
(6) —C≡N,
(7) —(CH$_2$)$_{0-4}$—CO—NR$_{N-2}$R$_{N-3}$,
(8) —(CH$_2$)$_{0-4}$—CO—(C$_1$-C$_{12}$ alkyl),
(9) —(CH$_2$)$_{0-4}$—CO—(C$_2$-C$_{12}$ alkenyl with one, two or three double bonds),
(10) —(CH$_2$)$_{0-4}$—CO—(C$_2$-C$_{12}$ alkynyl with one, two or three triple bonds),
(11) —(CH$_2$)$_{0-4}$—CO—(C$_3$-C$_7$ cycloalkyl),
(12) —(CH$_2$)$_{0-4}$—CO—R$_{1-aryl}$,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$ where R$_{N-4}$ is selected from the group consisting of morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with one, two, three, or four of: C$_1$-C$_6$ alkyl,
(16) —(CH$_2$)$_{0-4}$—CO—O—R$_{N-5}$ where R$_{N-5}$ is selected from the group consisting of:
 (a) C$_1$-C$_6$ alkyl,
 (b) —(CH$_2$)$_{0-2}$—(R$_{1-aryl}$),
 (c) C$_2$-C$_6$ alkenyl containing one or two double bonds,
 (d) C$_2$-C$_6$ alkynyl containing one or two triple bonds, and
 (e) C$_3$-C$_7$ cycloalkyl,
(17) —(CH$_2$)$_{0-4}$—N(H or R$_{N-5}$)—CO—O—R$_{N-5}$ where R$_{N-5}$ can be the same or different,
(18) —(CH$_2$)$_{0-4}$—N(H or R$_{N-5}$)—CO—N(R$_{N-5}$)$_2$, where R$_{N-5}$ can be the same or different,
(19) —(CH$_2$)$_{0-4}$—N—CS—N(R$_{N-5}$)$_2$, where R$_{N-5}$ can be the same or different,
(20) —(CH$_2$)$_{0-4}$—N(—H or R$_{N-5}$)—CO—R$_{N-2}$ where R$_{N-5}$ and R$_{N-2}$ can be the same or different,
(21) —(CH$_2$)$_{0-4}$—NR$_{N-2}$R$_{N-3}$ where R$_{N-2}$ and R$_{N-3}$ can be the same or different,
(22) —(CH$_2$)$_{0-4}$—R$_{N-4}$,
(23) —(CH$_2$)$_{0-4}$—O—CO—(C$_1$-C$_6$ alkyl),
(24) —(CH$_2$)$_{0-4}$—O—CO—N(R$_{N-5}$)$_2$,
(25) —(CH$_2$)$_{0-4}$—O—CS—N(R$_{N-5}$)$_2$,
(26) —(CH$_2$)$_{0-4}$—O—(R$_{N-5}$)$_2$,
(27) —(CH$_2$)$_{0-4}$—O—(R$_{N-5}$)$_2$—COOH,
(28) —(CH$_2$)$_{0-4}$—O—(C$_1$-C$_6$ alkyl optionally substituted with one, two, three, four, or five —F),
(29) —(CH$_2$)$_{0-4}$—N(—H or R$_{N-5}$)—SO$_2$—R$_{N-2}$ where R$_{N-5}$ and R$_{N-2}$ can be the same or different, or
(30) —(CH$_2$)$_{0-4}$—C$_3$-C$_7$ cycloalkyl.

In another embodiment, $R_1$ and $R_3$ are independently $R_{N-1}C(O)$—; and $R_1$ represents —$(CH_2)_{n1}$-phenyl where $n_1$ is zero or one and where phenyl is optionally substituted with one, two, or three of the following substituents which are the same or different:

(A) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (B) $C_2$-$C_6$ alkenyl with one or two double bonds, optionally substituted with one, two or three substituents selected from the group consisting of —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (C) $C_2$-$C_6$ alkynyl with one or two triple bonds, optionally substituted with one, two or three substituents selected from the group consisting of —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (D) —F, Cl, —Br, or —I, (E) —$C_1$-$C_6$ alkoxy optionally substituted with one, two, or three —F, (F) —NR$_{N-2}$R$_{N-3}$, where R$_{N-2}$ and R$_{N-3}$ are independently selected from the group consisting of:
(1) —H,
(2) —$C_1$-$C_6$ alkyl optionally substituted with one substituent selected from the group consisting of:
(a) —OH, and
(b) —NH$_2$,
(3) —$C_1$-$C_6$ alkyl optionally substituted with one to three —F, —Cl, —Br, or —I,
(4) —$C_3$-$C_7$ cycloalkyl,
(5) —($C_1$-$C_2$ alkyl)-($C_3$-$C_7$ cycloalkyl),
(6) —($C_1$-$C_6$ alkyl)-O—($C_1$-$C_3$ alkyl),
(7) —$C_2$-$C_6$ alkenyl with one or two double bonds,
(8) —$C_2$-$C_6$ alkynyl with one or two triple bonds,
(9) —$C_1$-$C_6$ alkyl chain with one double bond and one triple bond,
(10) —R$_{1-aryl}$, and
(11) —R$_1$-heteroaryl, (G) —OH, (H) —C≡N, (I) $C_3$-$C_7$ cycloalkyl, optionally substituted with one, two or three substituents selected from the group consisting of —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (J) —CO—($C_1$-$C_4$ alkyl), (K) —SO$_2$—NR$_{1-a}$R$_{1-b}$, (L) —CO—NR$_{1-a}$R$_{1-b}$, or (M) —SO$_2$—($C_1$-$C_4$ alkyl).

In a further embodiment, $R_1$ and $R_3$ are independently phenyl($C_1$-$C_6$)alkyl groups where the phenyl is optionally substituted with one or two groups independently selected from (A) $C_1$-$C_6$ alkyl optionally substituted with one, two or three substituents selected from the group consisting of $C_1$-$C_3$ alkyl, —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (B) —F, Cl, —Br, or —I, (C) —$C_1$-$C_6$ alkoxy optionally substituted with one, two, or three —F, (D) —NR$_{N-2}$R$_{N-3}$, where R$_{N-2}$ and R$_{N-3}$ are independently selected from the group consisting of:
(1) —H,
(2) —$C_1$-$C_6$ alkyl optionally substituted with one substituent selected from the group consisting of:
(a) —OH, and
(b) —NH$_2$,
(3) —$C_1$-$C_6$ alkyl optionally substituted with one to three —F, —Cl, —Br, or —I,
(4) —$C_3$-$C_7$ cycloalkyl,
(5) —($C_1$-$C_2$ alkyl)-($C_3$-$C_7$ cycloalkyl),
(6) —($C_1$-$C_6$ alkyl)-O—($C_1$-$C_3$ alkyl),
(9) —$C_1$-$C_6$ alkyl chain with one double bond and one triple bond, (E) —OH, (F) —C≡N, (G) $C_3$-$C_7$ cycloalkyl, optionally substituted with one, two or three substituents selected from the group consisting of —F, —Cl, —Br, —I, —OH, —SH, —C≡N, —CF$_3$, $C_1$-$C_3$ alkoxy, and —NR$_{1-a}$R$_{1-b}$, $C_1$-$C_3$ alkoxy-(R$_{1-aryl}$), $C_1$-$C_3$ alkoxy-(R$_{1-heteroaryl}$), (H) —CO—($C_1$-$C_4$ alkyl), (I) —SO$_2$—NR$_{1-a}$R$_{1-b}$, where R$_{1-a}$ and R$_{1-b}$ are as defined above, or (J) —CO—NR$_{1-a}$R$_{1-b}$, where R$_{1-a}$ and R$_{1-b}$ are as defined above.

Representative $R_1$ and $R_3$ groups also independently include benzyl, 4-hydroxybenzyl, 2-fluoro-4-propylbenzyl, 3-amino-4-bromobenzyl; 3-chloro-5-methylphenethyl, 3,5-difluorobenzyl, 2-methylphenylpropyl, 4-trifluoromethylbenzyl, 4-trifluoromethylphenethyl, 2,3-dichlorobenzyl, and 2-chloro-4-cyanobenzyl.

The invention encompasses compounds of formula I, which includes those compounds shown below wherein $R_1$, $R_2$ and $R_3$ are as defined above:

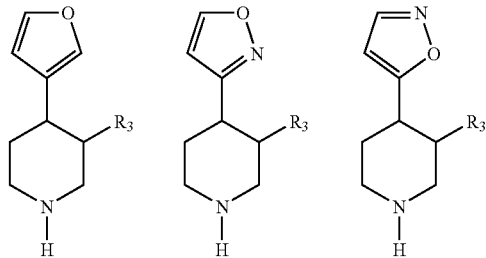

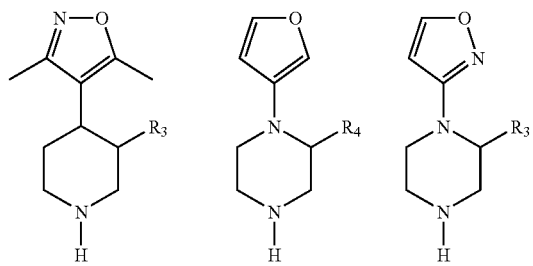

-continued

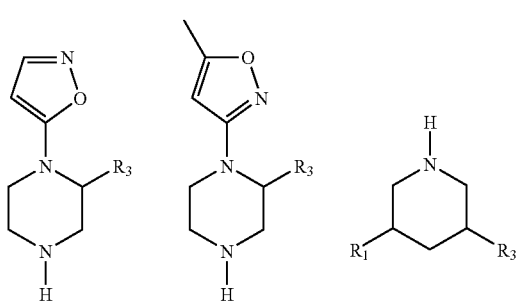

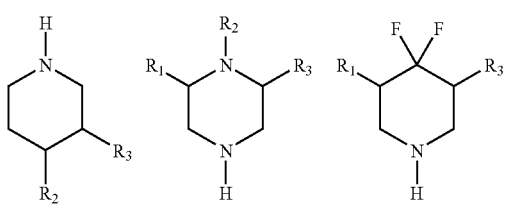

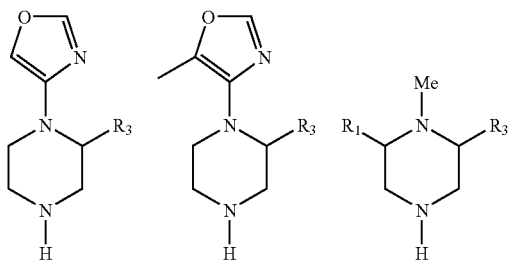

The invention encompasses compounds of formula I, which further includes compounds shown below, wherein $R_{11}$ is —$(CH_2)_{n1}$—$(R_{1\text{-}aryl})$, or —$(CH_2)_{n1}$—O—$(R_{1\text{-}aryl})$, wherein n1 and $R_{1\text{-}aryl}$ are as defined above:

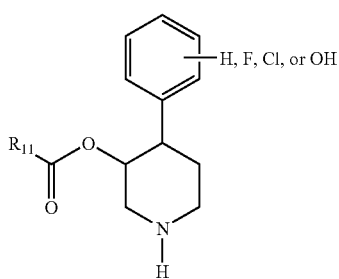

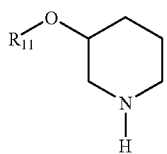

The invention encompasses compounds contemplated by Formula I, and more particularly those compounds shown below:

3-Alkyloxy-4-Furano-Piperidines

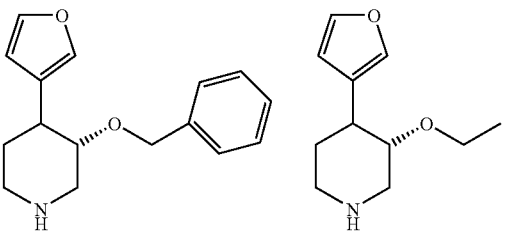

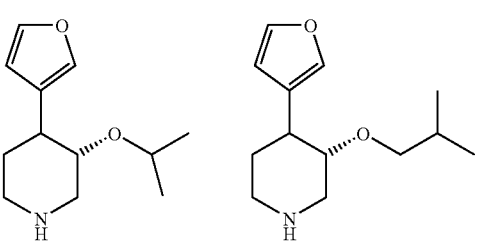

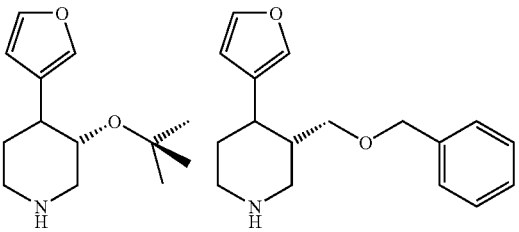

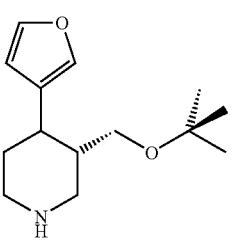

3-Alkyloxy-4-Isoxazolo-Piperidines

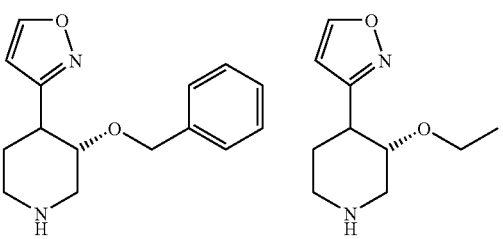

-continued
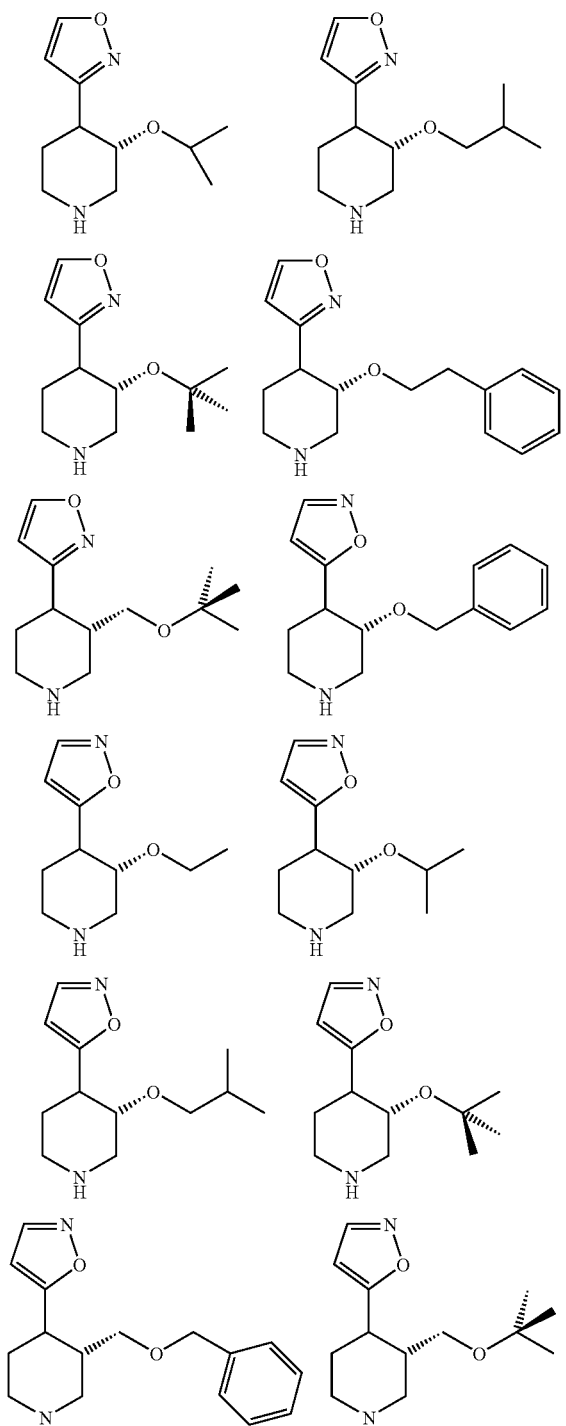
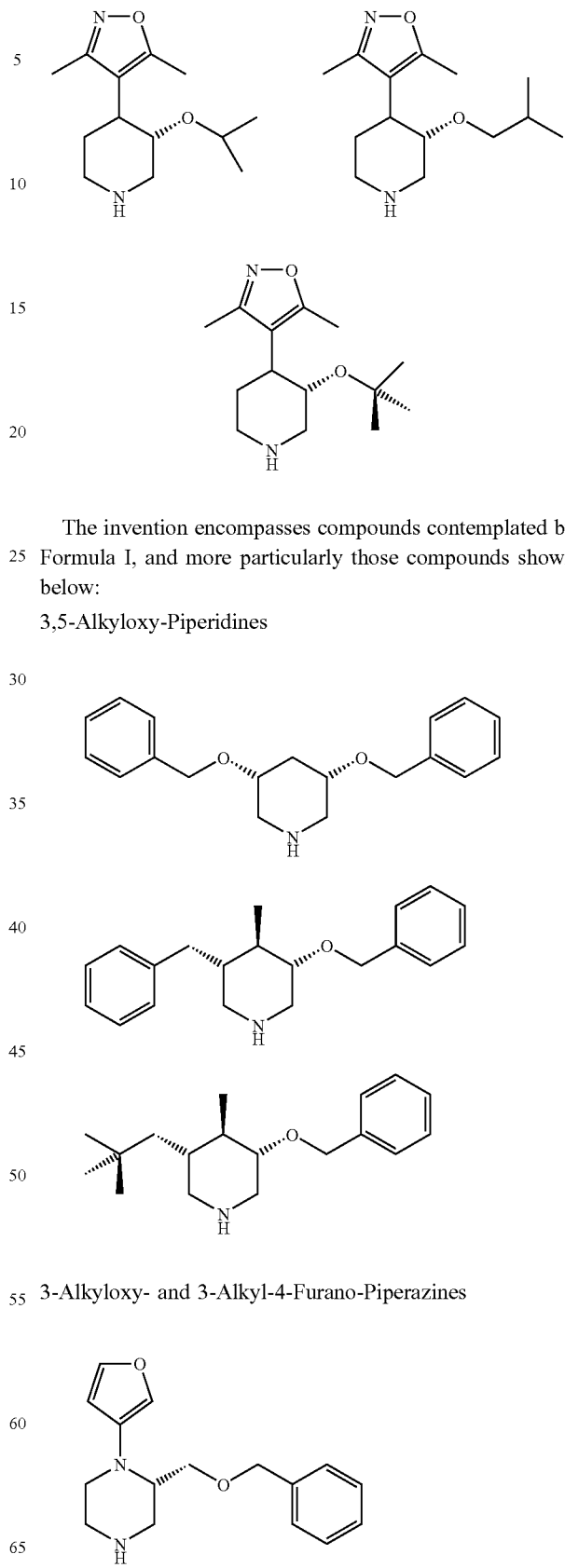
The invention encompasses compounds contemplated by Formula I, and more particularly those compounds shown below:
3,5-Alkyloxy-Piperidines
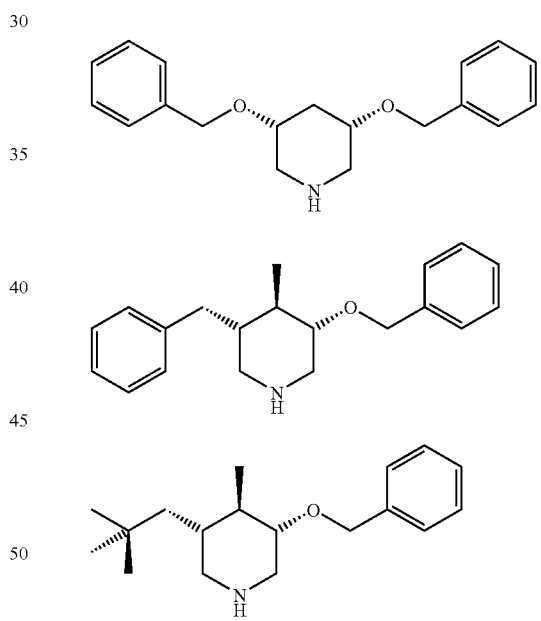
3-Alkyloxy- and 3-Alkyl-4-Furano-Piperazines
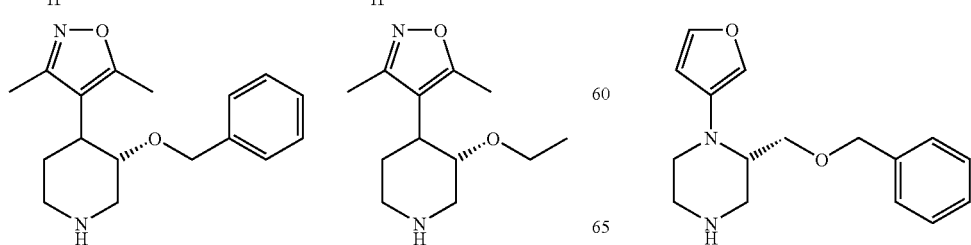

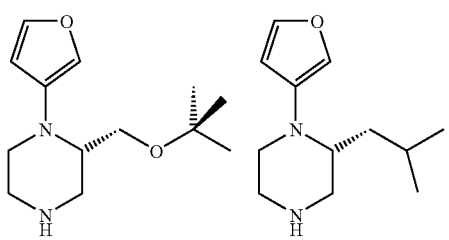
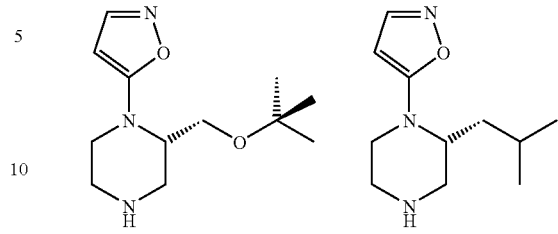
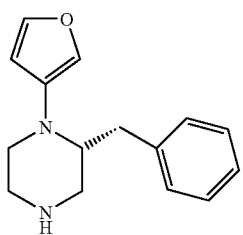
3-Alkyloxy- and 3-Alkyl-4Isoxazolo-Piperazines
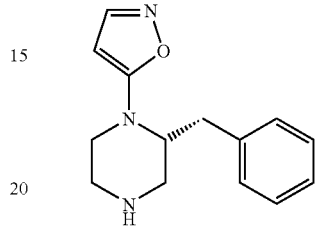
3-Alkyloxy- and 3-Alkyl-4-Oxazolo-Piperazines
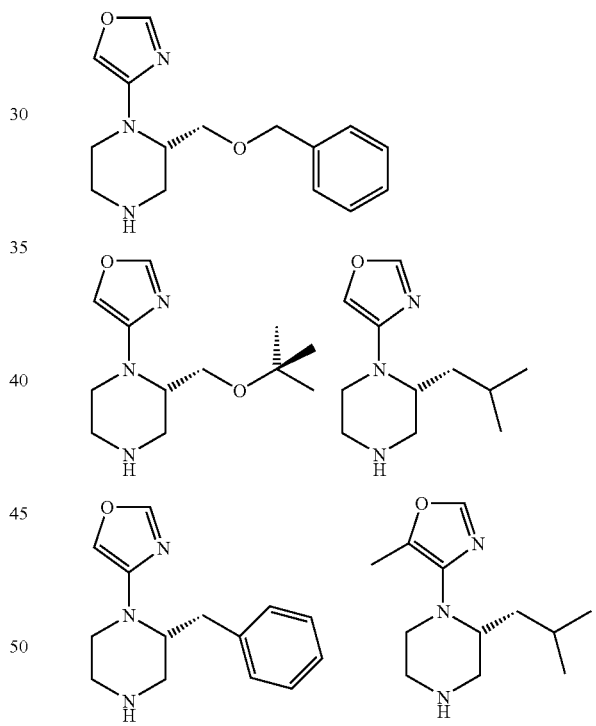
The invention encompasses compounds contemplated by Formula I, and more specifically those compounds shown below:
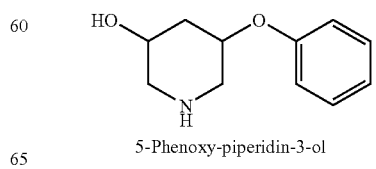
5-Phenoxy-piperidin-3-ol -continued

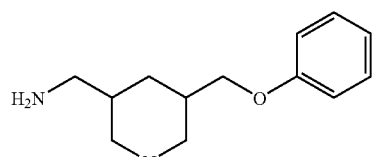
C-(5-Phenoxymethyl-piperidin-3-yl)-methylamine

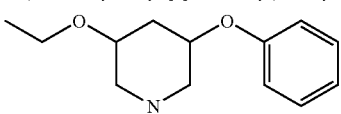
3-Ethoxy-5-phenoxy-piperidine

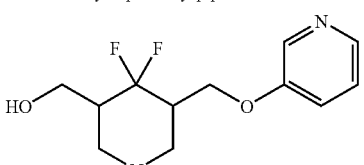
[4,4-Difluoro-5-(pyridin-3-yloxymethyl)-piperidin-3-yl-methanol

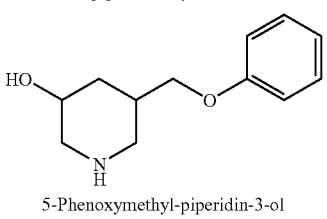
5-Phenoxymethyl-piperidin-3-ol

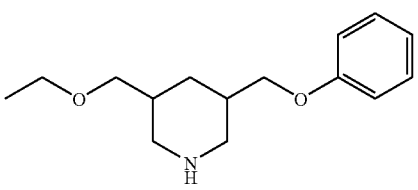
3-Ethoxymethyl-5-phenoxymethyl-piperidine

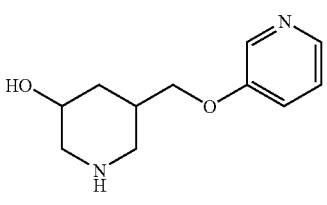
5-(Pyridin-3-yloxymethyl)-piperidin-3-ol

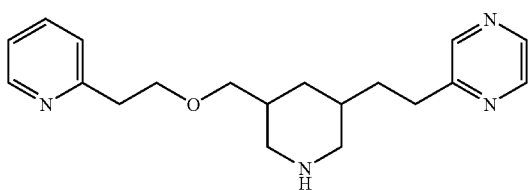
2-[2-[5-(2-Pyridin-2-yl-ethoxymethyl)-piperidin-3-yl]-ethyl]-pyrazine

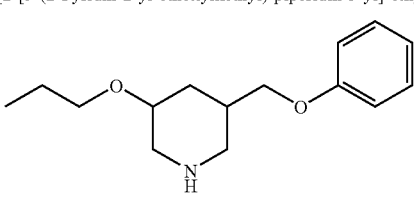
3-Phenoxymethyl-5-proproxy-piperidine

-continued

3-(4-Bromo-phenoxymethyl)-5-(4-chloro-phenoxymethyl)-piperidine

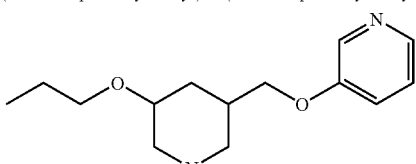
3-(5-Propoxy-piperidine-3-ylmethoxy)-pyridine

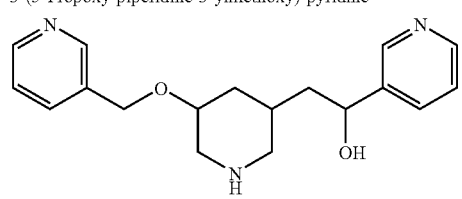
1-Pyridin-3-yl-2-[5-(pyridin-3-ylmethoxy)-piperidin-3-yl]-ethanol

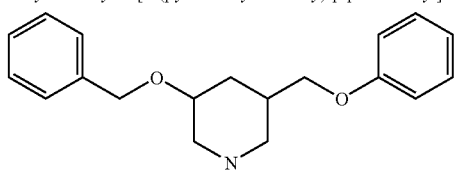
3-Benzyloxy-5-phenoxymethyl-piperidine

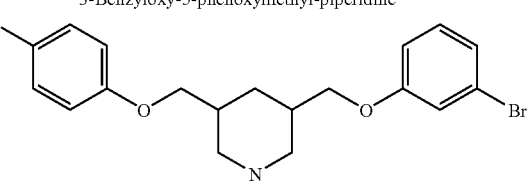
3-(4-Bromo-benzyloxymethyl)-5-(4-bromo-phenoxymethyl)-piperidine

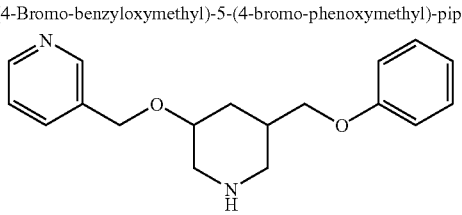
3-(5-Phenoxymethyl-piperidin-3-yloxymethyl)-piperidine

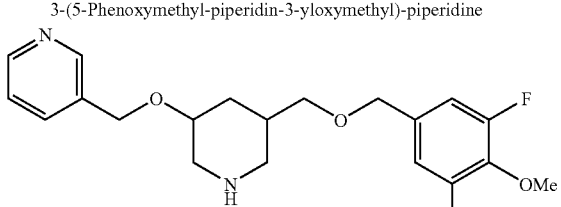
3-[5-(3,5-Diflouro-4-methoxy-benzyloxymethyl)-piperidin-3-yloxymethyl]-pyridine

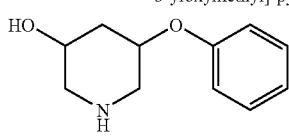
5-Phenoxy-piperidin-3-ol

-continued

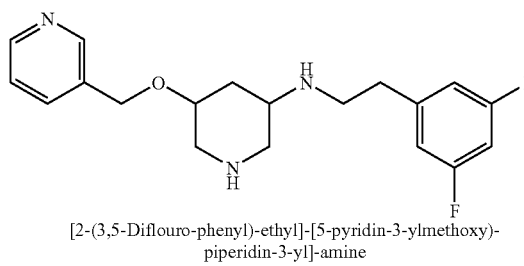

[2-(3,5-Diflouro-phenyl)-ethyl]-[5-pyridin-3-ylmethoxy)-piperidin-3-yl]-amine

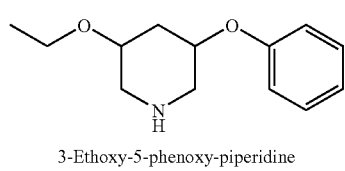

3-Ethoxy-5-phenoxy-piperidine

The invention encompasses compounds contemplated by Formula I, and more specifically those compounds shown below:

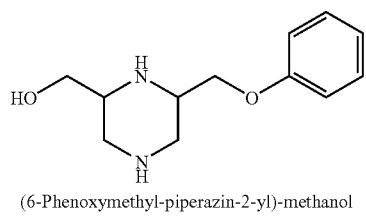

(6-Phenoxymethyl-piperazin-2-yl)-methanol

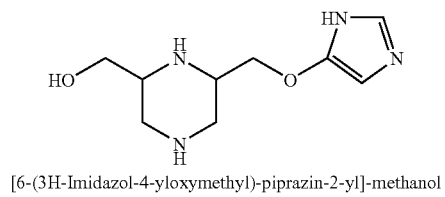

[6-(3H-Imidazol-4-yloxymethyl)-piprazin-2-yl]-methanol

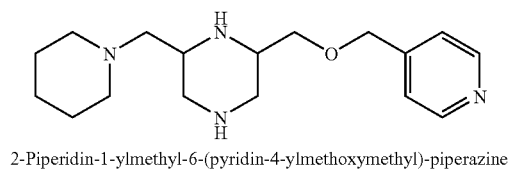

2-Piperidin-1-ylmethyl-6-(pyridin-4-ylmethoxymethyl)-piperazine

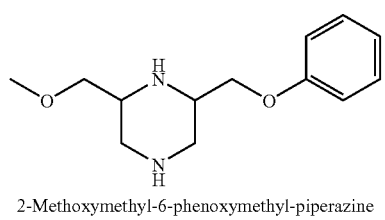

2-Methoxymethyl-6-phenoxymethyl-piperazine

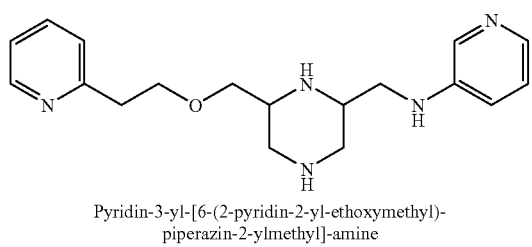

Pyridin-3-yl-[6-(2-pyridin-2-yl-ethoxymethyl)-piprazin-2-ylmethyl]-amine

-continued

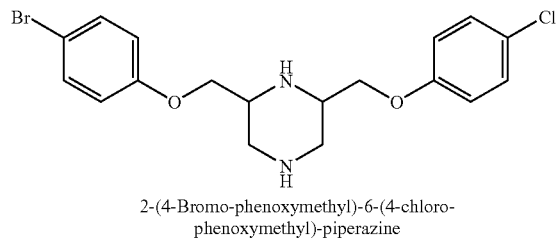

2-(4-Bromo-phenoxymethyl)-6-(4-chloro-phenoxymethyl)-piperazine

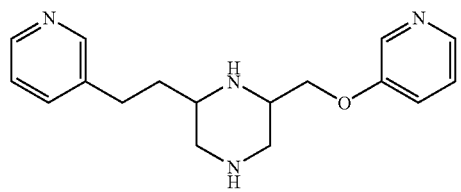

2-(2-Pyridin-3-yl-ethyl)-6-(pyridin-3-yloxymethyl)-piperazine

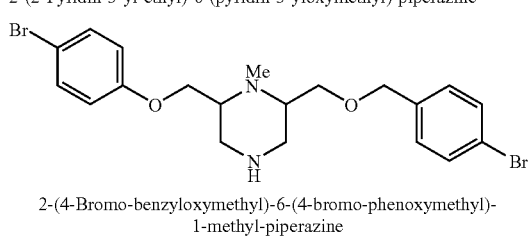

2-(4-Bromo-benzyloxymethyl)-6-(4-bromo-phenoxymethyl)-1-methyl-piperazine

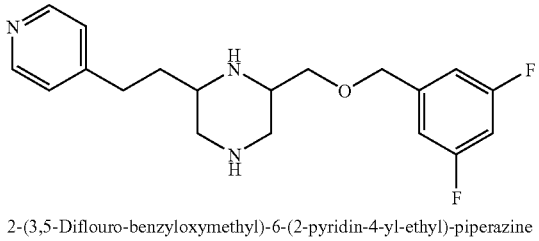

2-(3,5-Diflouro-benzyloxymethyl)-6-(2-pyridin-4-yl-ethyl)-piperazine

The invention encompasses compounds contemplated by Formula I, and more specifically those compounds shown below:

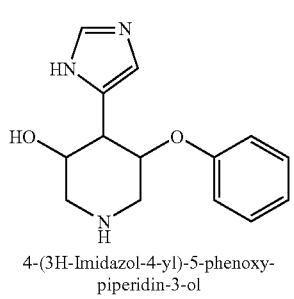

4-(3H-Imidazol-4-yl)-5-phenoxy-piperidin-3-ol

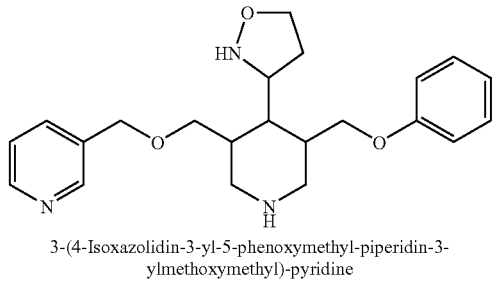

3-(4-Isoxazolidin-3-yl-5-phenoxymethyl-piperidin-3-ylmethoxymethyl)-pyridine

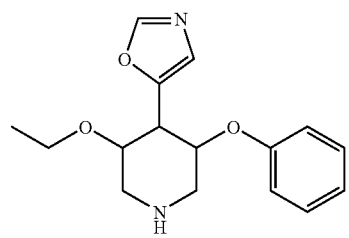

3-Ethoxy-4-oxazol-5-yl-5-phenoxy-piperidine

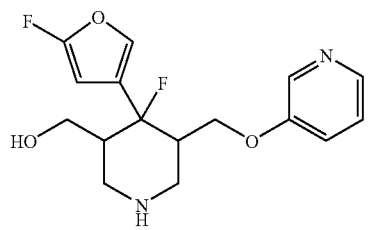

[4-Fluoro-4-(5-fluoro-furan-3-yl)-5-(pyridin-3-yloxymethyl)-piperidin-3-yl]-methanol

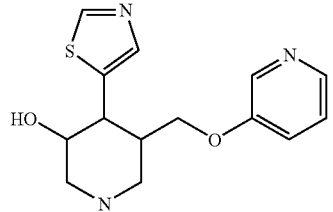

5-(Pyridin-3-yloxymethyl)-4-thiazol-5-yl-piperidin-3-ol

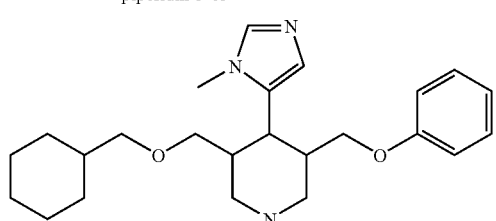

3-Cyclohexylmethoxymethyl-4-(3-methyl-3H-imidazol-4-yl)-5-phenoxymethyl-piperidine

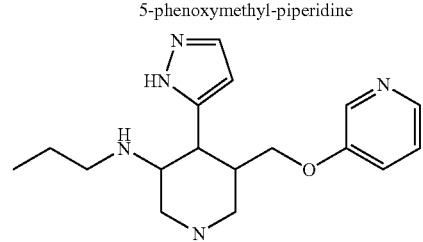

Propyl-[4-(2H-pyrazol-3-yl)-5-(pyridin-3-yloxymethyl)-piperidin-3-yl]-amine

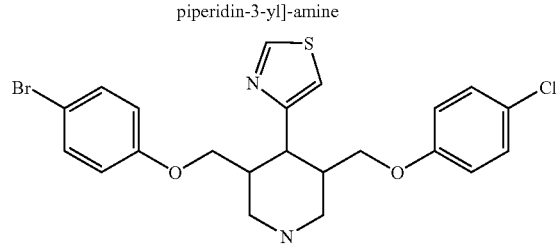

3-(4-Bromo-phenoxymethyl)-5-(4-chloro-phenoxymethyl)-4-thiazol-4-yl-piperidine

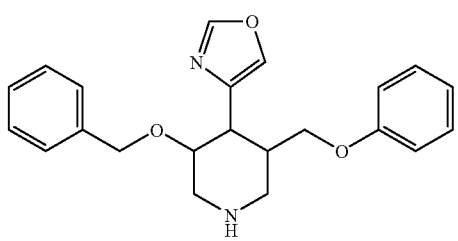

3-Benzyloxy-4-oxazol-4-yl-5-phenoxymethyl-piperidine

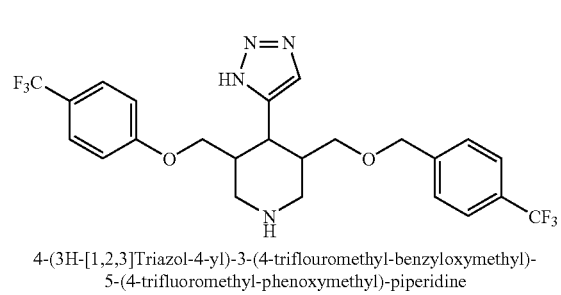

4-(3H-[1,2,3]Triazol-4-yl)-3-(4-triflouromethyl-benzyloxymethyl)-5-(4-trifluoromethyl-phenoxymethyl)-piperidine

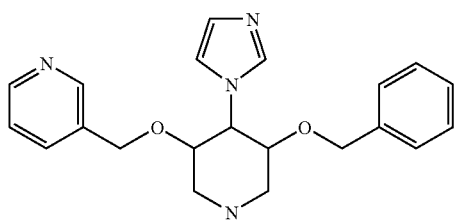

3-(5-Benzyloxy-4-Imidazol-1-yl-piperidin-3-yloxymethyl)-pyridine

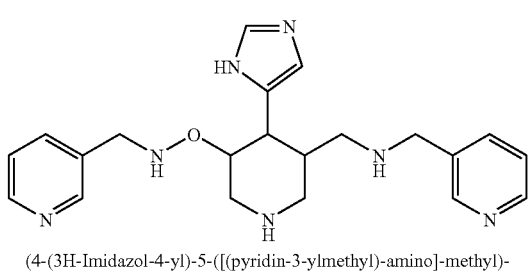

(4-(3H-Imidazol-4-yl)-5-([(pyridin-3-ylmethyl)-amino]-methyl)-piperidin-3-ylmethyl)-pyridin-3-ylmethyl-amine

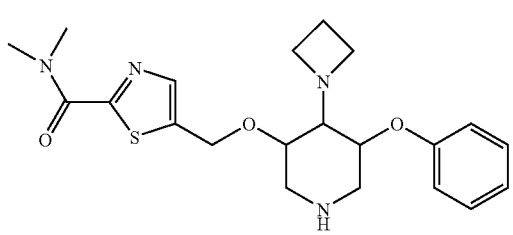

5-(4-Azetidin-1-yl-5-phenoxy-piperidn-3-yloxymethyl)-thiazole-2-carboxylic acid dimethylamide The invention encompasses compounds contemplated by Formula I, and more specifically those compounds shown below:

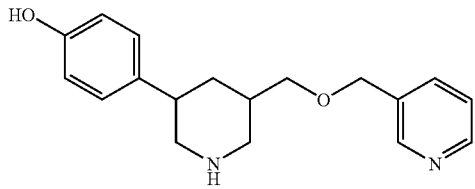

4-[5-(Pyridin-3-ylmethoxymethyl)-piperidin-3-yl]-phenol

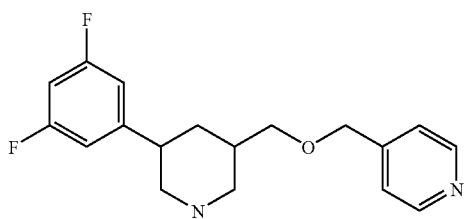

4-[5-(3,5-Difluoro-phenyl)-piperidin-3-ylmethoxymethyl]-pyridine

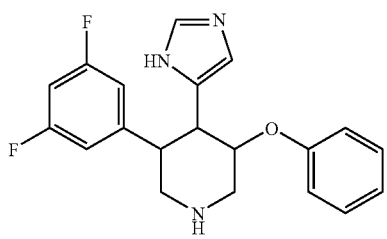

3-(3,5-Difluoro-phenyl)-4-(3H-imidazol)-4-yl)-5-phenoxy-piperidine

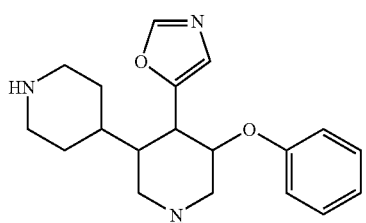

4-Oxazol-5-yl-5-phenoxy-[3,4']bipiperidinyl

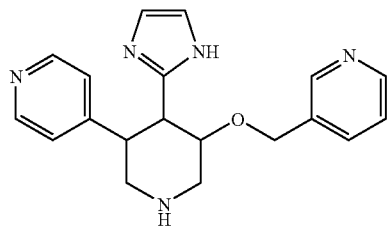

4-(1H-imidazol-2-yl)-5-(pyridin-3-yloxymethyl)-1,2,3,4,5,6-hexahydro-[3,4']bipyridinyl

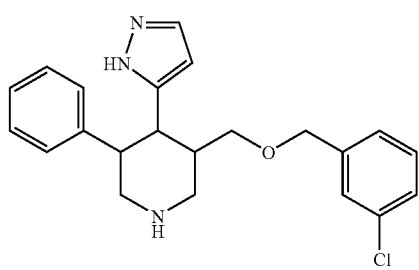

3-(3-Chloro-benzyloxymethyl)-5-phenyl-4-(2H-pyrazol-3-yl)-piperidine

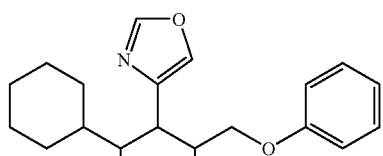

3-Cyclohexyl-4-oxazol-4-yl-5-phenoxymethyl-piperidine

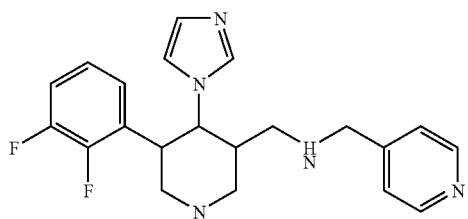

[5-(2,3-Difluoro-phenyl)-4-imidazol-1-yl-piperidin-3-ylmethyl]-pyridin-4-ylmethyl-amine The invention encompasses compounds contemplated by Formula II, and more specifically those compounds represented by:
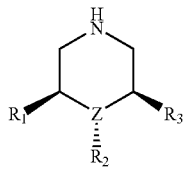
(II)
| $R_1 =$ | $R_2 =$ | $R_3 =$ |
|---|---|---|
| 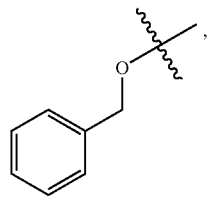 | H, 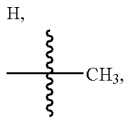 —CH$_3$, | 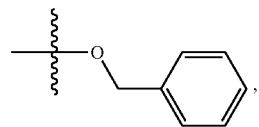 |
| 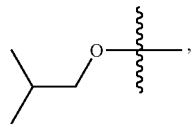 | 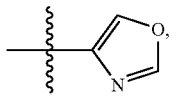 | 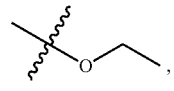 |
| 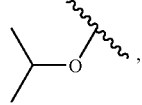 | 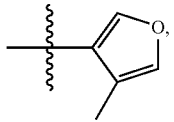 | 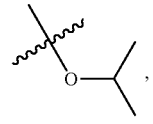 |
| 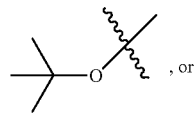, or | 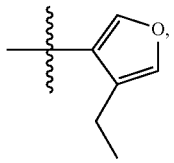 | 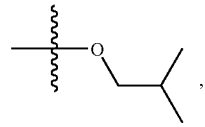 |
| 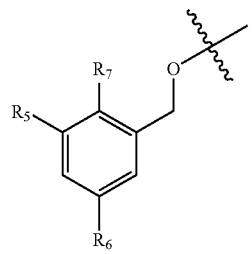 or 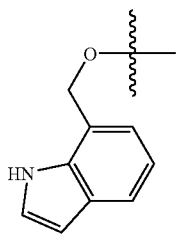 | 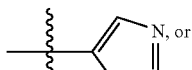 | 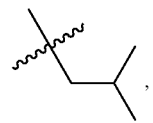 |
$R_6 =$ H, OH, NH$_2$
$R_4 =$ H, OH, NH$_2$, NHCH$_3$
$R_5 =$ H, OCH$_3$, CH$_2$CH$_2$OH
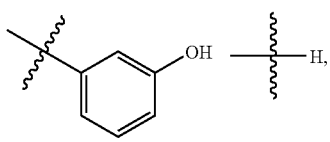
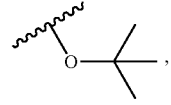

-continued

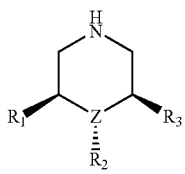
(II)

| $R_1 =$ | $R_2 =$ | $R_3 =$ |
|---|---|---|
|  |  | 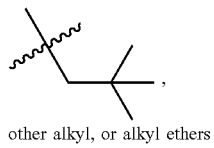 other alkyl, or alkyl ethers |

(wherein Z is CH or N)

The invention encompasses compounds contemplated by Formula I, and more specifically those compounds shown below:

The invention encompasses compounds contemplated by Formula I, and more specifically those preferred compounds shown below, where R in each compound may independently be $R_1$ or $R_3$, and wherein $R_1$, $R_2$, $R_3$ Z are as defined above.

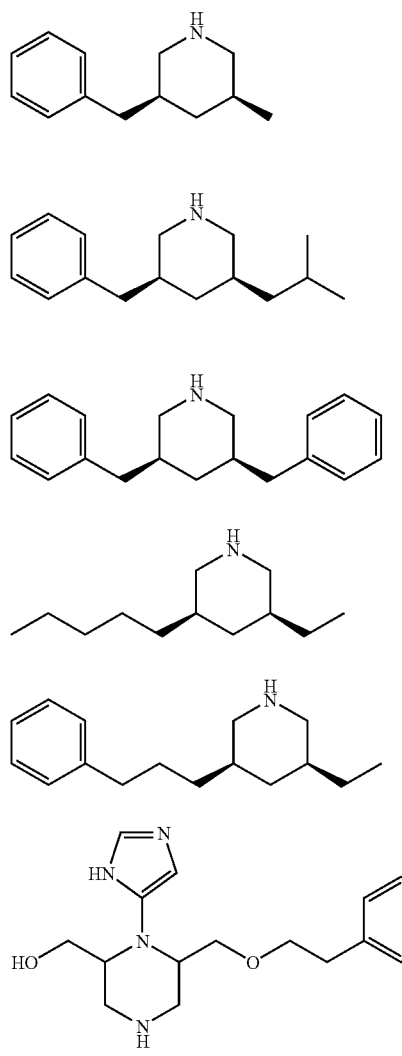

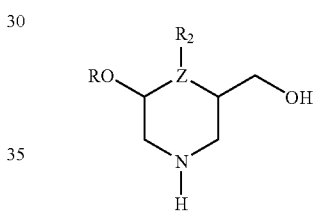

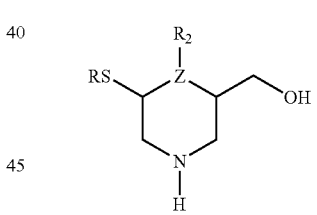

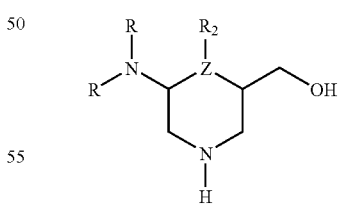

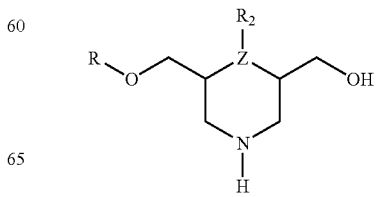

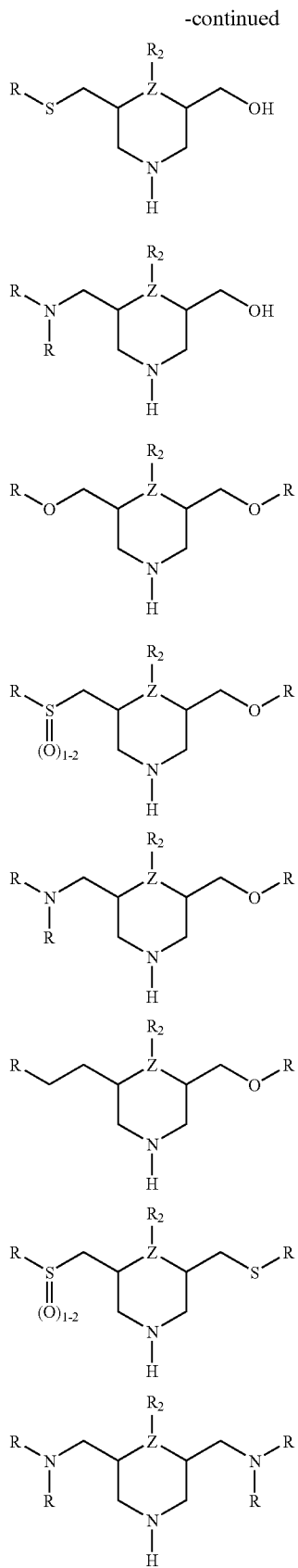

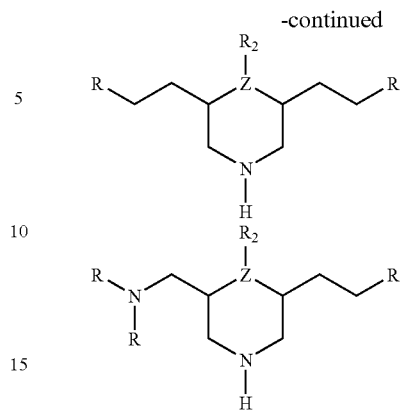

The invention encompasses compounds contemplated by Formula I, and more specifically those preferred $R_2$ groups as shown below. In another more preferred embodiement, $R_2$ is not a halogenated phenyl, benzyl, aryl or heteroaryl.

More preferred:
A substituted 5-membered heterocycle
(Carbon point of attachement)

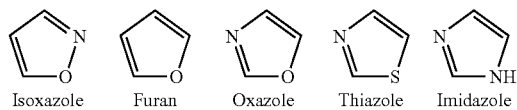

Isoxazole   Furan   Oxazole   Thiazole   Imidazole

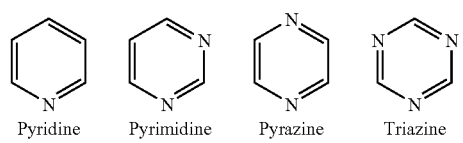

Pyrazole   Triazole

More preferred:
A substituted 6-membered heterocycle
(Carbon point of attachement)

Pyridine   Pyrimidine   Pyrazine   Triazine

More preferred:
A hydroxy substituted phenyl
(Carbon point of attachement)

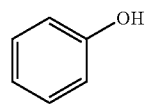

Where the aryl/heteroaryl substitution is "small"
Such as:
One or two, same or different:
Halogen (F, Cl, Br)
Substituted $C_1$-$C_3$ Alkyl (methyl, ethyl, trifluoromethyl ...)
Amino ($NH_2$)
$C_1$-$C_3$ Alkylamino (RHN——)
Cyano In yet another embodiment, the invention encompasses compounds contemplated by Formula I, and more specifically those preferred compounds as shown below. Possible substitutions off of the imidazole ring include aryl and alkyl groups.

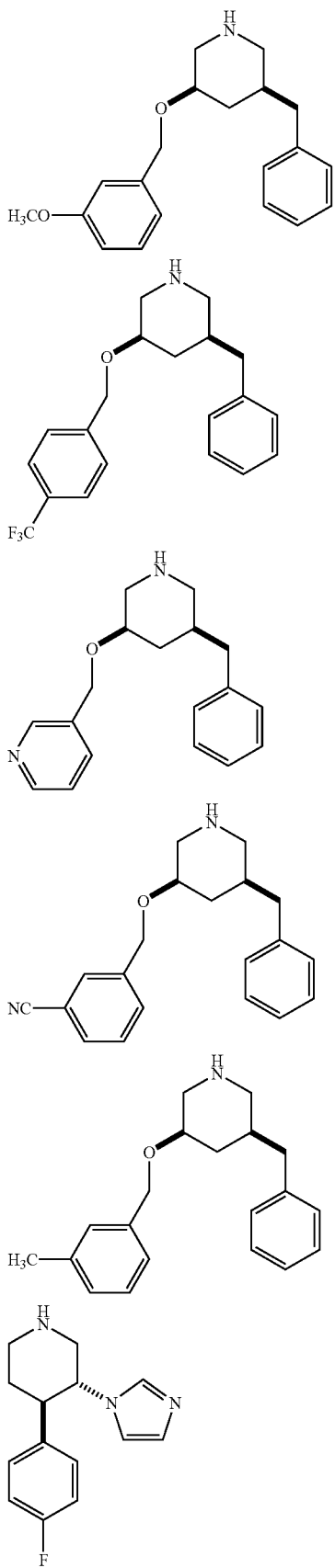
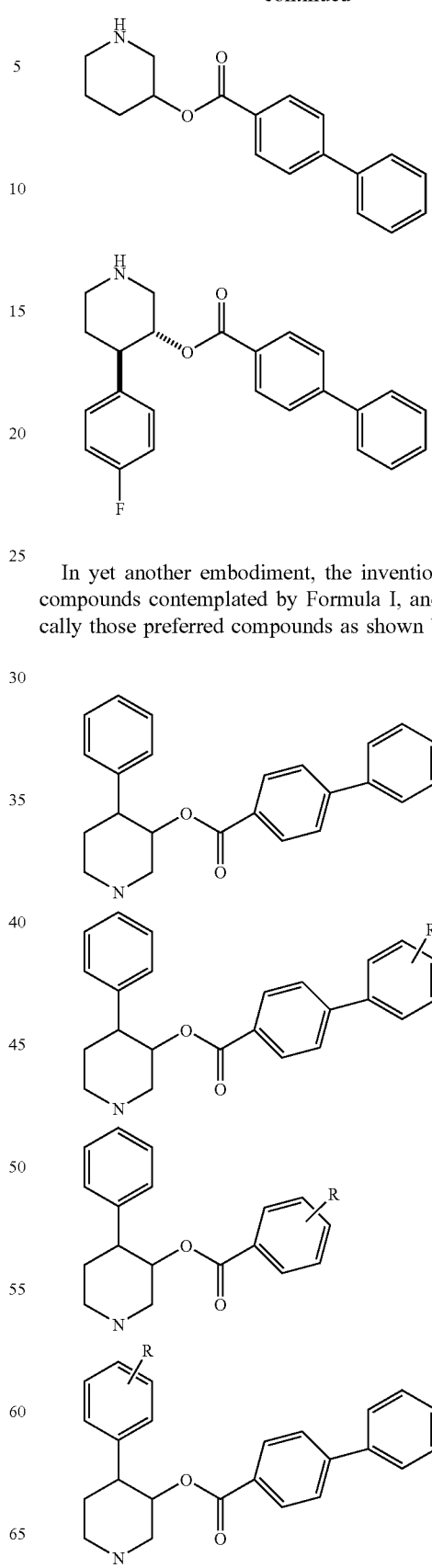
In yet another embodiment, the invention encompasses compounds contemplated by Formula I, and more specifically those preferred compounds as shown below.

-continued

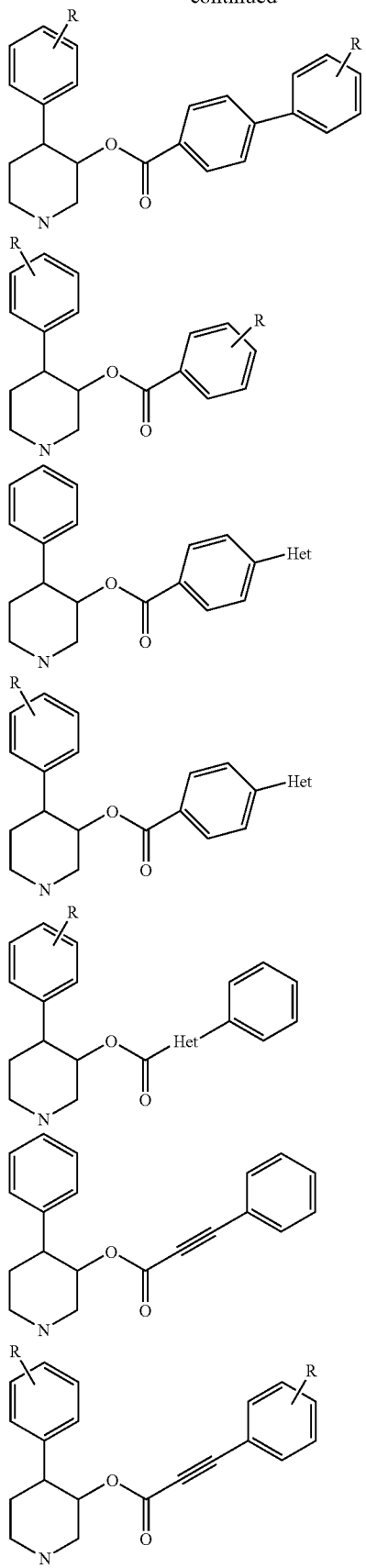

-continued

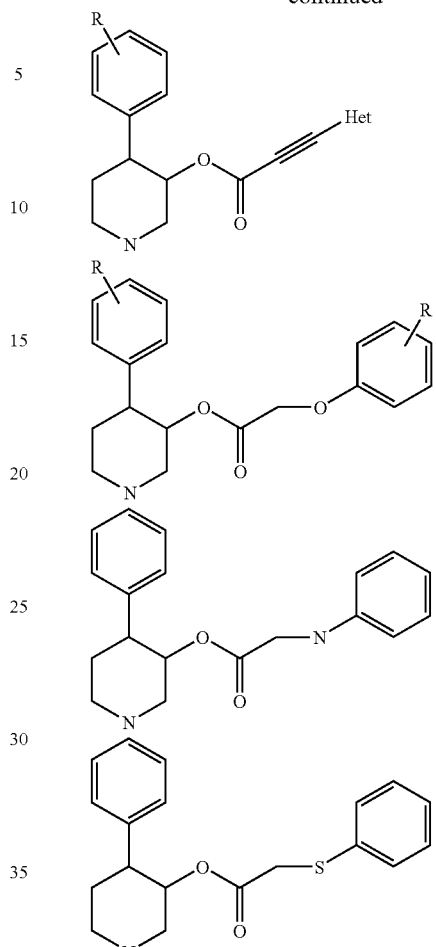

In another aspect, the invention provides compounds of the formula:

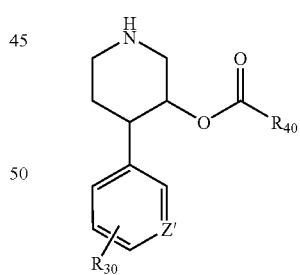

or a pharmaceutically acceptable salt or ester thereof,
wherein Z' is CH or N;
wherein $R_{30}$ is absent, —OH, or halo;
wherein $R_{40}$ is $C_{1-8}$ alkyl, $C_{1-8}$ alkoxy, aryl, substituted aryl, heteroaryl, substituted heteroaryl, heterocycl, substituted heterocycl, phenyl, substituted phenyl, $C_{1-8}$ alkyl-phenyl, or $C_{1-8}$ alkyl-substittued phenyl.

More preferably, $R_{30}$ is absent, —OH, or Cl, Br, I or F;
further $R_{40}$ is selected from the group consisting essentially of —CH$_3$, —CH$_2$CH$_2$-Ph-O—CH$_3$, -Ph-Ph-CO$_2$H, -Ph-Ph-OCH$_3$, -Ph-Ph-C(CH$_3$)$_3$, -Ph-Ph-OCF$_3$, -Ph-Ph-F, -Ph-C (=O)-Ph, -Ph-Ph-CN, -Ph-Ph-NH$_2$, -Ph-C(CH$_3$)$_3$, —CH(CH$_2$CH$_3$)(CH$_2$CH$_2$CH$_2$CH$_3$), —CH$_2$CH$_2$Ph, -Ph-O-Ph, naphthalene, -Ph-Ph-Cl, -Ph-(OCH$_3$)$_2$, —CH$_2$-Ph-OCH$_3$, —CH$_2$-Ph, -Ph-Ph-S(=O)$_2$CH$_3$, -Ph-Ph, pyridyl, Ph, Ph-I, -Ph-Ph-S—CH$_3$, -Ph-pyridyl, -Ph-NH$_2$, -Ph-NO$_2$, -Ph-CF$_3$, -Ph-CH$_3$, -Ph-Ph-CF$_3$, -Ph-Ph-(OCH$_3$)$_2$, -Ph-OCH$_3$, -Ph-CN, —CH$_2$—O-Ph, -Ph-OCF$_3$, —CH$_2$-PhF$_2$,

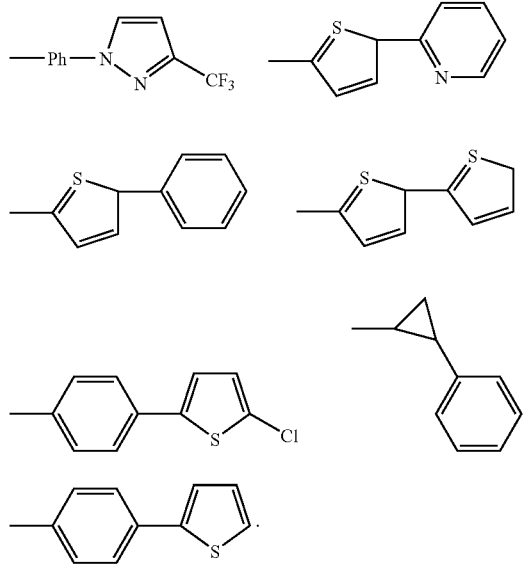

In a more preferred embodiement Z is CH. In accordance with this embodiment, a single substituent attached to a Ph-ring is in the ortho position; alternatively, a single substituent attached to a Ph-ring is in the meta position; also alternatively, a single substituent attached to a Ph-ring is in the para position. Further, di-substituents attached to a Ph-ring are in di-meta positions; alternatively, di-substituents attached to a Ph-ring are in a meta and para position.

In another aspect, the invention includes compounds of the formula

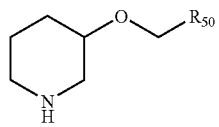

wherein R$_{50}$ is aryl or substituted aryl. More preferably, R$_{50}$ is selected form the group consisting of -Ph, -PhBr, -Ph-C(CH$_3$)$_3$, -PhF, -PhCl, -PhCN, napthyl, -Ph(CH$_3$)$_2$, -Ph-Ph, -Ph-I, -Ph-OCH$_3$, -PhCl$_2$, -Ph-PhCN, and -Ph-(OCH$_3$)$_2$. In accordance with this embodiment, a single substituent attached to a Ph-ring is in the ortho position; alternatively, a single substituent attached to a Ph-ring is in the meta position; also alternatively, a single substituent attached to a Ph-ring is in the para position. Further, di-substituents attached to a Ph-ring are in di-meta positions; alternatively, di-substituents attached to a Ph-ring are in a meta and para position.

In yet another embodiment, the invention includes compounds of the formula

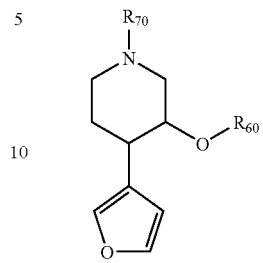

wherein R$_{60}$ is aryl, substituted aryl, C$_{1-6}$ alkyl, C$_{1-6}$ alkenyl, C$_{1-6}$ cycloalkyl, C$_{1-6}$ alkyl-C$_{1-6}$ cycloalkyl; and wherein R$_{70}$ is t-butoxycarbonyl or H. More preferably, R$_{60}$ is selected from the group consisting of -Ph, -Ph-Ph, napthyl, -Ph-O-Ph, -PhC(CH$_3$)$_3$, anthracinyl, -PhCH$_3$, -Ph(OCH$_3$)$_2$, -PhBr, -PhS(=O)$_2$CH$_3$, C(=CH$_2$)CH$_3$, cyclohexyl, —CH$_2$-cyclohexyl, —CH(CH$_3$)$_2$, and —CH(CH$_2$CH$_3$)$_2$. In accordance with this embodiment, a single substituent attached to a Ph-ring is in the ortho position; alternatively, a single substituent attached to a Ph-ring is in the meta position; also alternatively, a single substituent attached to a Ph-ring is in the para position. Further, di-substituents attached to a Ph-ring are in di-meta positions; alternatively, di-substituents attached to a Ph-ring are in a meta and para position.

The compounds of the present invention, and pharmaceutically acceptable salts or esters thereof, are useful for treating humans who have Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease. It is preferred that the disease is Alzheimer's disease.

The compounds of the present invention are also useful to inhibit beta-secretase and reduce or inhibit the formation of placque.

When treating these diseases, compounds of the present invention can either be used individually or together as is best for the patient.

With regard to these diseases the term "treating" means that compounds of the present invention can be used in humans with existing disease. The compounds of the present invention will not necessarily cure the patient who has the disease but will delay or slow the progression of the disease thereby giving the individual a more useful life span.

The term "preventing" means that that if the compounds of the present invention are administered to those who do not now have the disease but who would normally get the disease or be at increased risk for the disease, they will not get the disease. In addition, "preventing" also includes delaying the development of the disease in an individual who will ultimately get the disease or would be at risk for the disease. By delaying the onset of the disease, compounds of the present invention have prevented the individual from getting the disease during the period in which the individual would normally have gotten the disease or reduce the rate of development of the disease or some of its effects but for the administration of compounds of the present invention up to the time the individual ultimately gets the disease.

In treating or preventing the above diseases the compounds of the present invention are administered in a therapeutically effective amount. The therapeutically effective amount will vary depending on the particular compound used and the route of administration as is known to those skilled in the art.

In treating a patient with any of the diagnosed above conditions a physician should begin administration of one or more of the compounds of the present invention immediately and continue indefinitely.

In treating patients who do not at the present have Alzheimer's disease, but who are believed to be at substantial risk for getting Alzheimer's disease in the future, the physician should start treatment when the patient first experiences early pre-Alzheimer's symptoms such as, memory or cognitive problems associated with aging. In addition, there are some patients who are at high risk because of having the genetic marker APOE4 which is predictive for Alzheimer's disease. In these situations, even though the patient does not have the disease, the administration of the compounds of the present invention should be started before disease symptoms appear and treatment continued indefinitely to prevent or delay them from possibly getting the disease.

The compounds of the present invention can be administered orally, parenterally (IV, IM, depo-IM, SQ and depo-SQ), sublingually, intranasally (inhalation), intrathecally, topically and rectally. The invention here is the compounds of the present invention. There is nothing new about the routes of administration nor the dosage forms. Dosage forms known to those skilled in the art are suitable for delivery of the compounds of the present invention.

When administered orally, the compounds of the present invention can be administered in usual dosage forms for oral administration as is well known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the compounds of the present invention need to be administered only once or twice daily.

The oral dosage forms are administered to the patient one thru four times daily. It is preferred that the compounds of the present invention be administered either three or fewer time, more preferably once or twice daily. Hence, it is preferred that the compounds of the present invention be administered in solid dosage form and further it is preferred that the solid dosage form be a sustained release form which permits once or twice daily dosing. It is preferred that whatever dosage form is used, that it be designed so as to protect the compounds of the present invention from the acidic environment of the stomach. Enteric coated tablets are well known to those skilled in the art. In addition, capsules filled with small spheres each coated to protect from the acidic stomach, are also well known to those skilled in the art. When administered orally the therapeutically effective amount is from about 0.1 mg/day to about 3,000 mg/day, preferably about 1,000 mg/day. It is more preferred that the oral dosage is from about 1 mg/day to about 100 mg/day. It is more preferred that the oral dosage is from about 5 mg/day to about 50 mg/day. It is understood that while a patient may be started on one dose, that dose may have to be varied over time as the patient's condition changes.

In addition, the compounds of the present invention can be administered parenterally. When administered parenterally they can be administered IV, IM, depo-IM, SQ or depo-SQ. When administered parenterally, the compounds of the present invention should deliver a therapeutically effective amount about 0.5 to about 100 mg/day, preferably from about 5 to about 50 mg daily. When a depo formulation is used for injection once a month or once every two weeks, the dose should be about 0.5 mg/day to about 50 mg/day or on a monthly amount the dose for one month should be from about 15 mg to about 1,500 mg. Because of the forgetfulness of the patients with Alzheimer's disease, it is preferred that the parenteral dosage form be a depo-IM injection.

The compounds of the present invention can be given sublingually. When given sublingually, the compounds of the present invention should be given one thru four times daily in the same amount as for IM administration.

The compounds of the present invention can be given intranasally. When given by this route of administration, the appropriate dosage forms are a nasal spray or dry powder as is known to those skilled in the art. The dosage of the compounds of the present invention for intranasal administration is the same as for IM administration.

The compounds of the present invention can be given intrathecally. When given by this route of administration the appropriate dosage form can be a parenteral dosage form as is known to those skilled in the art. The dosage of the compounds of the present invention for intrathecal administration is the same as for IM administration.

The compounds of the present invention can be given topically. When given by this route of administration, the appropriate dosage form is a cream, ointment or patch. Because of the amount of the compounds of the present invention needed to administered the patch is preferred. Further, two or more patches may be needed. When administered topically, the dosage is from about 0.5 mg/day to about 200 mg/day. However, the amount that can be delivered by a patch is limited. Therefore, two or more patches may be required. The number and size of the patch is not important, what is important is that a therapeutically effective amount of the compounds of the present invention be delivered as is known to those skilled in the art. The compounds of the present invention can be administered rectally by suppository as is known to those skilled in the art. When administered by suppository, the therapeutically effective amount is from about 0.5 mg to about 500 mg.

The compounds of the present invention can be administered by implants as is known to those skilled in the art. When administering a compound of the present invention by implant, the therapeutically effective amount is the same as for depot administration.

Again, the invention here is the compounds of the present invention of the present invention. There is nothing novel about the route of administration nor the dosage forms for administering the compounds of the present invention. Given a particular compounds of the present invention, and a desired dosage form, one skilled in the art would know how to prepare the appropriate dosage form for the compounds of the present invention.

The compounds of the present invention are used in the same manner by the same routes of administration using the same pharmaceutical dosage forms and at the same dosing schedule for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease.

The compounds of the present invention can be used with each other or with other agents used to treat or prevent the conditions listed above. Such agents include gamma-secretase inhibitors, anti-amyloid vaccines and pharmaceutical agents such as donepezil hydrochloride (ARICEPT Tablets), tacrine hydrochloride (COGNEX Capsules) or other acetylcholine esterase inhibitors and with direct or indirect neurotropic agents of the future.

In addition, the compounds of the present invention can also be used with inhibitors of P-glycoproten (P-gp). The use of P-gp inhibitors is known to those skilled in the art. See for example, Cancer Research, 53, 4595-4602 (1993), Clin. Cancer Res., 2, 7-12 (1996), Cancer Research, 56, 4171-4179 (1996), International Publications WO99/64001 and WO01/10387. The important thing is that the blood level of the P-gp inhibitor be such that it exerts its effect in inhibiting P-gp from decreasing brain blood levels of the compounds of the present invention. To that end the P-gp inhibitor and the compounds of the present invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,1 1-methanodibenzosuberane, phenothiazines, acridine derivatives such as GF120918, FK506, VX-710, LY335979, PSC-833, GF-102, 918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant. The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect From the acidic stomach, are also well known to those skilled in the art.

In addition, the P-gp inhibitors can be administered parenterally. When administered parenterally they can be administered IV, IM, depo-IM, SQ or depo-SQ. The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration nor the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the present invention administered, the particular condition being treated, the severity of the condition being treated, the age, weight, general physical condition of the particular patient, other medication the individual may be taking as is well known to those skilled in the art.

The compounds of the present invention are also useful to inhibit beta-secretase and reduce or inhibit the formation of plaque.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site". While not wishing to be bound by a particular theory, inhibition of beta-secretase activity is thought to inhibit production of beta amyloid peptide (A-beta or Abeta). Inhibitory activity is demonstrated in one of a variety of inhibition assays, whereby cleavage of an APP substrate in the presence of A-beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the examples below.

The enzymatic activity of beta-secretase and the production of Abeta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Mol. Cell. Neurosci. 14:419-427 (1999); Science 286:735-741 (1999); Nature 402:533-537 (1999); Nature 40:537-540 (1999); and PNAS USA 97:1456-1460 (2000)). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than about 50 micromolar, preferably at a concentration of less than about 10 micromolar, more preferably less than about 1 micromolar, and most preferably less than about 10 nanomolar.

APP Substrate

Assays that demonstrate inhibition of beta-secretase-mediated cleavage of APP can utilize any of the known forms of APP, including the 695 amino acid "normal" isotype described in Nature 325:733-6 (1987), the 770 amino acid isotype described Nature 331:530-532 (1981), and variants such as the Swedish Mutation (KM670-1NL) (APP-SW), the London Mutation (V7176F), and others. See, for example U.S. Pat. No. 5,766,846 and also Nature Genet. 1:233-234 (1992), for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful forenzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Neuro. Lett. 249:21-4 (1999) and in U.S. Pat. No. 5,612,486. Useful antibodies to detect Abeta include, for example, the monoclonal antibody 6E10 (Senetek, St. Louis, Mo.) that specifically recognizes an epitope on amino acids 1-16 of the Abeta peptide; antibodies 162 and 164 (New York State Institute for Basic Research, Staten Island, N.Y.) that are specific for human A-beta 1-40 and 1-42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590-596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. No. 5,744,346 and 5,942,400, and described in the EXAMPLES below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing A-beta-secretase and an APP substrate having A-beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4-7, at approximately 37° C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A-beta. Contact of an APP substrate with A-beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process Abeta from APP provide a useful means to assay inhibitory activities of the compounds of the invention. Production and release of A-beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as Abeta.

Although both neural and non-neural cells process and release A-beta, levels of endogenous beta-secretase activity are low and often difficult to detect by EIA. The use of cell types known to have enhanced beta-secretase activity, enhanced processing of APP to Abeta, and/or enhanced production of A-beta are therefore preferred. For example, transfection of cells with the Swedish Mutant form of APP (APP-SW); with APP-KK; or with APP-SW-KK provides cells having enhanced beta-secretase activity and producing amounts of A-beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of Abeta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release Abeta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399, 5,612, 486, 5,387,742, 5,720,936, 5,850,003, 5,877,015 and 5,8114,633, and Nature 373:523 (1995)). Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of Abeta release can be analyzed in these animals by measure of cleavage fragments in the animal's body fluids such as cerebral fluid or tissues. Analysis of brain tissues for Abeta deposits or plaques is preferred.

On contacting an APP substrate with A-beta-secretase enzyme in the presence of an inhibitory compound of the invention and under conditions sufficient to permit enzymatic mediated cleavage of APP and/or release of Abeta from the substrate, the compounds of the invention are effective to reduce beta-secretase-mediated cleavage of APP at the beta-secretase cleavage site and/or effective to reduce released amounts of Abeta. Where such contacting is the administration of the inhibitory compounds of the invention to an animal model, for example, as described above, the compounds are effective to reduce Abeta deposition in brain tissues of the animal, and to reduce the number and/or size of beta amyloid plaques. Where such administration is to a human subject, the compounds are effective to inhibit or slow the progression of disease characterized by enhanced amounts of Abeta to slow the progression of AD in the, and/or to prevent onset or development of AD in a patient at risk for the disease.

Unless defined otherwise, all scientific and technical terms used herein have the same meaning as commonly understood by one of skill in the art to which this invention belongs.

Definitions and Conventions

The definitions and explanations below are for the terms as used throughout this entire document including both the specification and the claims.

Definitions

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

AD refers to Alzheimer's disease.

APP, amyloid precursor protein, is defined as any APP polypeptide, including APP variants, mutations, and isoforms, for example, as disclosed in U.S. Pat. No. 5,766,846.

A-beta (or Abeta), amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (beta-secretase, BACE1, Asp2, Memapsin 2) is an aspartyl protease that mediates cleavage of APP at the amino-terminal edge of Abeta. Human beta-secretase is described, for example, in WO0/17369.

DMSO refers to dimethyl sulfoxide.

All temperatures are in degrees Centigrade.

HPLC refers to high pressure liquid chromatography.

BOC refers to 1,1-dimethylethoxy carbonyl or t-butoxycarbonyl, —CO—O—C(CH$_3$)$_3$.

Protecting group refers to t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcycoopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobrornyloxycarbonyl and 1-piperidyloxycarbonyl, 9-fluoroenylmethyl carbonate, —CH—CH=CH$_2$ and phenyl-C(=N—)—H.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

Pharmaceutically acceptable refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs. All patents and publications referred to herein are hereby incorporated by reference for all purposes.

By "alkyl" and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons.

By "alkoxy" and "$C_1$-$C_6$ alkoxy" in the present invention is meant straight or branched chain alkyl groups having 1-6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$-$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$-$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)

alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$) alkylamino ($C_1$-$C_6$) alkyl.

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. For example, such heteroaryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$) alkylamino ($C_1$-$C_6$) alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino ($C_1$-$C_6$)alkyl, di($C_1$-$C_6$)alkylamino($C_1$-$C_6$)alkyl or =O.

Modes of Preparation

Compounds of the invention can be prepared utilizing a variety of known chemical transformations. The compounds of the invention can be prepared by one skilled in the art without more just by knowing the chemical structure of the compound. The chemistry is known to those skilled in the art. In fact, there is more than one process to prepare the compounds of the invention. Exemplary methods of preparation can be found in the art. For example, see *A Short Formal Synthesis of Paroxetine. Diastereoselective Cuprate Addition of a Chiral Racemic Olefinic Amido Ester*, Coss, J., et al., Tetrahedron Letters, 42 (2001, 7805-7807; *Solid-Phase Synthesis of Aspartic Peptidas Inhibiors: 3-Alkoxy-4-Aryl Piperidines*, Bursavich, Matthew, et. al., Organic Letters, 2001, Vol. 3, No. 17, 2625-2628; and *From Peptides to Non-Peptide Peptidomimetics: Design and Synthesis of New Piperidine Inhibitors of Aspartic Peptidases*, Bursavich, Matthew, et. al., Organic Letters, 2001, Vol. 3, No. 15, 2317-2320; and the references cited therein, all incorporated in by the entirety.

In addition to the methods above, a variety of additional synthetic routes may be utilized to prepare the compounds of the invention as shown in more detail below. Representative procedures for the preparation of compounds are set forth below in the various schemes. The R-groups shown in the schemes are generally representative of $R_1$, $R_2$, $R_3$, and $R_4$ as set forth herein.

Synthetic Routes to 3,5-Disubstituted-piperidines

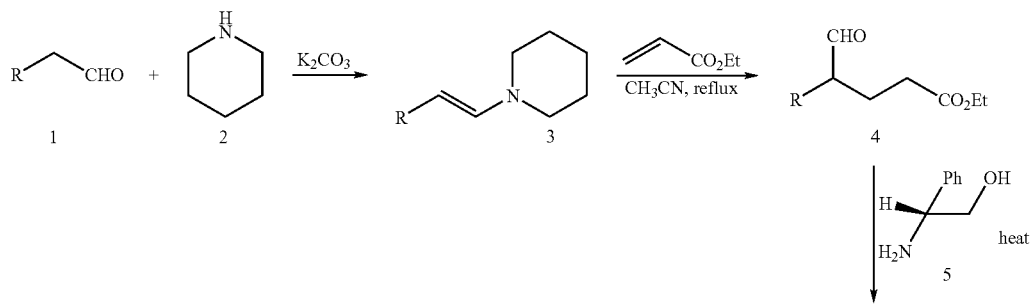

Scheme 1

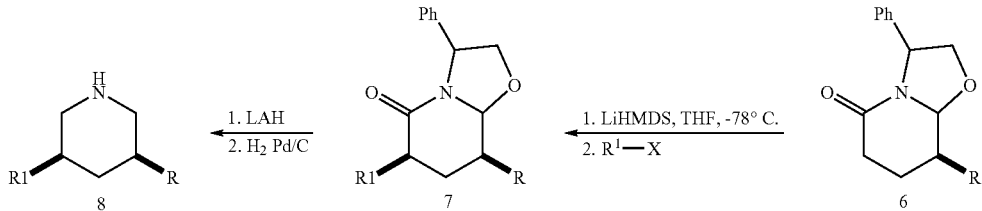

Any enolizable aldehyde capable of forming an enamine should react to form 3, leading to a wide variety of substituents which end up at C-3. R can be alkyl chain of 1-6 carbons, straight-chained or branched, cycloalkylmethyl, phenylmethyl, or phenyl-substituted alkyl chain of 1-6 carbons, either straight-chained or branched. Both enantiomers of 5, commercially available, which can therefore give rise to both enantiomers of 6. $R^1$ can be the same or different as R, defined above, where X is a "good leaving" group such as, Br, Cl, I, Tosly, Mesyl, etc. Other electrophilic reagents such as acid chlorides, sulfonyl chlorides, chloroformates and also make up $R^1$—X.

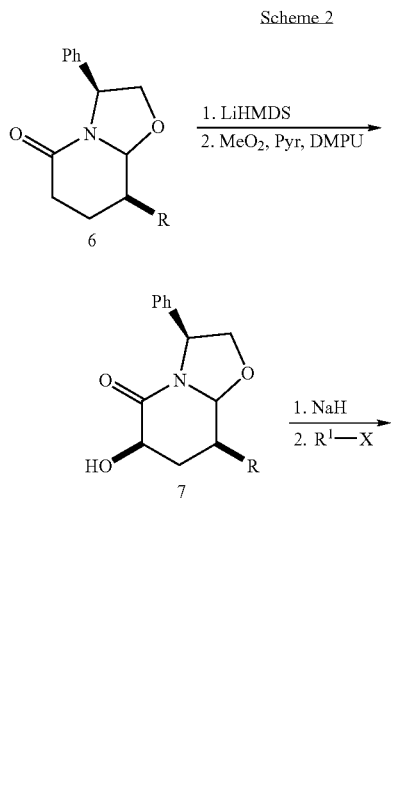

There are numerous ways to introduce and oxygen a to the amide carbonyl. Only one such method is shown. R is defined as above. $R^1$—X defined as above.

Synthetic Routes to 3,4-disubstituted and 3,4,5-trisubstituted piperidines

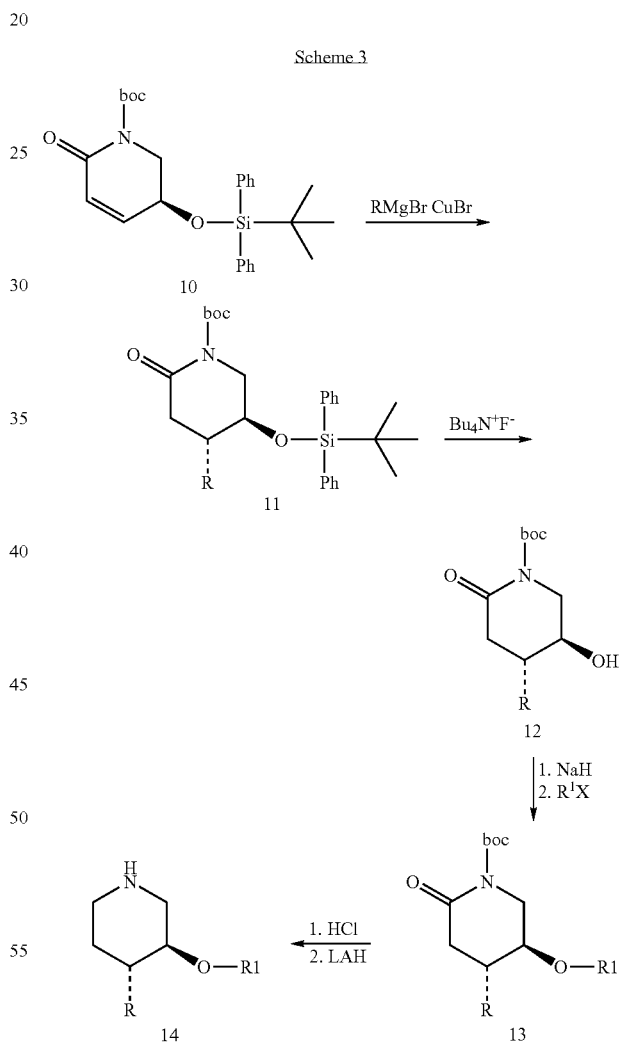

Compound 10 is known in the literature (Tet. Asymm, 1996, 7, 867). R is defined as above, with the addition of being phenyl, substituted phenyl, heteroaromatic rings, cycloalkyl rings, or substituted cycloalkyl rings of 3-8 members. The reaction sequence will also work if alkyl lithium cuprates are substituted for the Grignard reagent, RMgBr.

Scheme 4

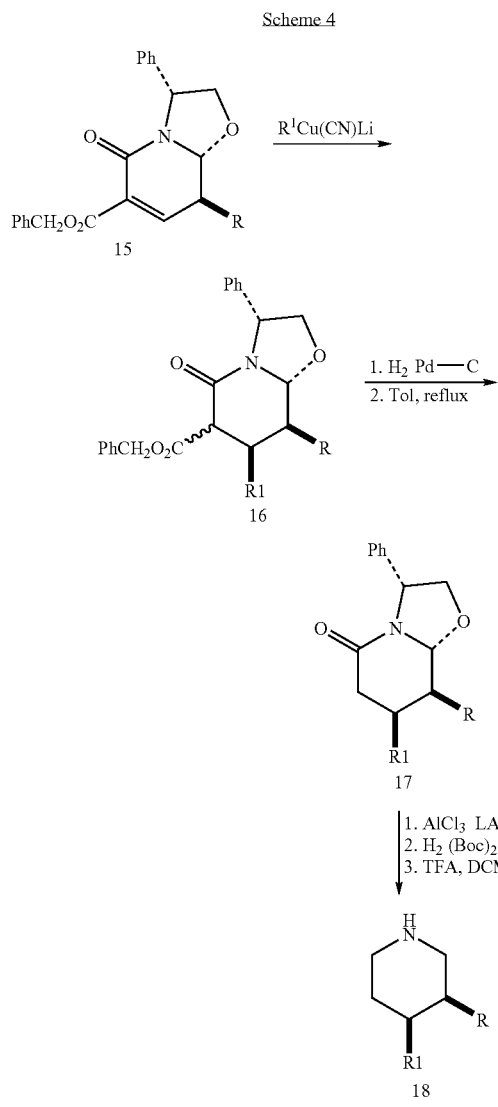

Compound 15 is known in the literature where R-Ethyl (Org Lett, 2001, 3, 611). It can be prepared readily from 6, where R is defined as above. $R^1$ can be the same as or different from R and defined as above. R is defined as above, with the addition of being phenyl, substituted phenyl, heteroaromatic rings, cycloalkyl rings, or substituted cycloalkyl rings of 3-8 members.

Scheme 5

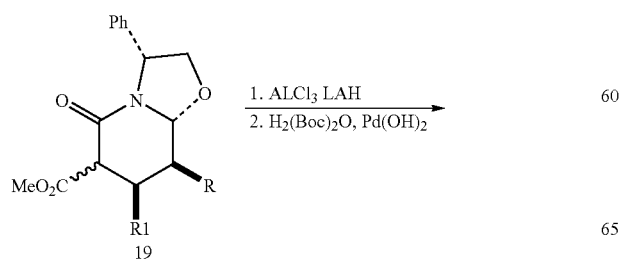

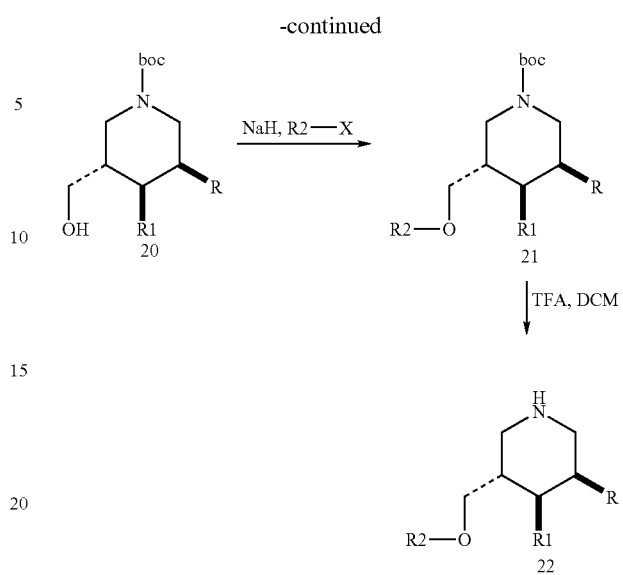

Compound 19 can be prepared analogously to 16 above. R and R1 are defined above. R2 can be the same or different as R or R1.

Scheme 6

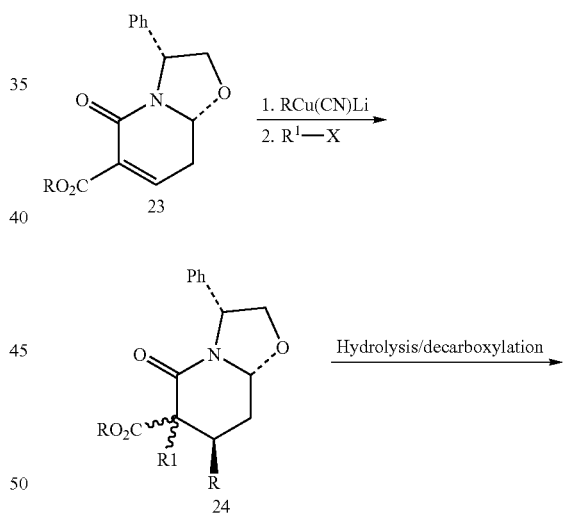

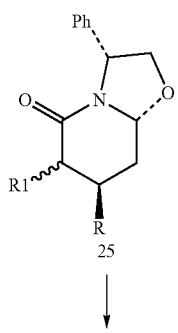

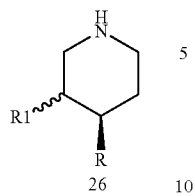
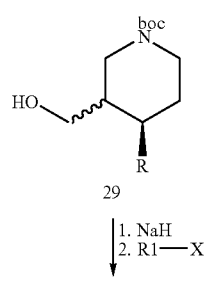
Scheme 7
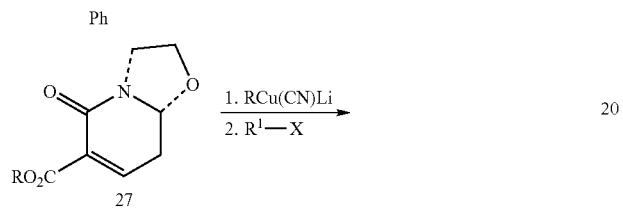
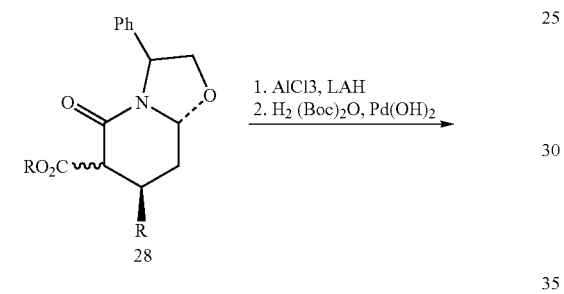
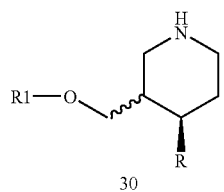
Scheme 8
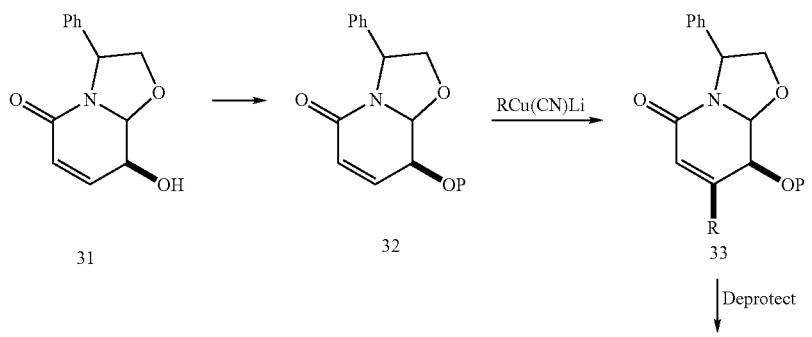
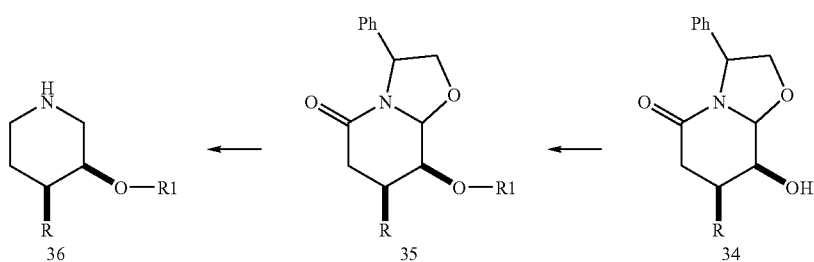

Complimentary Methods of Piperidine Synthesis:

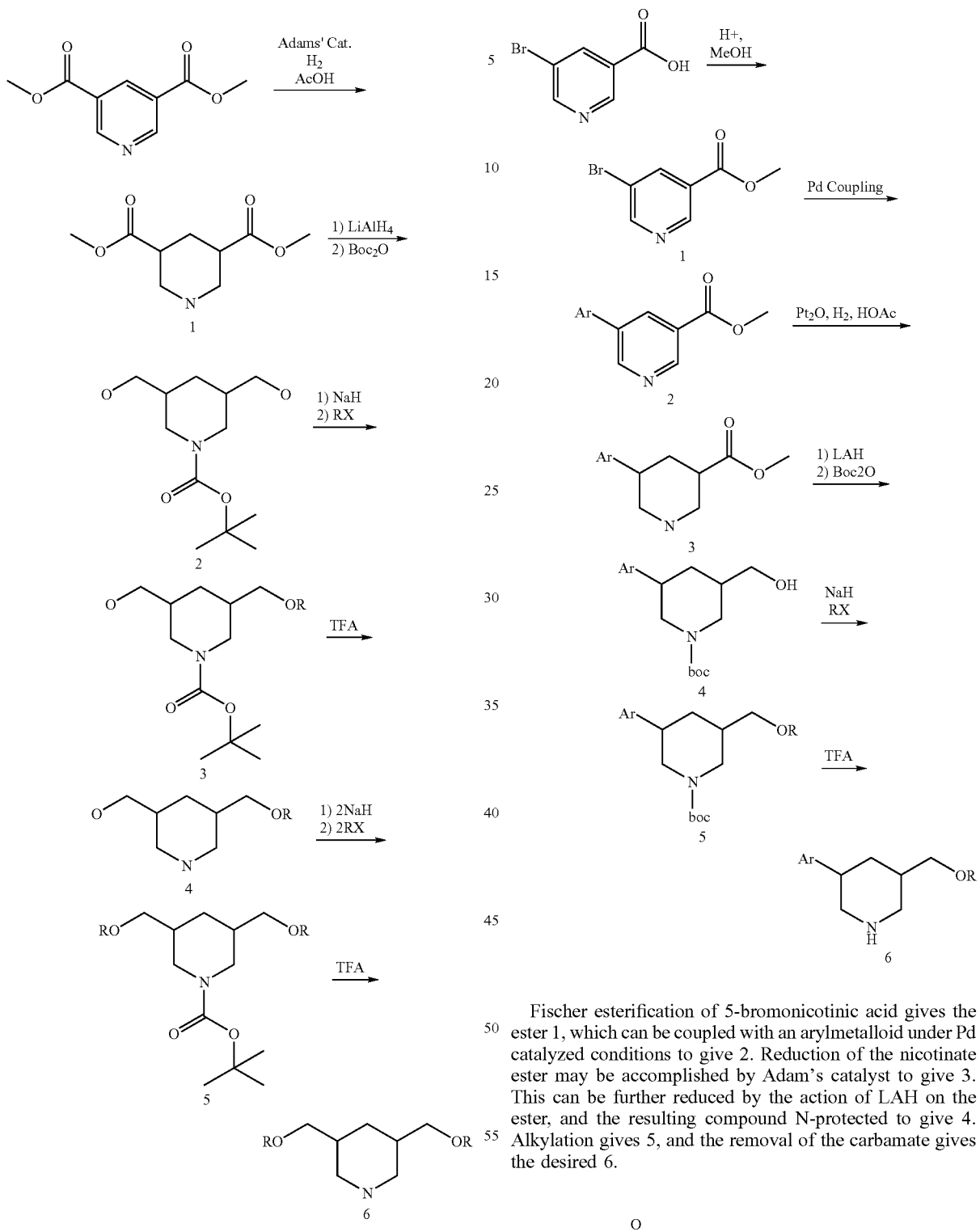

Fischer esterification of 5-bromonicotinic acid gives the ester 1, which can be coupled with an arylmetalloid under Pd catalyzed conditions to give 2. Reduction of the nicotinate ester may be accomplished by Adam's catalyst to give 3. This can be further reduced by the action of LAH on the ester, and the resulting compound N-protected to give 4. Alkylation gives 5, and the removal of the carbamate gives the desired 6.

Dimethyldinicotinate is hydrogenated over Adam's catalyst in AcOH to give the piperidine 1. The esters are then reduced by LAH, then protected with Boc anhydride to give the diol 2, which is alkylated under Williamson-type conditions to give either mono-alkyl 3. or bis-alkyl 4. Removal of the Boc group yields the final compound.

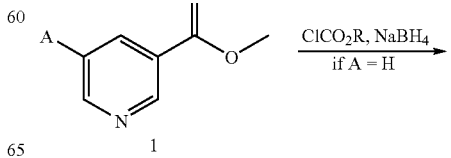

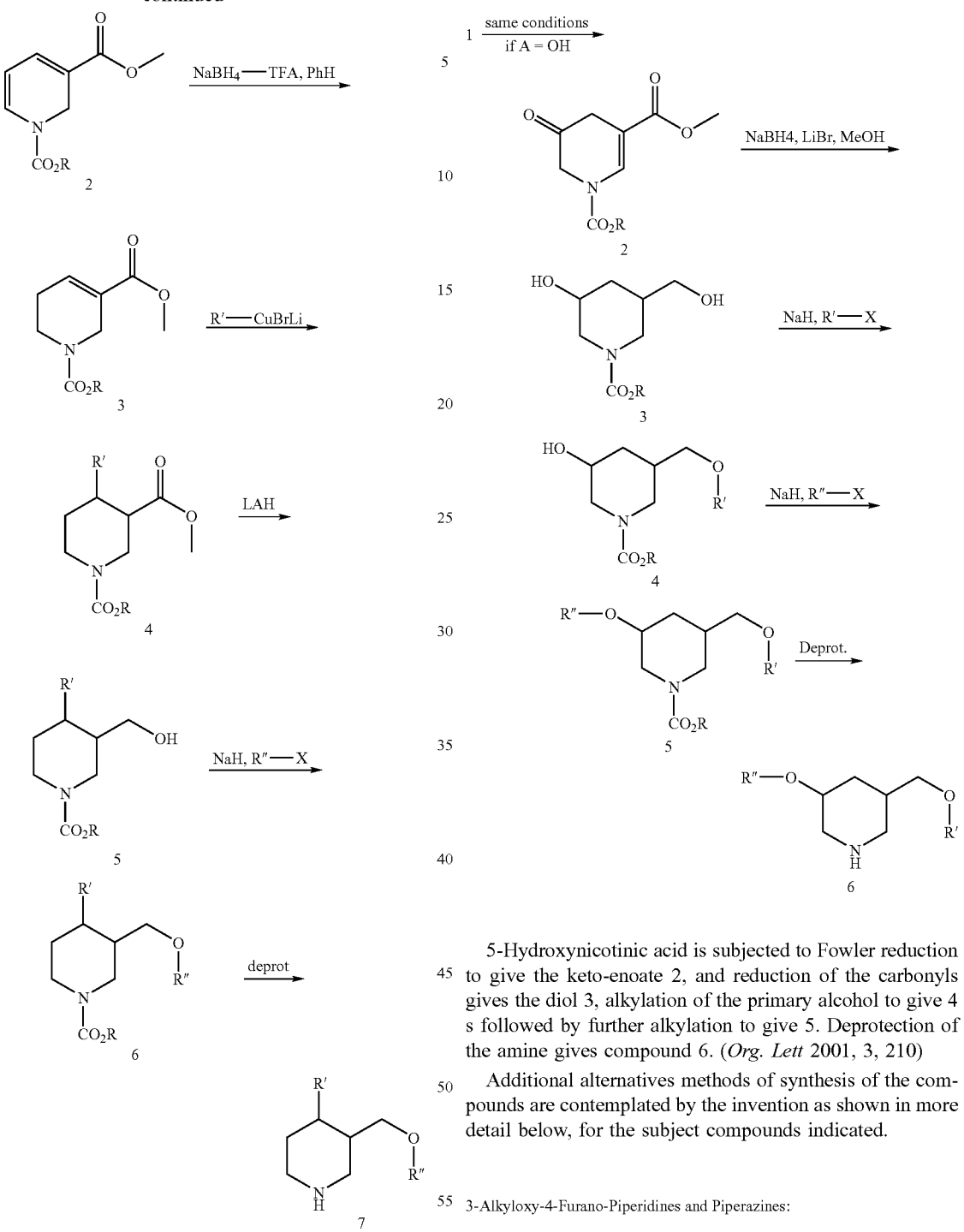

Nicotinic acid, 1, is subjected to a Fowler reduction, giving compound 2. Further reduction gives the enoate 3. Addition of an alkyl cuprate will substitute the 4 position of the piperidine to give 4 (if H is desired, Rh catalyzed hydogenation is used), the ester of which can be reduced by LAH to give the primary alcohol, 5. The alcohol can be alkylated to give 6, and the amine deprotected to give 7. (*Org. Lett.*, 2001, 3, 210)

5-Hydroxynicotinic acid is subjected to Fowler reduction to give the keto-enoate 2, and reduction of the carbonyls gives the diol 3, alkylation of the primary alcohol to give 4 followed by further alkylation to give 5. Deprotection of the amine gives compound 6. (*Org. Lett* 2001, 3, 210)

Additional alternatives methods of synthesis of the compounds are contemplated by the invention as shown in more detail below, for the subject compounds indicated.

3-Alkyloxy-4-Furano-Piperidines and Piperazines:

-continued
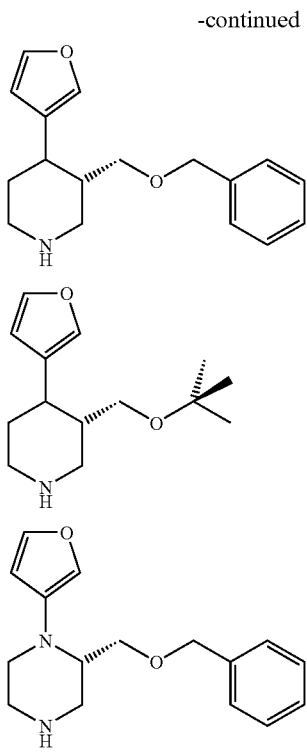
Synthetic Routes:
1.
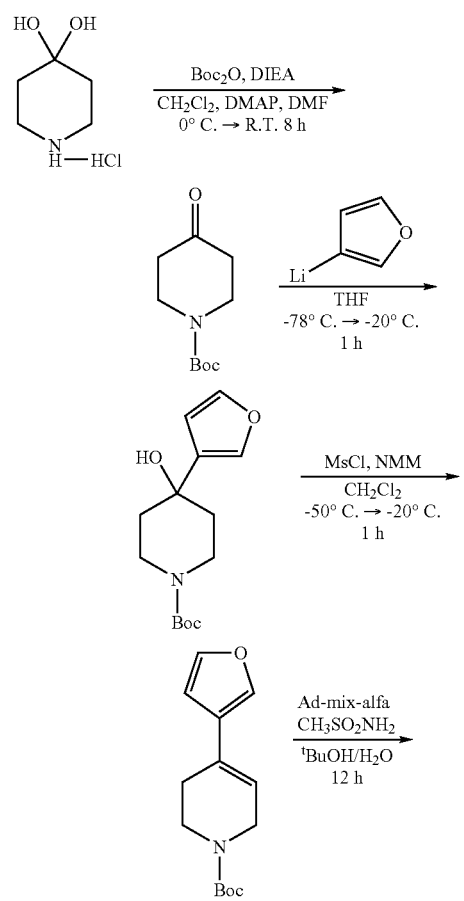
-continued
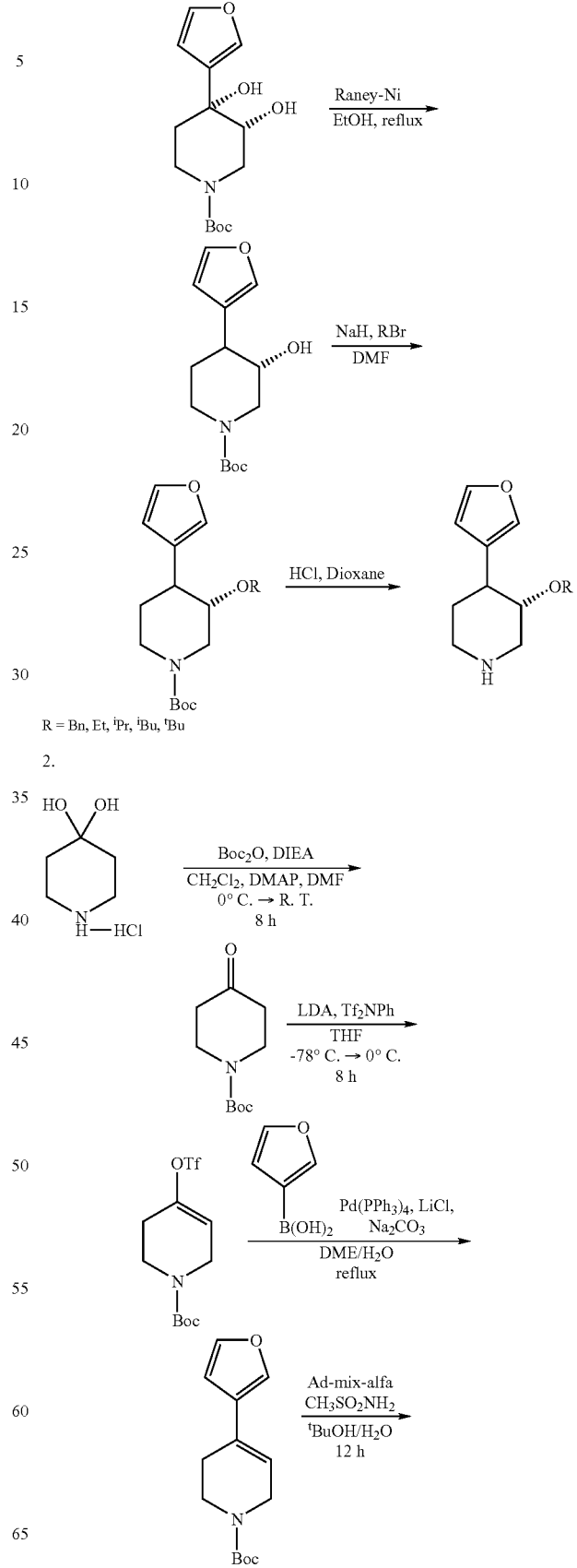
R = Bn, Et, $^i$Pr, $^i$Bu, $^t$Bu
2.

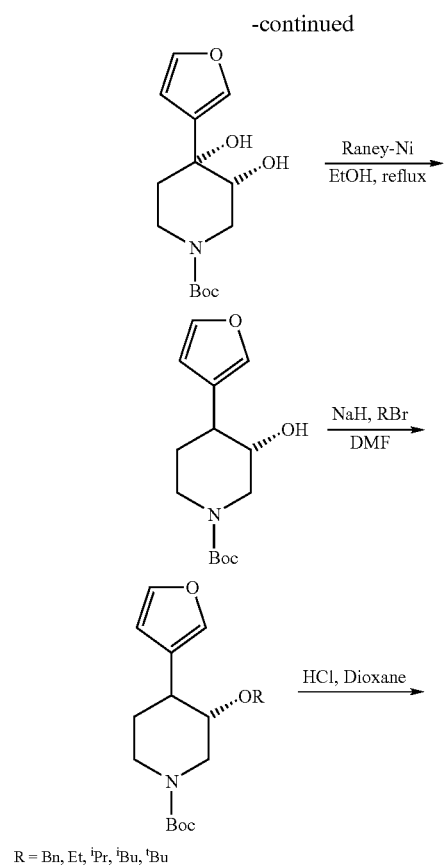
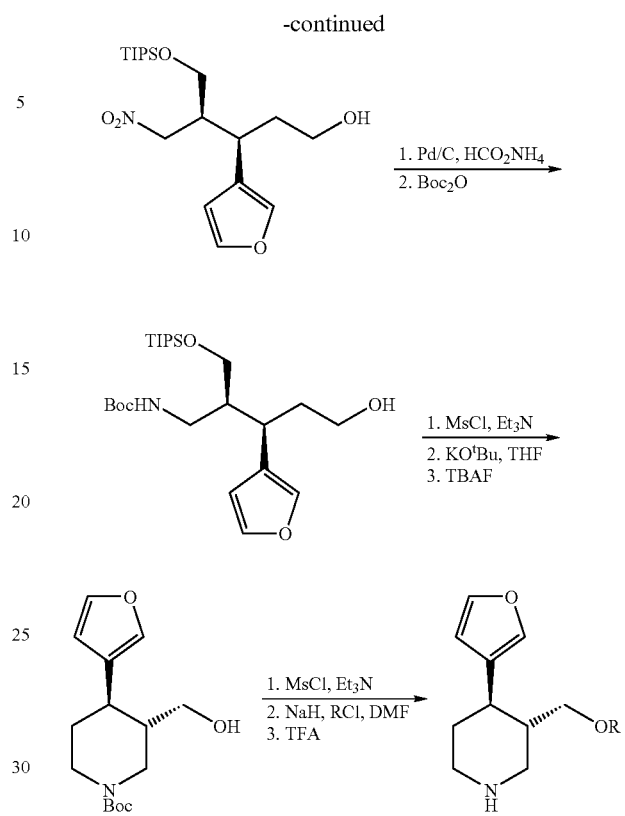
3-Alkyloxy-4-Isoxazolo-Piperidines
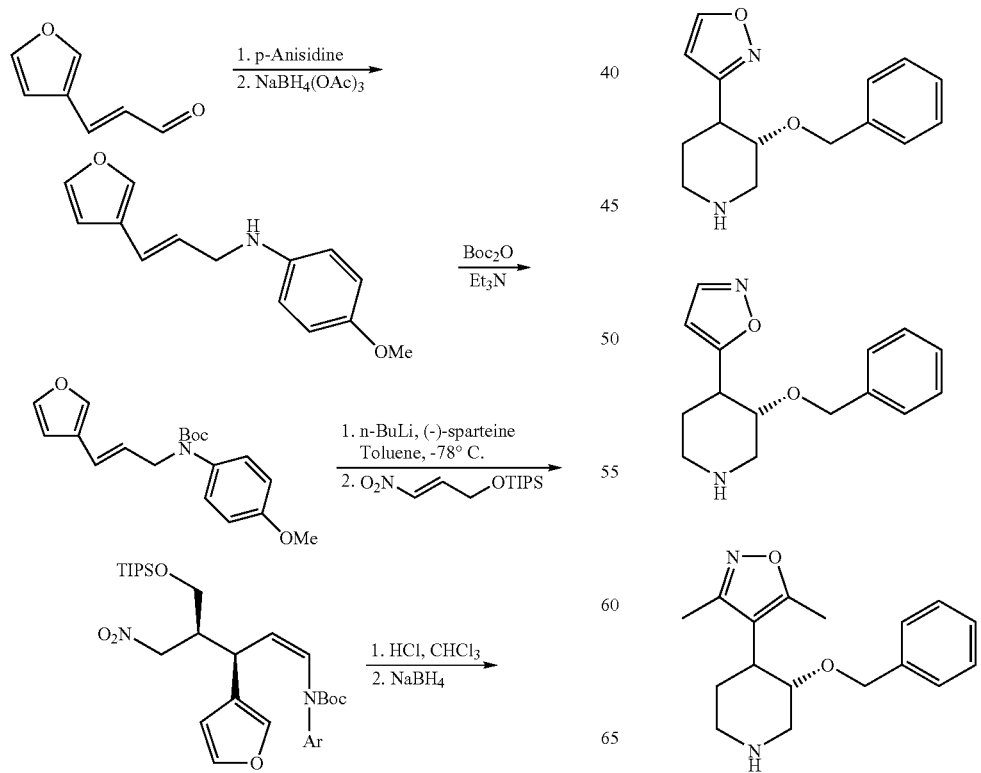

-continued
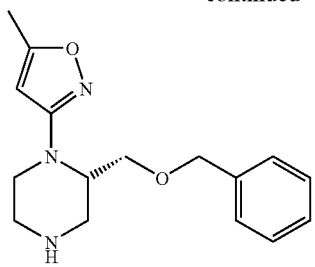
Synthetic Routes:
1.
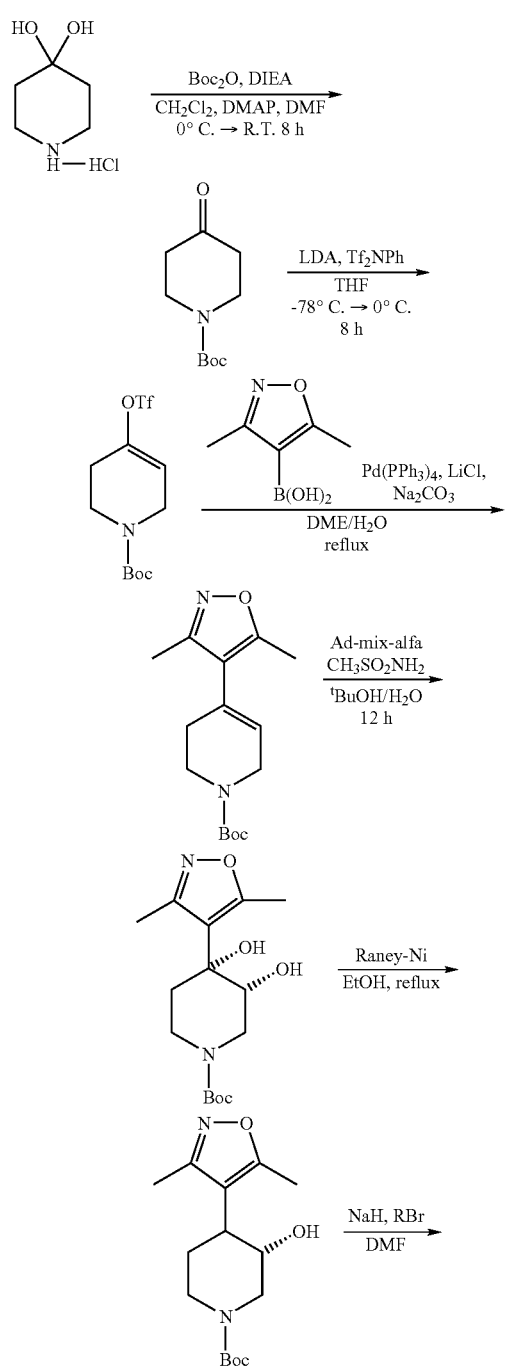
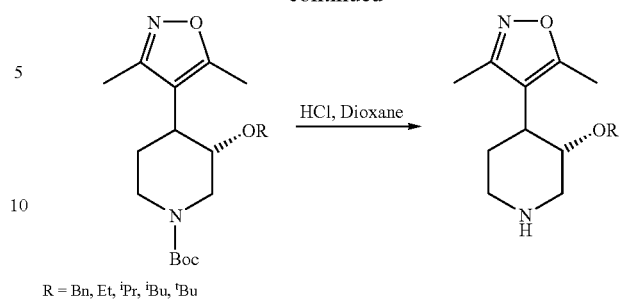
R = Bn, Et, $^i$Pr, $^i$Bu, $^t$Bu
Ref: Org. Lett. 2001, 3(15), 2317-2320.
3.
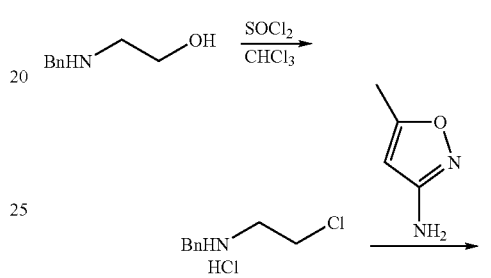
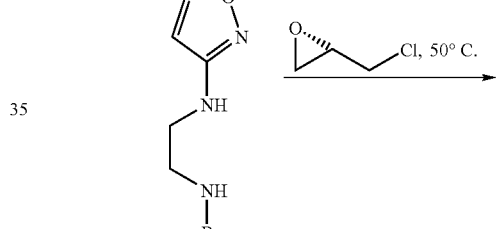
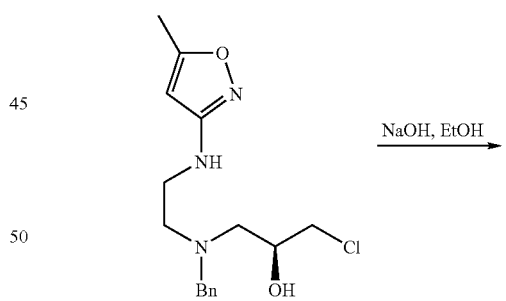
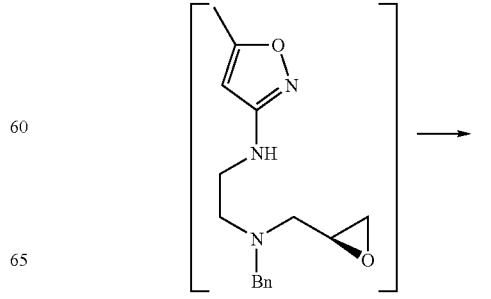

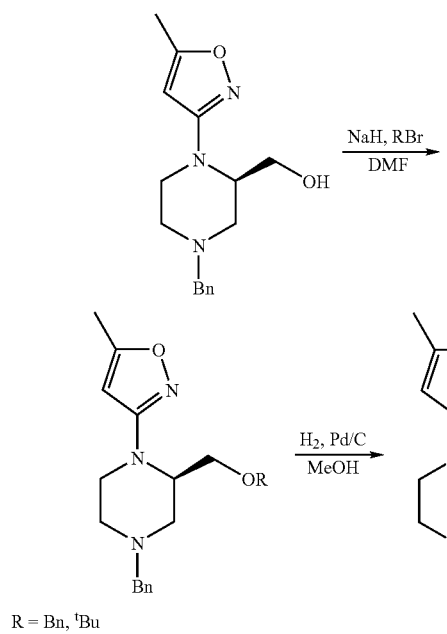
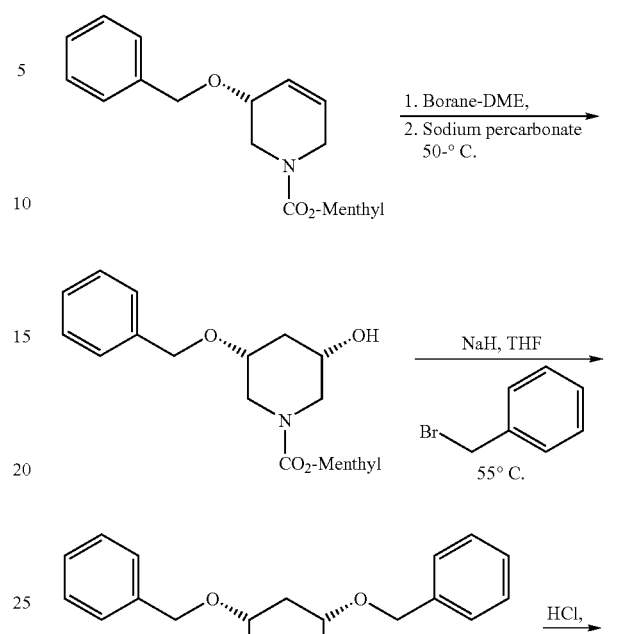
R = Bn, tBu
3,5-Alkyloxy-Piperidines
Synthetic Route:
3-Alkyloxy-4-Furano-Piperidines:
1.
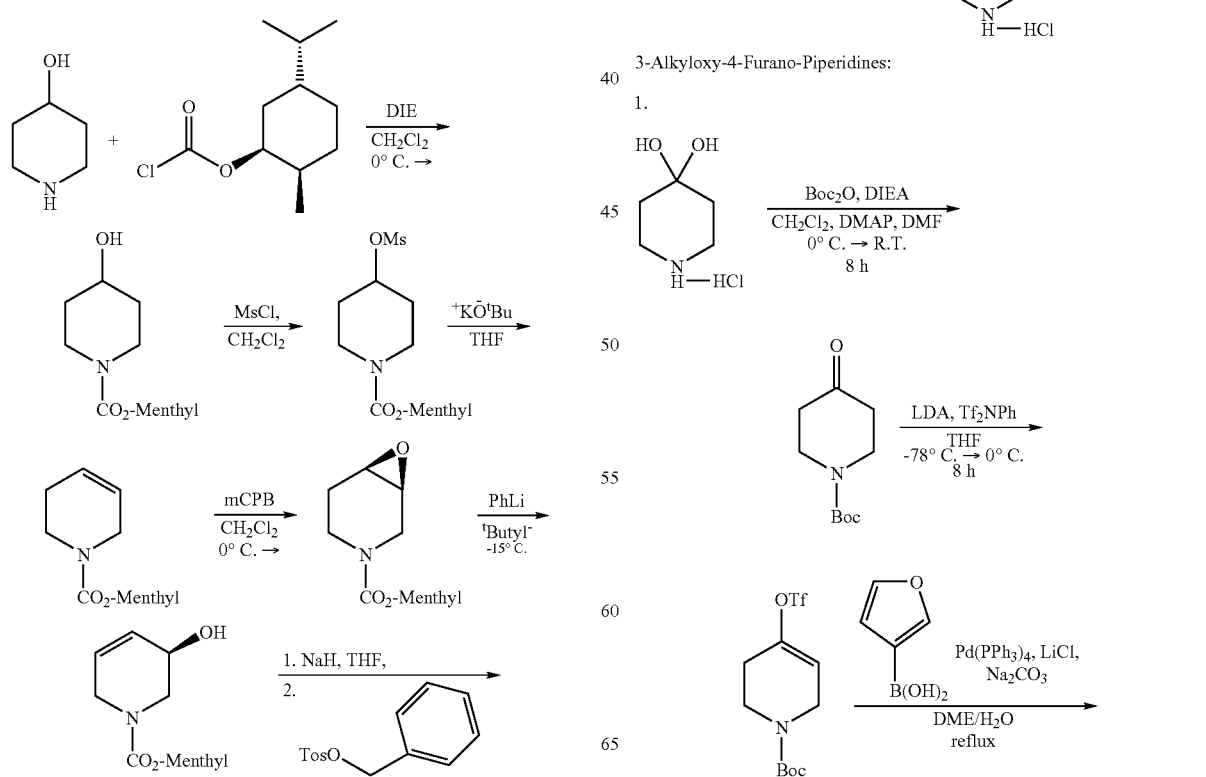

81
-continued
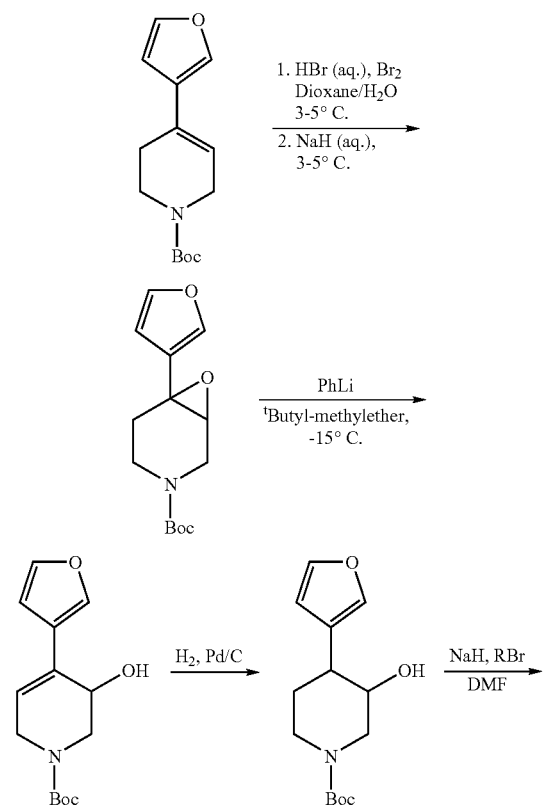
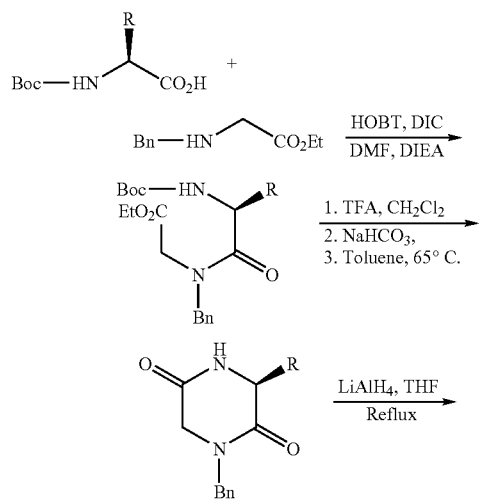
R = Bn, Et, iPr, iBu, tBu
3-Alkyloxy- and 3-Alkyl-4-Furano-Piperazines
82
-continued
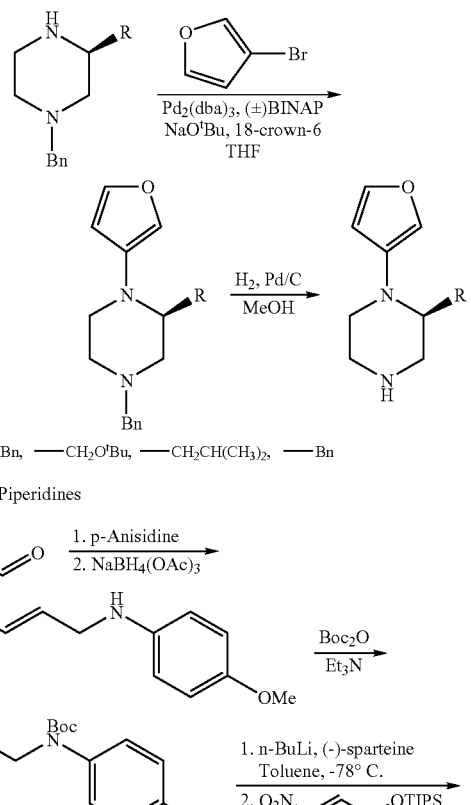
R = —CH₂OBn, —CH₂OtBu, —CH₂CH(CH₃)₂, —Bn
3,5-Alkyloxy-Piperidines
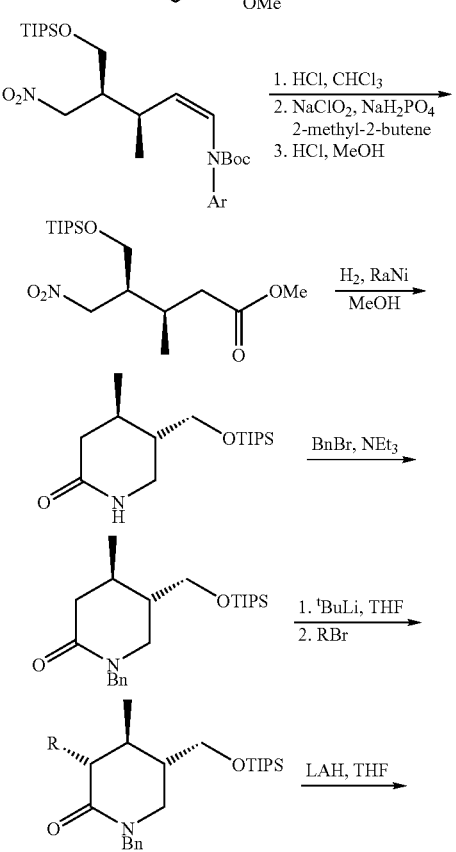

-continued
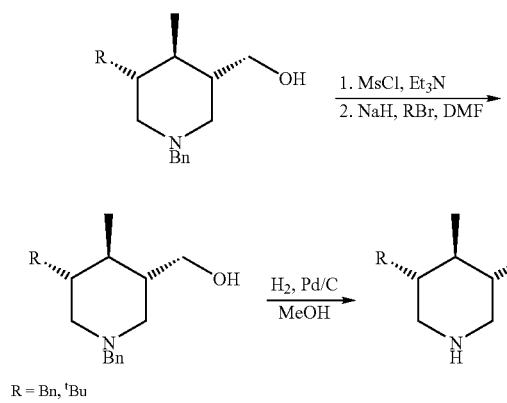
R = Bn, tBu
3-Alkyloxy- and 3-Alkyl-4-Oxazolo-Piperazines
1.
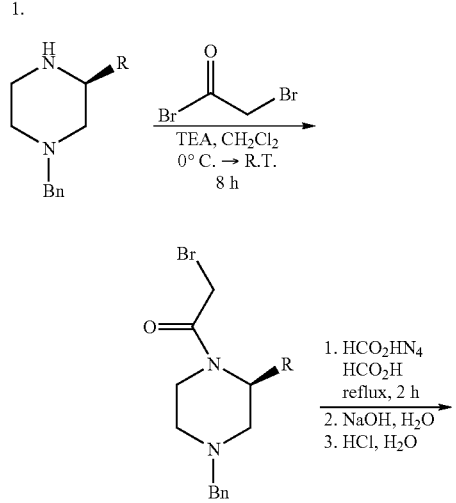
2.
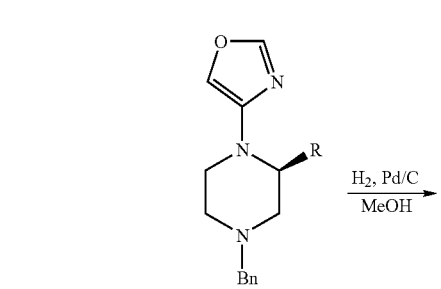
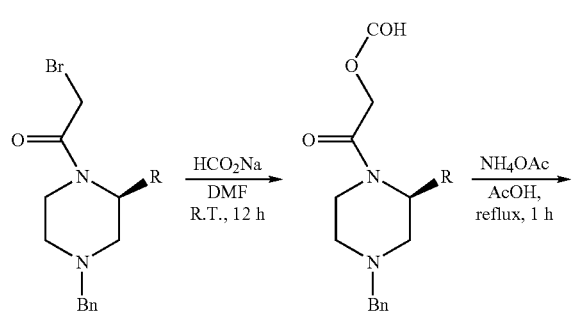
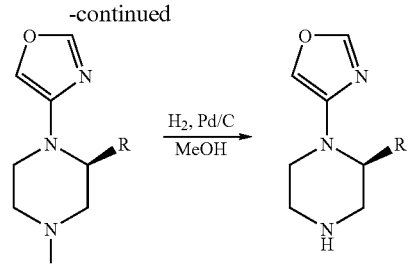
3.
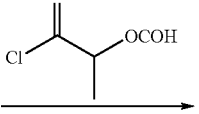
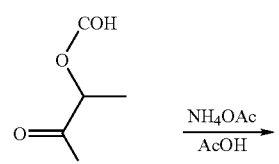
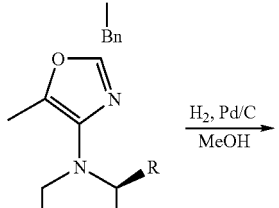
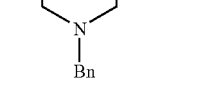
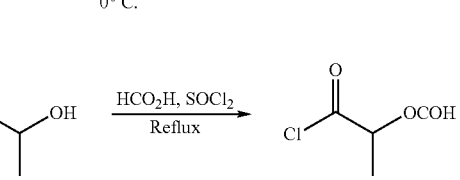
R = —OBn, —OtBu, —CH₂CH(CH₃)₂, —Bn
Exemplifications of the invention may be made as taught by Lesma et al., *J. Org. Chem.,* 1998, 63, 3492 (and references cited therein):
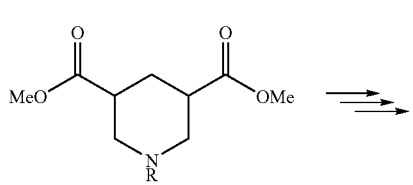

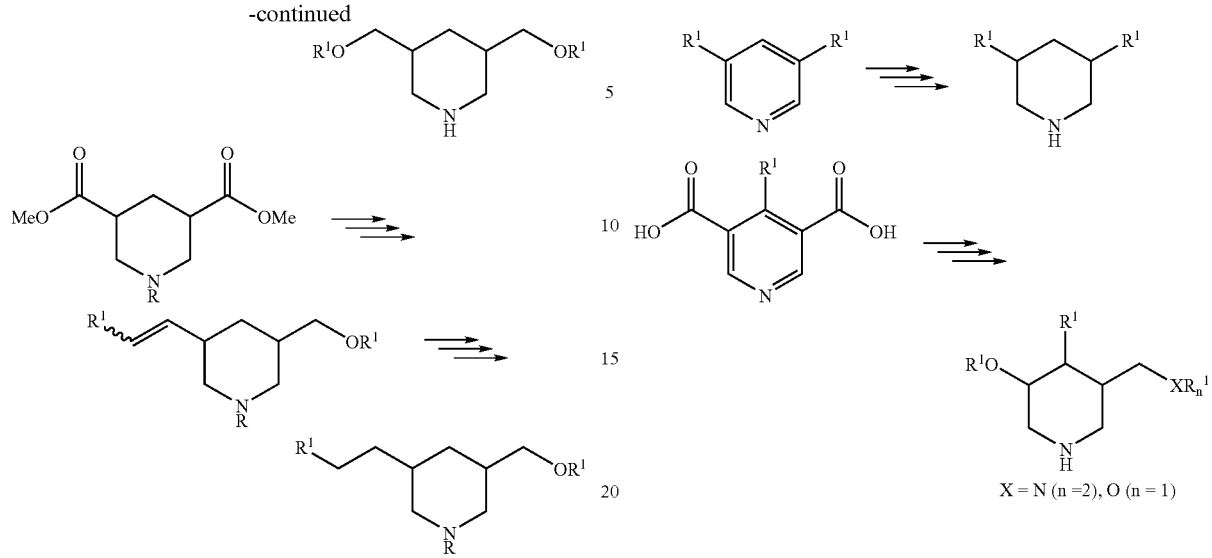

Exemplifications of the invention may be made as taught by Yu et al. *Tetrahedron Lett.,* 2000, 41, 547 (and references cited therein):

Exemplifications of the invention may be made as taught by Liras et al *Org. Lett.,* 2001, 3, 3483 (and references cited therein):

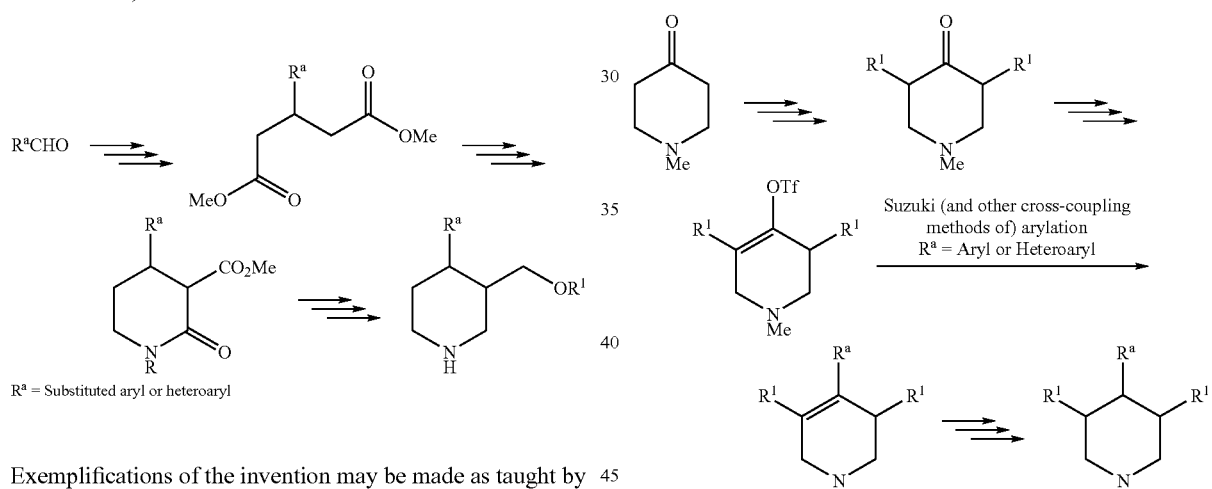

Exemplifications of the invention may be made as taught by Gmeiner et al *J. Org. Chem.,* 2001, 66, 7408 (and references cited therein):

Exemplifications of the invention may be made as taught by Liebeskind et al. *Org. Lett.,* 2001, 3, 3381 (and references cited therein):

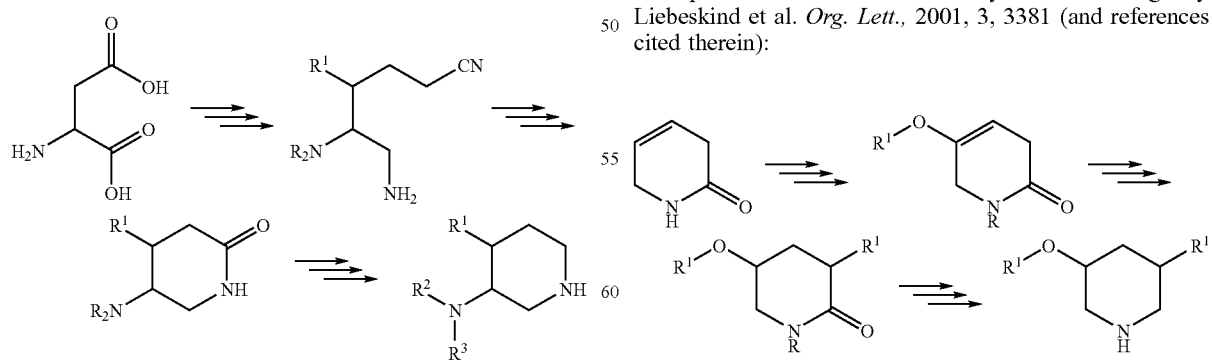

Exemplifications of the invention may be made as taught by et al. *J. Org. Chem.,* 2000, 85, 7432 (and references cited therein):

Exemplifications of the invention may be made as taught by Beak et e *J. Am. Chem. Soc* 2001, 123, 1004 (and references cited therein):

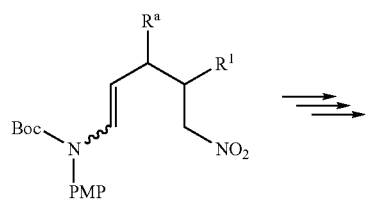

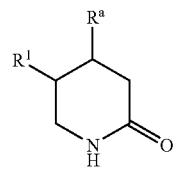

Exemplifications of the invention may be made as taught by Hayashi et al. *J. Org. Chem.*, 2001, 66, 6852 (and references cited ther

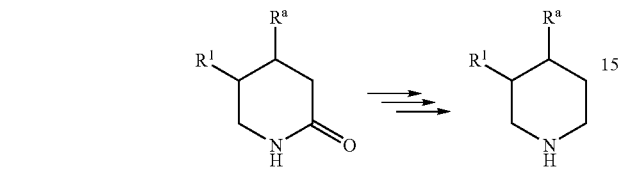

Exemplifications of the invention may be made as taught by Ganem et al. *Org Lett.*, 2001, 3, 201 (and references cited therein):

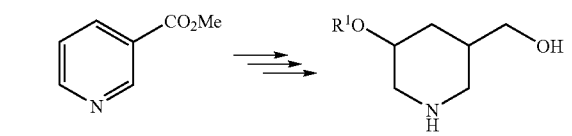

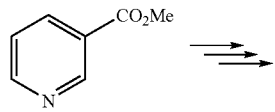

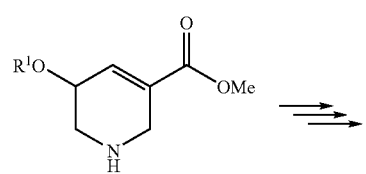

-continued

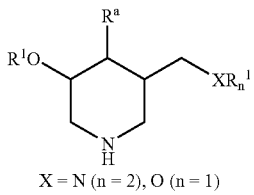

X = N (n = 2), O (n = 1)

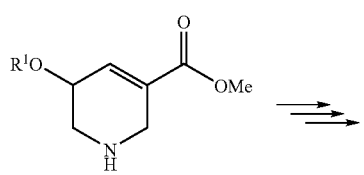

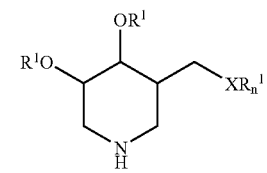

Exemplifications of the invention may be made as taught by Liu et al. *Tetrahedron: Asymmetry*, 2001, 12, 419 (and references cited therein):

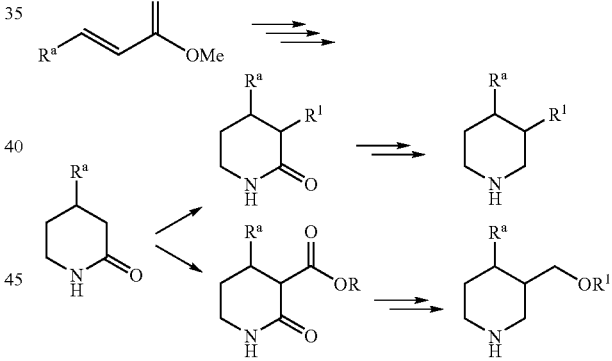

Exemplifications of the invention may be made as taught by Sabol et al. *Tetrahedron Lett.*, 2001, 42, 1631 (and references cited therein):

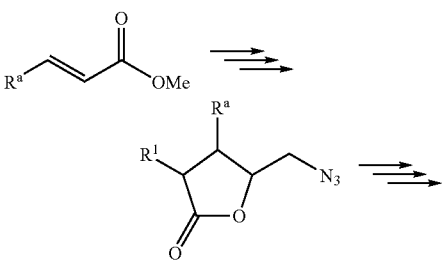

-continued

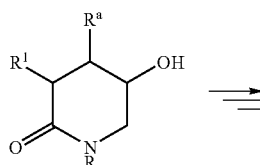 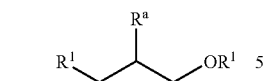

Exemplifications of the invention may be made as taught by Diez et al. *Tetrahedron Lett.* 2001, 42, 871 (and references cited therein):

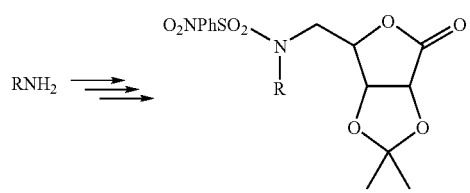

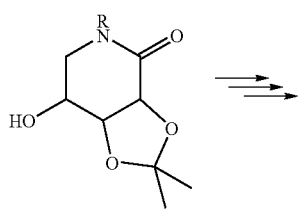

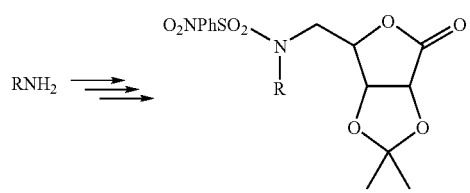

Exemplifications of the invention may be made as taught by Buchner & Metz *Tetrahedron Lett.*, 2001, 42, 5381 (and references cited therein):

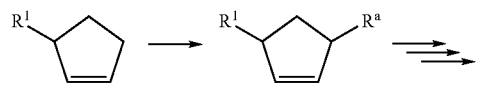

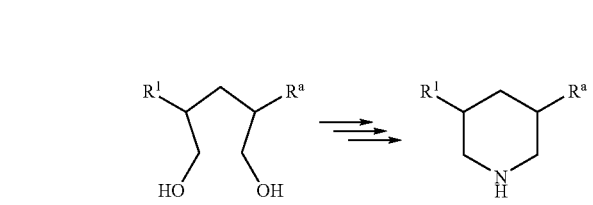

Exemplifications of the invention may be made a taught by Cossy et al. *Tetrahedron Lett.*, 2001, 4, 5705 (and references cited therein):

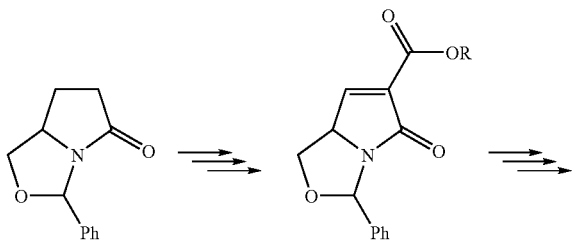

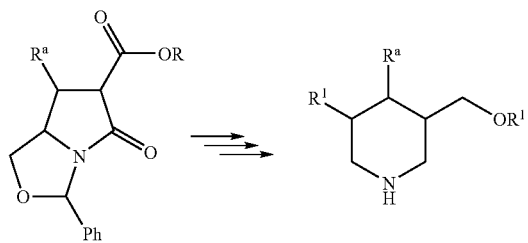

Exemplifications of the invention may be made s taught by Zacharie et al. *J. Org. Chem.* 2001, 66, 5264 (and references cited therein):

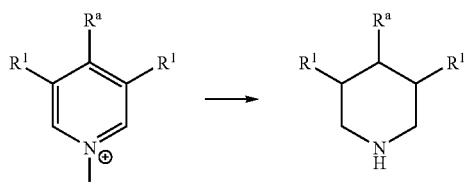

Exemplifications of the invention may be made as taught by Pandey & Kapur *Synthesis* 2001, 1263 (and references cited therein):

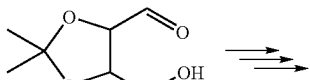

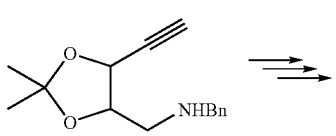

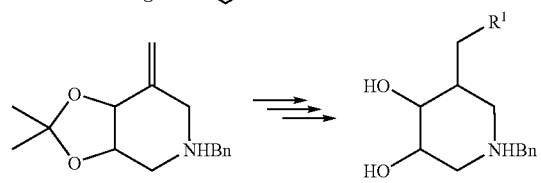

Exemplifications of the invention may be made as taught by Amat et al. *Org. Lett.* 2001, 3, 611 (and references cited therein):

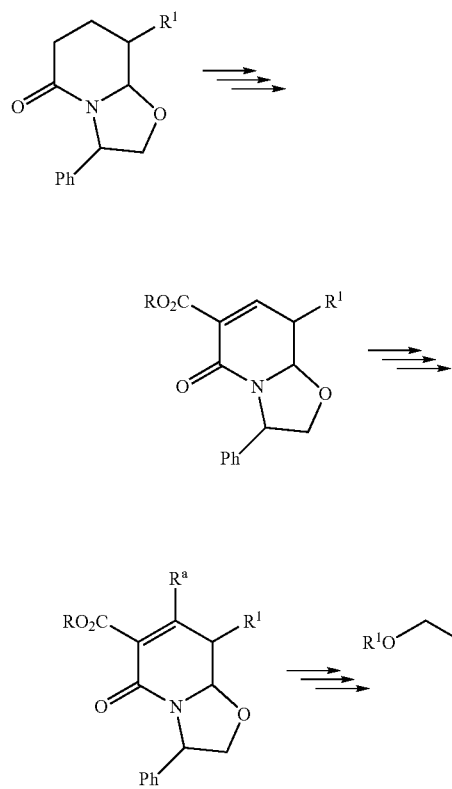

Exemplifications of the invention may be made as taught by Amat et al. *Org. Lett.* 2001, 3, 3257 (and references cited therein):

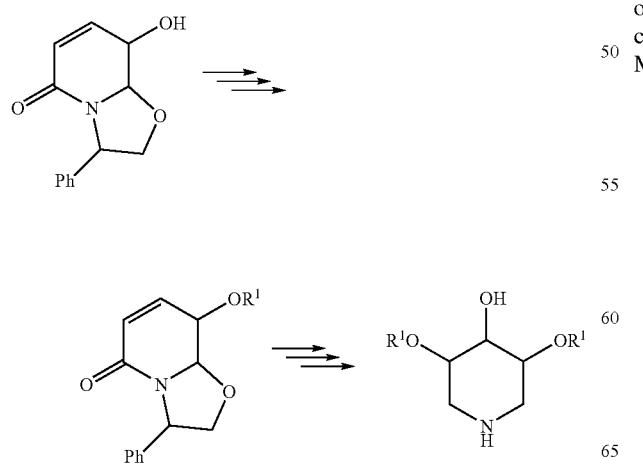

In accordance with the above preparative schemes, Example 1 was prepared as described below.

EXAMPLE 1

(+/−)-(3R,4R)-4-(3-hydroxyphenyl)piperidin-3-yl 1,1'-biphenyl-4-carboxylate hydrochloride

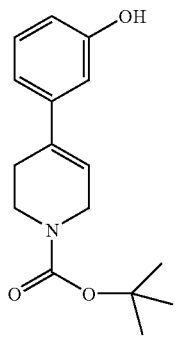

Step 1: Preparation of tert-Butyl 4-(3-hydroxyphenyl)-3,6-dihydropyridine-1(2H)-carboxylate The tert-butyl 4-{[(trifluoromethyl)sulfonyl]oxy}-3,6-dihydropyridine-1(2H)-carboxylate (6.42 g, 9.23 mmol), 3-(4,4,5,5-tetramethyl-1,3,2-dioxaborolan-2-yl)phenol 4.69 g, 21.3 mmol, and tetrakis(triphenylphosphine)palladium(0) (200 mg, 0.17 mmol) were mixed in dioxane (20 mL), ethanol (10 mL) and 2 M aqueous sodium carbonate (5.0 mL). The solution was refluxed for 4 hours, cooled to room temperature, and poured into ethyl acetate (150 mL). The solution was extracted with 1N aqueous hydrochloric acid (2×100 mL), filtered through celite, extracted with saturated aqueous sodium bicarbonate (2×100 mL), and extracted with saturated with saturated aqueous ammonium chloride (2×100 mL). The solution was dried over sodium sulfate, vacuum filtered through a bed of silica gel and solvent removed at reduced pressure to afford a red oil. The tert-butyl 4-(3-hydroxyphenyl)-3,6-dihydropyridine-1(2H)-carboxylate (5.3 g, 19.2 mmol) was obtained as a combination of two crystallization crops from dichloromethane/hexane crystallization solvents. HRMS m/z 276.1614 (calcd for M+H 276.1594.)

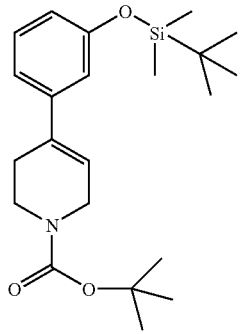

Step 2: Preparation of tert-Butyl 4-(3-{[tert-butyl(dimethyl)silyl]oxy}phenyl)-3,6-dihydropyridine-1(2H)-carboxylate The tert-butyl 4-(3-hydroxyphenyl)-3,6-dihydropyridine-1(2H)-carboxylate (4.01 g, 14.58 mmol), tert-butyldimethylsilyl chloride (2.73 g, 18.22 mmol), triethylamine (4.01 g, 40.0 mmol) and a catalytic amount of dimethylaminopyridine (100 mg, 0.80 mmol) were mixed in dichloromethane (100 mL) at room temperature for 16 h. The solvent was removed at reduced pressure and the resulting semisolid dissolved in diethylether (100 mL). The solution was extracted with 1N aqueous hydrochloric acid (2×50 mL), extracted with saturated aqueous sodium bicarbonate (2×50 mL), and extracted with saturated with saturated aqueous ammonium chloride (2×50 mL). The solution was dried over sodium sulfate and solvent removed at reduced pressure. The tert-butyl 4-(3-{[tert-butyl(dimethyl)silyl]oxy}phenyl)-3,6-dihydropyridine-1(2H)-carboxylate (4.8 g, 12.33 mmol) was isolated as a clear colorless oil by preparative silica chromatography (5% ethyl acetate/95% hexanes). HRMS m/z 388.2305 (calcd for M−H 388.2302.)

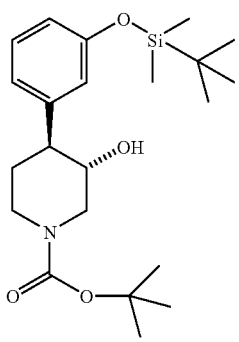

Step 3: Preparation of (+/−)-tert-Butyl (3S,4S)-4-(3-{[tert-butyl(dimethyl)silyl]oxy}phenyl)-3-hydroxypiperidine-1-carboxylate The tert-butyl 4-(3-{[tert-butyl(dimethyl)silyl]oxy}phenyl)-3,6-dihydropyridine-1(2H)-carboxylate (4.61 g, 11.85 mmol) was dissolved in tetrhydrofuran (50 mL). The solution was cooled to 0° C. and borane-methyl sulfide complex (1.79 g, 23.7 mmol) was slowly added. The solution was heated to reflux for 2 H and cooled to room temperature. 1 M aqueous sodium hydroxide solution (30 mL) was added dropwise to control the gas evolution. 35% Aqueous hydrogen peroxide (45 mL) was added and solution refluxed for 2 H. The solution was cooled to room temperature and poured into diethylether (200 mL). The solution was extracted with 2.5 M aqueous sodium hydroxide (2×75 mL) and the organic layer checked for peroxides with starch iodide paper. The organic layer extracted with saturated ammonium chloride (1×50 mL) and dried over sodium sulfate. The (+/−)-tert-butyl (3S,4S)-4-(3-{[tert-butyl(dimethyl)silyl]oxy}phenyl)-3-hydroxypiperidine-1-carboxylate (2.3 g, 5.65 mmol) as a semi solid by preparative silica chromatography (0-10% ethyl acetate/hexanes). HRMS m/z 408.2564 (calcd for M+H 408.2565.)

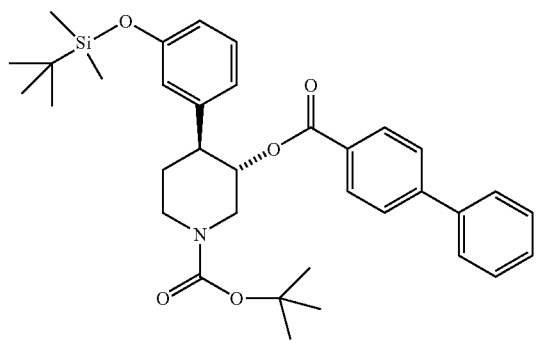

Step 4: Preparation of (+/−)-tert-Butyl (3R,4R)-3-[(1,1'-biphenyl-4-ylcarbonyl)oxy]-4-(3-{[tert-butyl(dimethyl)silyl]oxy}phenyl)piperidine-1-carboxylate The (+/−)-tert-butyl (3S,4S)-4-(3-{[tert-butyl(dimethyl)silyl]oxy}phenyl)-3-hydroxypiperidine-1-carboxylate (206 mg, 0.51 mmol), 1'-biphenyl-4-carbonyl chloride (540 mg, 2.50 mmol), triethylamine (400 mg, 4.00 mmol), and a catalytic amount of dimethylaminopyridine (10.0 mg, 0.08 mmol) was mixed together in acetonitrile (10.0 mL) at room temperature for 16 H. Ammonium hydroxide solution (5 mL) was added to the solution and it was stirred for 1 H. The heterogeneous solution was poured into ethyl acetate (50 mL) and hexanes (5 mL). The solution was extracted with 1N aqueous hydrochloric acid (2×10 mL), extracted with saturated aqueous sodium bicarbonate (2×10 mL), and extracted with saturated with saturated aqueous ammonium chloride (2×10 mL). The solution was dried over sodium sulfate and solvent removed at reduced pressure. The (+/−)-tert-butyl (3R,4R)-3-[(1,1'-biphenyl-4-ylcarbonyl)oxy]-4-(3-{[tert-butyl(dimethyl)silyl]oxy}phenyl)piperidine-1-carboxylate (164 mg, 0.28 mmol) was isolated as a semisolid by radial silica gel chromatography (25% ethyl acetate/hexanes). HRMS m/z 588.3150 (calcd for M+H 588.3140.)

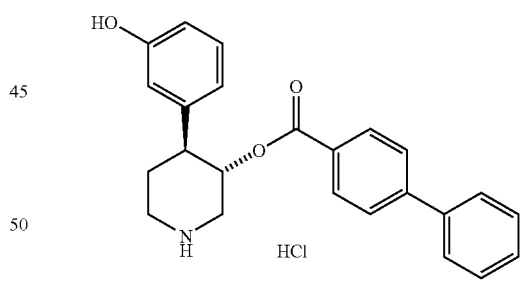

Step 5: Preparation of (+/−)-(3R,4R)-4-(3-Hydroxyphenyl)piperidin-3-yl 1,1'-biphenyl-4-carboxylate hydrochloride The (+/−)-tert-butyl (3R,4R)-3-[(1,1'-biphenyl-4-ylcarbonyl)oxy]-4-(3-{[tert-butyl(dimethyl)silyl]oxy}phenyl)piperidine-1-carboxylate (91 mg, 0.16 mmol) was dissolved in 4 N Hydrogen chloride in dioxanes (3.0 mL). The solution was stirred for 4 H at room temperature and diethylether (10 mL) was added. The solution was kept at room temperature for 16 H and solids formed. The (+/−)-(3R,4R)-4-(3-hydroxyphenyl)piperidin-3-yl 1,1'-biphenyl-4-carboxylate hydrochloride (56 mg, 0.13 mmol) was obtained as a white solid. HRMS m/z 374.1753 (calcd for M+H 374.1751.)

The invention is illustrated further by the following examples which are not to be construed as limiting the invention in scope or spirit to the specific procedures described in them.

Examples 2 through 60, as represented by the structures shown below, were prepared using similar procedures as those described above. Example 1 and examples 2-60 are shown below:

| | Structure | Compound Name(s) | Exact Mass (m + H) | Calc. Exact Mass (M + H) |
|---|---|---|---|---|
| Example 1 | 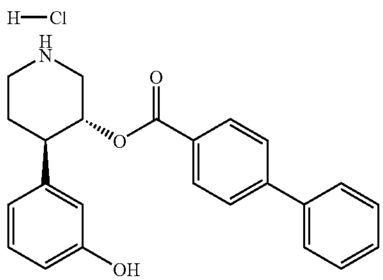 | (+/−)-(3R,4R)-4-(3-hydroxyphenyl)piperidin-3-yl 1,1'-biphenyl-4-carboxylate hydrochloride | 374.1753 | 374.1784 |
| Example 2 | 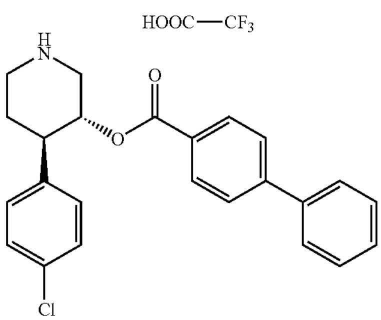 | (+/−)-(3R,4R)-4-(4-chlorophenyl)piperidin-3-yl 1,1'-biphenyl-4-carboxylate trifluoroacetate | 392.1417 | 392.1418 |
| Example 3 | 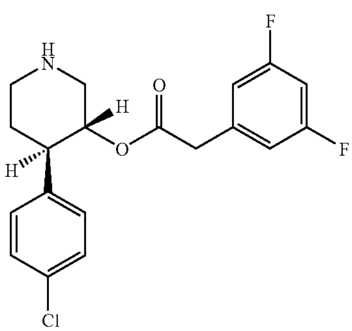 | (+/−)-(3R,4R)-4-(4-chlorophenyl)piperidin-3-yl (3,5-difluorophenyl)acetate | 366.1072 | 366.1072 |
| Example 4 | 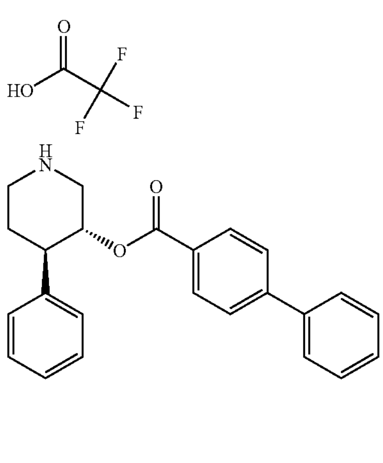 | (+/−)-(3R,4R)-4-phenylpiperidin-3-yl 1-naphthoate hydrochloride | 358.1785 | 358.1802 |

-continued

| Structure | Compound Name(s) | Exact Mass (m + H) | Calc. Exact Mass (M + H) |
|---|---|---|---|
| Example 5 | (+/−)-(3R,4R)-4-(4-fluorophenyl)piperidin-3-yl 1,1-biphenyl-4-carboxylate trifluoroacetate | 376.1713 | 3761303 |
| Example 6 | (+/−)-(3R,4R)-4-phenylpiperidin-3-yl 4-(trifluoromethoxy)benzoate hydrochloride | 366.1292 | 366.1317 |
| Example 7 | (+/−)-(3S,4S)-4-phenylpiperidin-3-yl 4-iodobenzoate hydrochloride | 408.0429 | 408.0461 |
| Example 9 | (+/−)-(3R,4R)-4-phenylpiperidin-3-yl phenoxyacetate hydrochloride | 312.1598 | 312.16 |
| Example 10 | (+/−)-(3R,4R)-4-phenylpiperidin-3-yl 4-(trifluoromethyl)benzoate hydrochloride | 350.1381 | 350.1368 |

-continued

| Structure | Compound Name(s) | Exact Mass (m + H) | Calc. Exact Mass (M + H) |
|---|---|---|---|
| Example 11 | (+/−)-(3R,4R)-4-phenylpiperidin-3-yl 4-cyanobenzoate hydrochloride | 307.1413 | 307.1441 |
| Example 12 | (+/−)-(3R,4R)-4-phenylpiperidin-3-yl 3-methylbenzoate trifluoroacetate | 296.1644 | 296.1645 |
| Example 13 | (+/−)-(3R,4R)-4-phenylpiperidin-3-yl 3-methoxybenzoate trifluoroacetate | 312.1623 | 312.1595 |
| Example 14 | (+/−)-(3R,4R)-4-phenylpiperidin-3-yl 2-methoxybenzoate hydrochloride | 312.1610 | 312.1594 |
| Example 15 | (+/−)-(3R,4R)-4-phenylpiperidin-3-yl benzoate hydrochloride | 282.1470 | 282.1489 |

-continued

| Structure | Compound Name(s) | Exact Mass (m + H) | Calc. Exact Mass (M + H) |
|---|---|---|---|
| Example 16 | (+/−)-(3S,4S)-4-phenylpiperidin-3-yl 3',4'-dimethoxy-1,1'-biphenyl-4-carboxylate hydrochloride | 418.2020 | 418.2013 |
| Example 17 | (+/−)-(3S,4S)-4-phenylpiperidin-3-yl 4-(5-chlorothien-2-yl)benzoate hydrochloride | 398.0959 | 398.0976 |
| Example 18 | (+/−)-(3S,4S)-4-phenylpiperidin-3-yl 4'-(trifluoromethyl)-1,1'-biphenyl-4-carboxylate hydrochloride | 426.1671 | 426.1675 |
| Example 19 | (+/−)-(3R,4R)-4-phenylpiperidin-3-yl 2-methylbenzoate hydrochloride | 296.1622 | 296.1645 |
| Example 20 | (+/−)-(3R,4R)-4-phenylpiperidin-3-yl 3-(trifluoromethyl)benzoate hydrochloride | 350.1351 | 350.1362 |

-continued

| | Structure | Compound Name(s) | Exact Mass (m + H) | Calc. Exact Mass (M + H) |
|---|---|---|---|---|
| Example 21 | 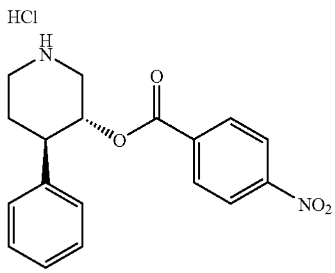 | (+/−)-(3R,4R)-4-phenylpiperidin-3-yl 4-nitrobenzoate hydrochloride | 327.1330 | 327.1339 |
| Example 22 | 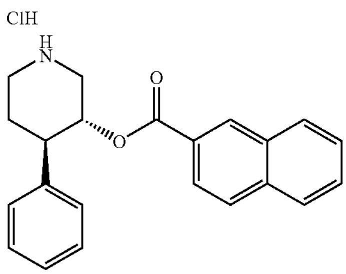 | (+/−)-(3R,4R)-4-phenylpiperidin-3-yl 2-naphthoate hydrochloride | 332.1631 | 332.1645 |
| Example 23 | 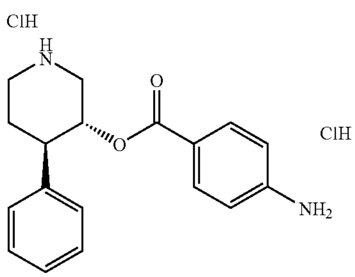 | (+/−)-(3R,4R)-4-phenylpiperidin-3-yl 4-aminobenzoate dihydrochloride | 297.1615 | 297.1598 |
| Example 24 | 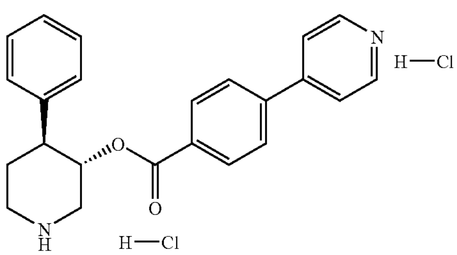 | (+/−)-(3S,4S)-4-phenylpiperidin-3-yl 4-pyridin-4-ylbenzoate dihydrochloride | 359.1733 | 359.1754 |
| Example 25 | 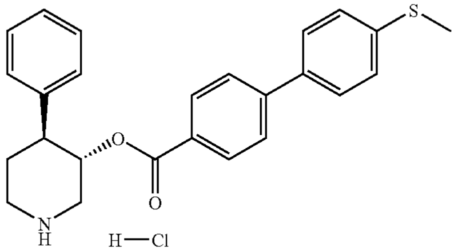 | (+/−)-(3S,4S)-4-phenylpiperidin-3-yl 4'-(methylthio)-1,1'-biphenyl-4-carboxylate hydrochloride | 404.1684 | 404.0455 |

-continued

| | Structure | Compound Name(s) | Exact Mass (m + H) | Calc. Exact Mass (M + H) |
|---|---|---|---|---|
| Example 26 | 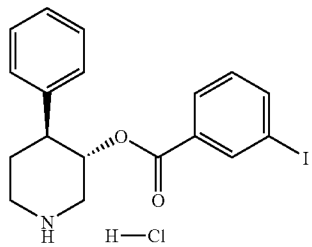 | (+/−)-(3S,4S)-4-phenylpiperidin-3-yl 3-iodobenzoate hydrochloride | 408.0455 | 407.0382 |
| Example 27 | 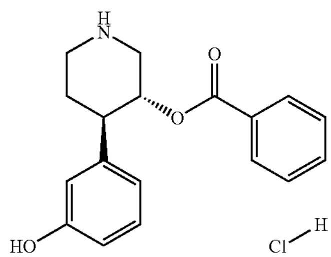 | (+/−)-(3R,4R)-4-(3-hydroxyphenyl)piperidin-3-yl benzoate hydrochloride | 298.1463 | 298.1438 |
| Example 28 | 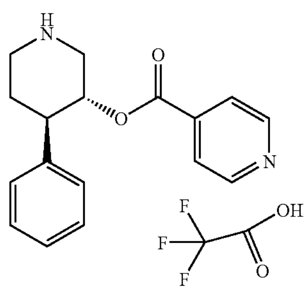 | (+/−)-(3R,4R)-4-(3-hydroxyphenyl)piperidin-3-yl benzoate hydrochloride | 283.1428 | 283.1441 |
| Example 29 | 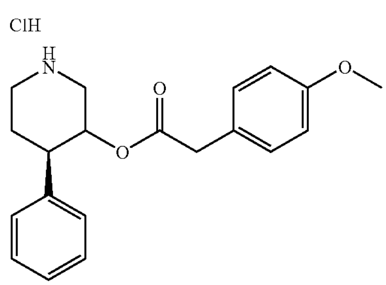 | (3R,4R)-4-phenylpiperidin-3-yl 1,1'-biphenyl-4-carboxylate | 326.1760 | 326.1751 |
| Example 30 | 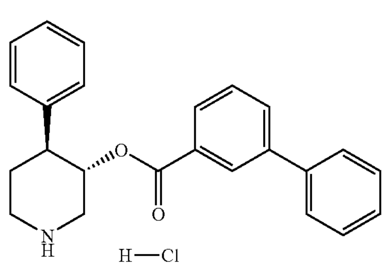 | (+/−)-(3S,4S)-4-phenylpiperidin-3-yl 1,1'-biphenyl-3-carboxylate hydrochloride | 358.1835 | 358.1802 |

-continued

| Structure | Compound Name(s) | Exact Mass (m + H) | Calc. Exact Mass (M + H) |
|---|---|---|---|
| Example 31 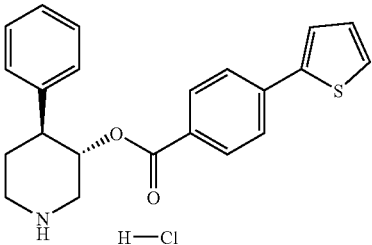 | (+/−)-(3S,4S)-4-phenylpiperidin-3-yl 4-thien-2-ylbenzoate hydrochloride | 364.1387 | 364.1366 |
| Example 32 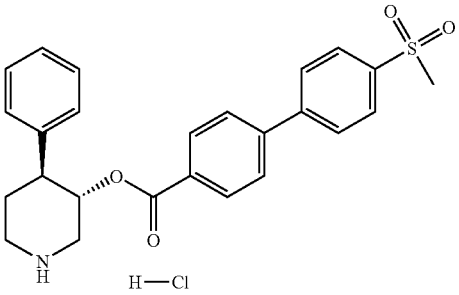 | (+/−)-(3S,4S)-4-phenylpiperidin-3-yl 4'-(methylsulfonyl)-1,1'-biphenyl-4-carboxylate hydrochloride | 436.1559 | 436.1577 |
| Example 33 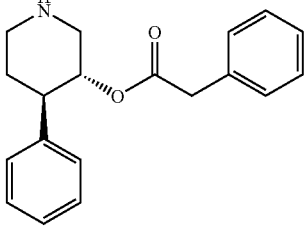 | (+/−)-(3R,4R)-4-phenylpiperidin-3-yl phenylacetate hydrochloride | 296.1621 | 296.1645 |
| Example 34 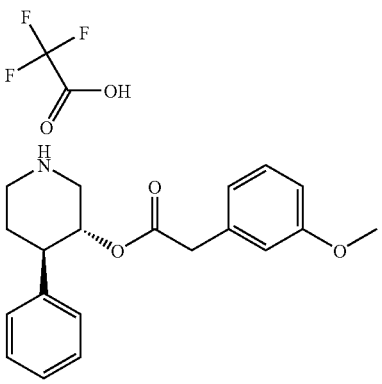 | (+/−)-(3R,4R)-4-phenylpiperidin-3-yl (3-methoxyphenyl)acetate trifluoroacetate | 326.1733 | 326.1751 |

-continued

| | Structure | Compound Name(s) | Exact Mass (m + H) | Calc. Exact Mass (M + H) |
|---|---|---|---|---|
| Example 35 | 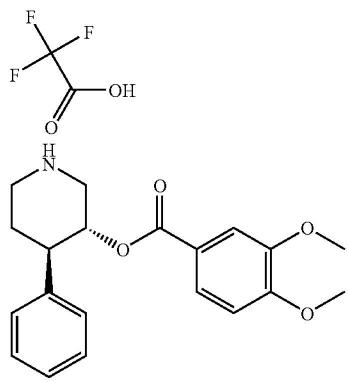 | (+/−)-(3R,4R)-4-phenylpiperidin-3-yl 3,4-dimethoxybenzoate trifluoroacetate | 342.1697 | 342.1700 |
| Example 36 | 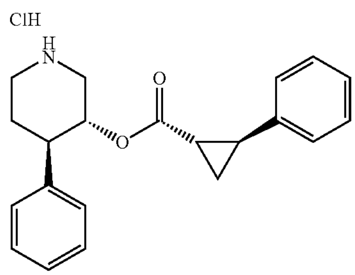 | (+/−)-(3R,4R)-4-phenylpiperidin-3-yl (1R,2S)-2-phenylcyclopropanecarboxylate hydrochloride | 322.1806 | 322.1802 |
| Example 37 | 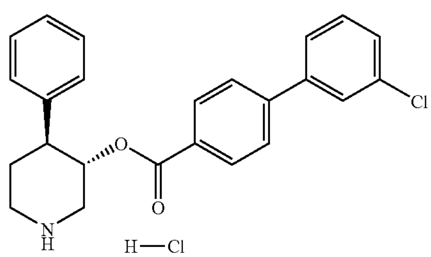 | (+/−)-(3S,4S)-4-phenylpiperidin-3-yl 3'-chloro-1,1'-biphenyl-4-carboxylate hydrochloride | 392.1420 | 392.1412 |
| Example 38 | 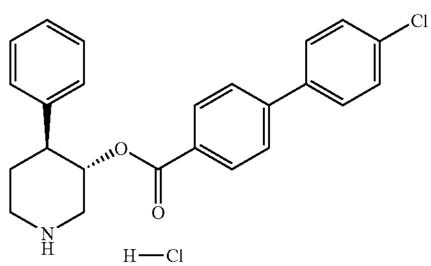 | (+/−)-(3S,4S)-4-phenylpiperidin-3-yl 4'-chloro-1,1'-biphenyl-4-carboxylate hydrochloride | 392.1420 | 392.1412 |
| Example 39 | 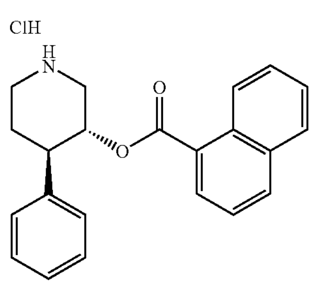 | (+/−)-(3R,4R)-4-phenylpiperidin-3-yl 1-naphthoate hydrochloride | 332.1671 | 332.1645 |

-continued

| Structure | Compound Name(s) | Exact Mass (m + H) | Calc. Exact Mass (M + H) |
|---|---|---|---|
| Example 40 | (+/−)-(3R,4R)-4-phenylpiperidin-3-yl 4-phenoxybenzoate hydrochloride | 374.1751 | 374.1751 |
| Example 41 | (+/−)-(3R,4R)-4-phenylpiperidin-3-yl 3-phenylpropanoate trifluoroacetate | 310.1795 | 310.1802 |
| Example 42 | (+/−)-(3R,4R)-4-phenylpiperidin-3-yl 2-ethylhexanoate hydrochloride | 304.2234 | 304.2271 |
| Example 43 | (+/−)-(3S,4S)-4-phenylpiperidin-3-yl 4-tert-butylbenzoate hydrochloride | 338.2143 | 338.2120 |
| Example 44 | (+/−)-(3S,4S)-4-phenylpiperidin-3-yl 3'-amino-1,1'-biphenyl-4-carboxylate dihydrochloride | 373.1887 | 373.1916 |

-continued

| | Structure | Compound Name(s) | Exact Mass (m + H) | Calc. Exact Mass (M + H) |
|---|---|---|---|---|
| Example 45 | 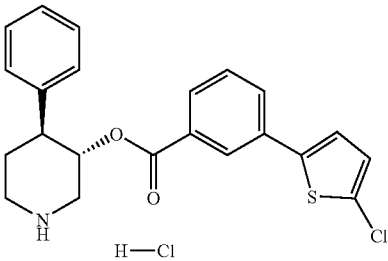 | (+/−)-(3S,4S)-4-phenylpiperidin-3-yl 3-(5-chlorothien-2-yl)benzoate hydrochloride | 398.1016 | 398.0981 |
| Example 46 | 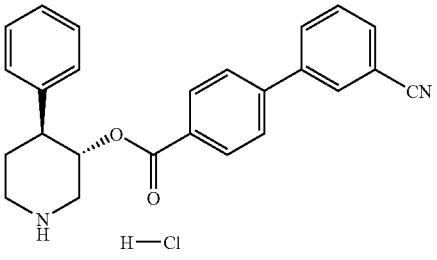 | (+/−)-(3S,4S)-4-phenylpiperidin-3-yl 3'-cyano-1,1'-biphenyl-4-carboxylate hydrochloride (Generated by ACD/Name software) | 373.1767 | 383.1754 |
| Example 47 | 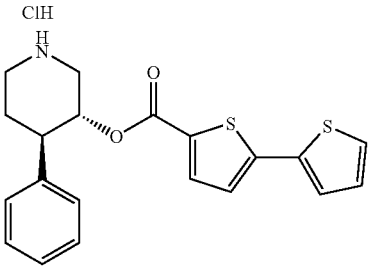 | (+/−)-(3R,4R)-4-phenylpiperidin-3-yl 2,2'-bithiophene-5-carboxylate hydrochloride | 370.0908 | 370.0935 |
| Example 48 | 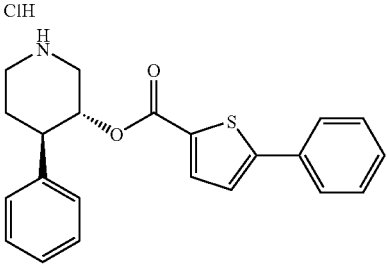 | (+/−)-(3R,4R)-4-phenylpiperidin-3-yl 5-phenylthiophene-2-carboxylate hydrochloride | 364.1335 | 364.1371 |
| Example 49 | 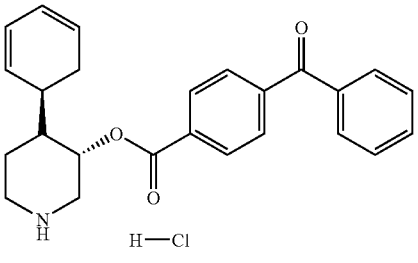 | (+/−)-(3S,4R)-4-[(1R)-cyclohexa-2,4-dien-1-yl]piperidin-3-yl 4-benzoylbenzoate hydrochloride) | 386.1778 | 386.1756 |

-continued

| | Structure | Compound Name(s) | Exact Mass (m + H) | Calc. Exact Mass (M + H) |
|---|---|---|---|---|
| Example 50 | 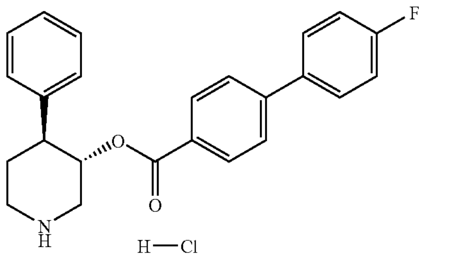 | (+/−)-(3S,4S)-4-phenylpiperidin-3-yl 4'-fluoro-1,1'-biphenyl-4-carboxylate hydrochloride | 376.1679 | 376.1707 |
| Example 51 | 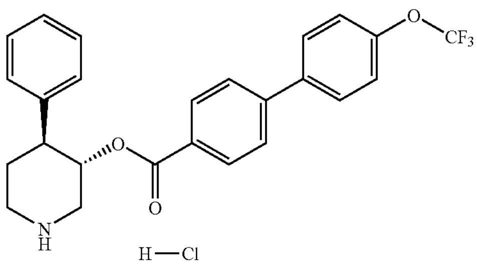 | (+/−)-(3S,4S)-4-phenylpiperidin-3-yl 4'-(trifluoromethoxy)-1,1'-biphenyl-4-carboxylate hydrochloride | 442.1607 | 442.1625 |
| Example 52 | 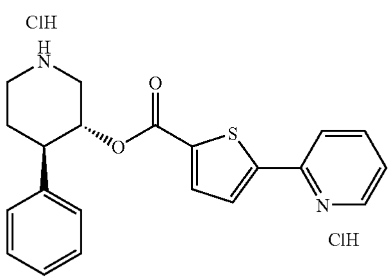 | (+/−)-(3R,4R)-4-phenylpiperidin-3-yl 5-pyridin-2-ylthiophene-2-carboxylate dihydrochloride | 365.1336 | 365.1318 |
| Example 53 | 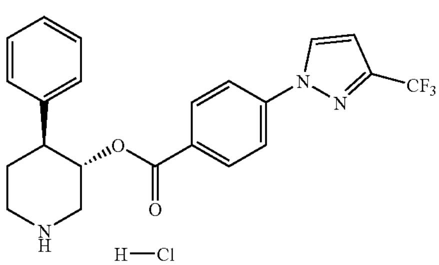 | (+/−)-(3S,4S)-4-phenylpiperidin-3-yl 4-[3-(trifluoromethyl)-1H-pyrazol-1-yl]benzoate hydrochloride | 416.1566 | 416.158 |
| Example 54 | 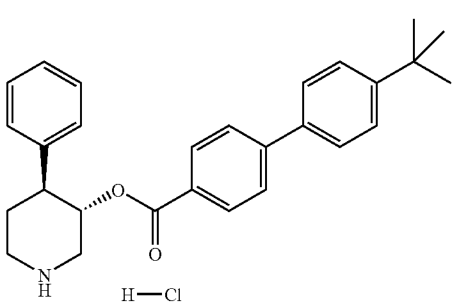 | (+/−)-(3S,4S)-4-phenylpiperidin-3-yl 4'-tert-butyl-1,1'-biphenyl-4-carboxylate hydrochloride | 414.2417 | 414.2428 |

-continued

| Structure | Compound Name(s) | Exact Mass (m + H) | Calc. Exact Mass (M + H) |
|---|---|---|---|
| Example 55 | (+/−)-(3S,4S)-4-phenylpiperidin-3-yl 4'-methoxy-1,1'-biphenyl-4-carboxylate hydrochloride | 388.1936 | 388.1907 |
| Example 56 | (+/−)-4'-({[(3S,4S)-4-phenylpiperidin-3-yl]oxy}carbonyl)-1,1'-biphenyl-4-carboxylic acid hydrochloride | 402.1706 | 402.1700 |
| Example 57 | (+/−)-(3R,4R)-4-phenylpiperidin-3-yl 3-(4-methoxyphenyl)propanoate hydrochloride | 340.1888 | 340.1907 |
| Example 59 | (+/−)-(3R,4R)-4-phenylpiperidin-3-yl acetate hydrochloride | 220.1332 | 220.1334 |
| Example 60 | (+/−)-(3R,4R)-4-pyridin-3-ylpiperidin-3-yl acetate dihydrochloride | 460.1815 | 460.1788 |

Examples 61-79 were prepared in accordance with the above synthetic routes as shown below:

| Example | Structure | FW | Ion Found (ES+) |
|---|---|---|---|
| 61 | 3-(benzyloxy)piperidine | 191.28 | 192.1 |
| 62 | 3-((2-bromobenzyl)oxy)piperidine | 270.17 | 272.1 |
| 63 | 3-((4-bromobenzyl)oxy)piperidine | 270.17 | 270.1 |
| 64 | 3-((4-tert-butylbenzyl)oxy)piperidine | 247.38 | 248.3 |
| 65 | 3-((3-fluorobenzyl)oxy)piperidine | 209.27 | 210.1 |
| 66 | 3-((3-fluorobenzyl)oxy)piperidine derivative | 259.27 | 260.2 |
| 67 | 3-((3-chlorobenzyl)oxy)piperidine | 225.72 | 226.1 |

-continued

| Example | Structure | FW | Ion Found (ES+) |
|---|---|---|---|
| 68 | 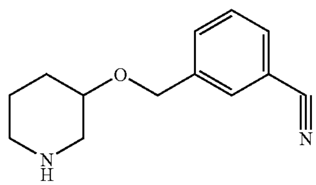 | 216.29 | 217.2 |
| 69 | 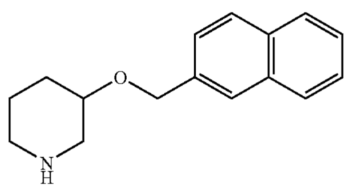 | 241.34 | 242.2 |
| 70 | 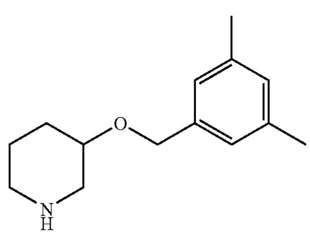 | 219.33 | 220.2 |
| 71 | 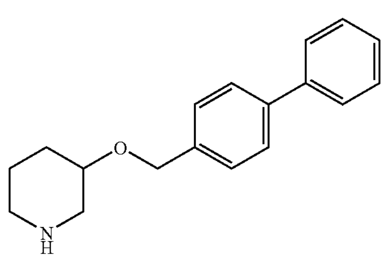 | 267.37 | 268.2 |
| 72 | 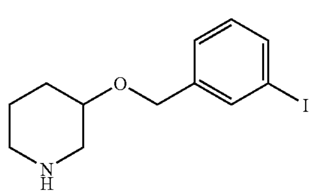 | 317.17 | 318.1 |

-continued

| Example | Structure | FW | Ion Found (ES+) |
|---|---|---|---|
| 73 | 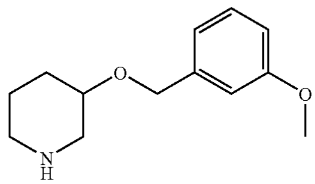 | 221.3 | 222.2 |
| 74 | 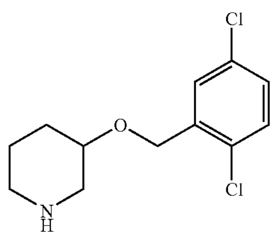 | 260.17 | 260.1 |
| 75 | 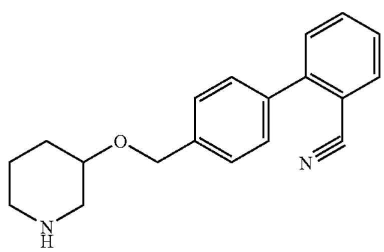 | 292.38 | 293.3 |
| 76 | 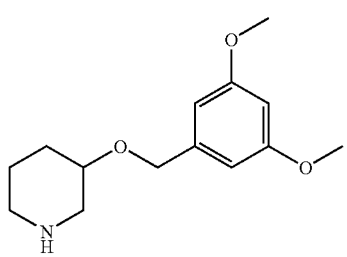 | 251.33 | 252.2 |
| 79 | 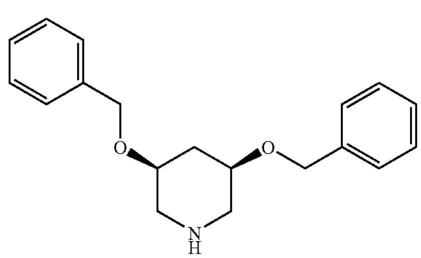 | 297.4 | 298.2 |

Examples 80 was also prepared in accordance with the above synthetic routes as described herein:

EXAMPLE 80

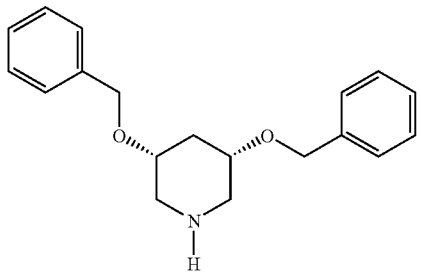

OAMS supporting ions at: ESI+ 298.2

$[\alpha]^{25}_D=0°$ (c 0.72, chloroform). Anal. Calcd for $C_{19}H_{23}NO_2$: C, 76.74; H, 7.80; N, 4.71. Found: C, 76.46; H, 7.76; N, 5.00.

In another embodiment, 3-alkoxy-5-alkyl piperidines of the invention may be prepared utilizing the routes shown below and as described:

Preparation of 3-alkyl-5-benzyloxy piperdines

To a THF (100 ml) solution of 1 (5.4 g, 26.6 mmol) (*JOC*, 1986, 51, 3140), at −78° C., was added LiHMDS (28 ml, 28 mmol, 1.0M in THF). The mixture was stirred for 1 hour followed by addition of benzyl bromide and allowed to warm to room temperature. After stirring overnight at r.t. the reaction was quenched with sat'd aq. $NH_4Cl$ (75 ml) and extracted with EtOAc. The organic layer was washed $NaHCO_3$ (50 ml), brine (50 ml), and dried over $MgSO_4$ to give 4.9 g of 2 (64%) as a mixture of diastereomers. Flash chromatography 10% EtOAc/Heptane to 65% EtOAc/heptane yields 2.9 g of the trans isomer and 2.1 g of the cis isomer.

To a refluxing THF (8 ml) suspension of $LiAl_4$ (0.46 g, 12.3 mmol) was added a THF (8 ml) solution of 2 (2.4 g, 8.2 mmol) (*Biotech & Bioeng* 1998/99, 61, 143). The reaction was maintained at reflux for 12 h followed by cooling to 0° C. and the slow addition of sat's aq. $NaSO_4$. The mixture was diluted with EtOAc and filtered through Celite and the

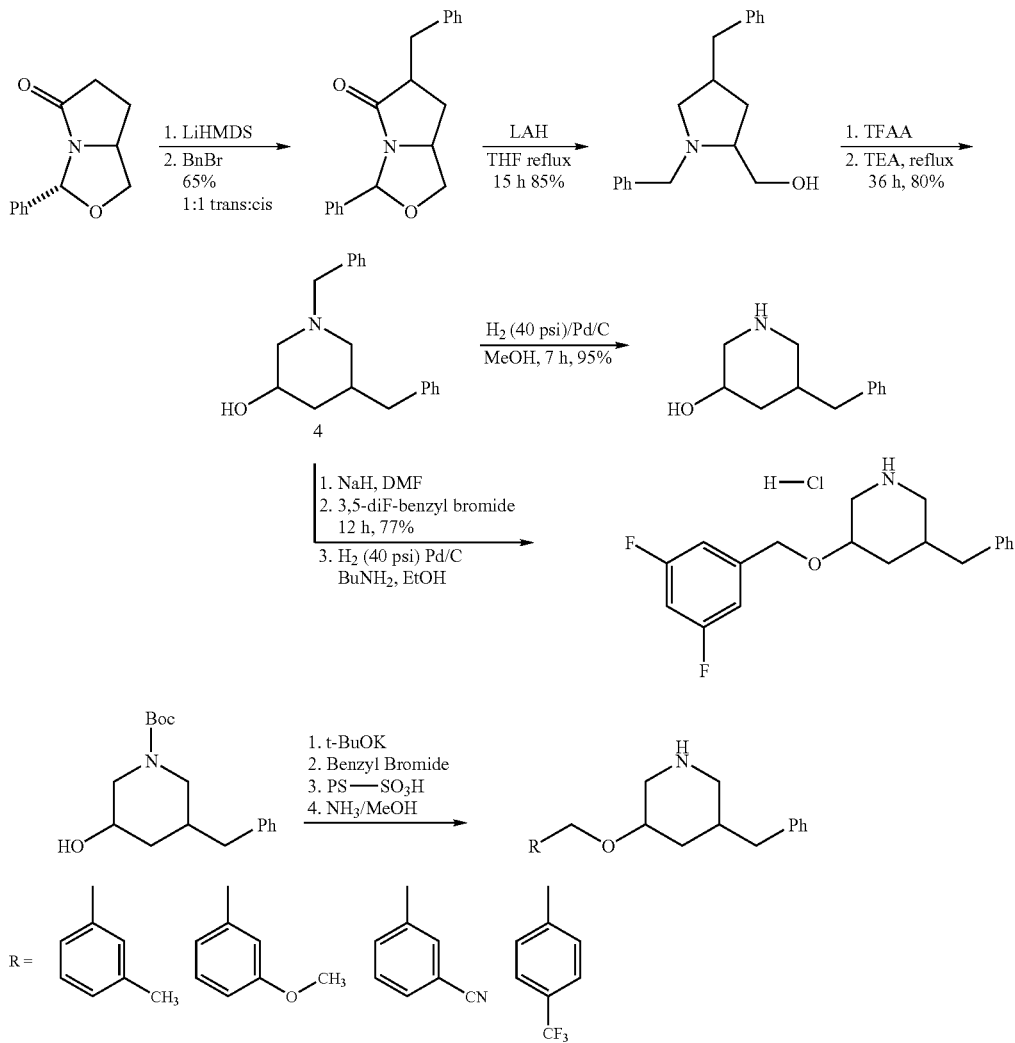

filtrate dried over MgSO$_4$. Concentration in vacuo gave 2.2 g of 3 (85%) as a clear oil. To a THF (60 ml) solution of 3 (2.2 g, 7.8 mmol) was added TFAA (2.5 g, 11.7 mmol) dropwise followed by warming to r.t. After 1.5 h at r.t. Et$_3$N (4.3 ml, 31.2 mmol) was added dropwise followed by heating at reflux for 40 h. After cooling to r.t. the mixture was treated with 10% NaOH and stirred for 1 h. The mixture was diluted with EtOAc (75 ml) and washed with NaHCO$_3$ (2×20 ml), brine (20 ml) and the organic layer dried over Na$_2$SO$_4$. Flash chromatography 5% MeOH/CHCl$_3$ gave 1.6 g of 4 (73%).

A parr apparatus was charged with Pd/C 0.470 mg and 4 (1.26 g, 4.5 mmol) in 40 ml of MeOH. The apparatus was charged with 40 psi. H$_2$ and shaken at r.t. for 6 h. The reaction mixture was filtered through Celite and conc. in vacuo. The resulting residue was dissolved in THF (30 ml) followed by the addition of Boc$_2$O (1.2 g, 5.4 mmol). After stirring at r.t for 3 h the reaction was diluted with EtOAc (70 ml) and washed with H$_2$O (3×20 ml). The organic layer was dried over MgSO$_4$ and concentrated in vacuo to yield 5 (0.74 g, 57%) as a white solid after flash chromatography 50% EtOAc/heptane.

EXAMPLE 82

3-benzyl-5-[(3,5-difluorobenzyl)oxy]piperidine hydrochloride

Compound 5 (0.10 g, 0.34 mmol) in THF (1 ml) was treated with 0.7 ml of 1.0 M t-BuOK in THF and stirred for 15 min. at r.t. The mixture was treated with 2.0 eq. of 3,5-difluorobenzyl bromide and stirred at 50° C. for 18 h. The mixture was diluted with 5 ml of MeOH followed by the addition of 1 g of DOWEX® 50X2-400 ion-exchange resin and stirred at 45° C. for 5 h. The resin was collected by filtration and washed with MeOH and CH$_2$Cl$_2$ (3×10 ml). The resin was then treated with 7N NH$_3$/MeOH to elute the final compound. The desired salt was obtained by treating the amine with either HCl or TFA in Et$_2$O.

HRMS m+H=318.1663

The following were prepared according to the methods described for example 82.

EXAMPLE 83

3-benzyl-5-[(3-methylbenzyl)oxy]piperidine hydrochloride

HRMS m+H=296.2012.

EXAMPLE 84

3-benzyl-5-{[4-(trifluoromethyl)benzyl]oxy}piperidine hydrochloride

HRMS m+H=349.1653

EXAMPLE 85

3-({5-benzylpiperidin-3-yl]oxy}methyl)benzonitrile

HRMS m+H=307.1807.

EXAMPLE 86

3-benzyl-5-[(3-methoxybenzyl)oxy]piperidine hydrochloride

HRMS m+H=312.1965.

EXAMPLE 87

5-benzylpiperidin-3-yl 1,1'-biphenyl-4-carboxylate trifluoroacetate

HRMS m+H=372.1953

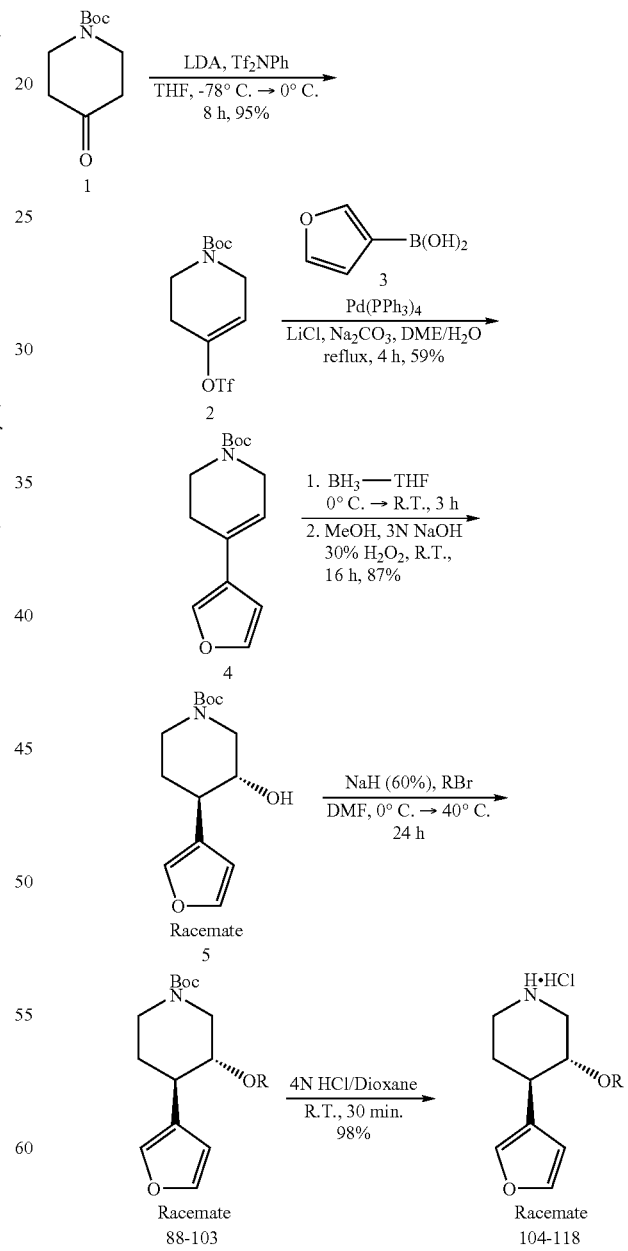

4-Trifluoromethanesulfonyloxy-3,6-dihydro-2H-pyridine-1-carboxylic acid tert-butyl ester (2). A solution of t-butyl-4-oxopiperidine-1-carboxylate (6.50 g, 32.6 mmol) in THF (50 mL) was added dropwise to a stirred solution of LDA (24 mL, 35.8 mmol, 1.1 eq., 1.5 M in hexanes) in THF (50 mL) at −78° C. After stirring for 30 min, a solution of N-phenyltrifluoromethanesulfonamide (12.48 g, 35.0 mmol, 1.07 eq.) in THF was added. The reaction mixture was stirred under inert atmosphere for 6 h at 0° C. The reaction was concentrated in vacuo and filtered over a pad of alumina (hexanes/EtOAc 9:1) to afford 2 as a pale yellow oil which was used without further purification (10.26 g, 95%).

4-Furan-3-yl-3,6-dihydro-2H-pyridine-1-carboxylic acid tert-butyl ester (4). A flask was charged with boronic acid 3 (6.22 g, 55.6 mmol), triflate 2 (55.27 g, 166.8 mmol, 3 eq.), lithium chloride (7.07 g, 166.8 mmol, 3 eq.), aqueous 2N $Na_2CO_3$ (56 mL), 1,2-dimethoxyethane (120 mL) and $Pd(PPh_3)_4$ (3.21 g, 2.8 mmol, 0.05 eq.). The reaction mixture was heated to reflux under inert atmosphere for 4 h. After cooling to room temperature the reaction mixture was concentrated under reduced pressure. The resulting residue was partitioned between dichloromethane (150 mL), aqueous 2N $Na_2CO_3$ (125 mL), and concentrated ammonium hydroxide (9 mL). The layers were separated and the aqueous layer extracted again with dichloromethane (3×125 mL). The combined organics were dried over anhydrous magnesium sulfate and concentrated in vacuo. The resulting residue was purified via flash column chromatography (hexanes/$CH_2Cl_2$/EtOAc 9:1:1) to yield 4 as a light yellow oil (8.13 g, 59%). TLC $R_f$=0.43; 400 MHz $^1$H-NMR ($CDCl_3$) δ 1.48 (s, 9H), 2.37 (s, 2H), 3.60 (t, J=3.6 Hz, 2H), 4.03 (s, 2H), 5.87 (s, 1H), 6.51 (s, 1H), 7.38 (d, J=6.8 Hz, 2H); 125 MHz $^{13}$C-NMR ($CDCl_3$) δ 26.9, 39.5 (broad), 40.8 (broad), 43.6 (broad), 79.7, 107.2, 118.7 (broad), 126.8, 138.1, 143.5, 154.9. HRMS Calcd. for $C_{14}H_{19}NO_3Na$ [M$^+$+Na]: 272.1263. Found: 272.1271.

4-Furan-3-yl-3-hydroxy-piperidine-1-carboxylic acid tert-butyl ester (5). To a solution of 4 (2.33 g, 9.358 mmol) in THF (10 mL) at 0° C. borane-tetrahydrofuran, $BH_3$-THF (28.07 mL, 28.07 mmol, 3 eq., 1M sol. in THF) was added dropwise. After stirring the reaction mixture under inert atmosphere at room temperature for 3 h, the unreacted borane was quenched by the addition of methyl alcohol (30 mL). After quenching, 3N NaOH (30 mL) was added slowly to the reaction mixture. This was followed by the addition of 30% $H_2O_2$ (15 mL). The reaction mixture was stirred under inert atmosphere for 16 h. Solvents were removed under reduced pressure and the crude mixture was dissolved in ethyl acetate (60 mL). The ethyl acetate solution was washed with water (40 mL), bicarbonate solution (40 mL), water (40 mL), and brine (40 mL), dried over anhydrous magnesium sulfate and filtered. Removal of solvent at reduced pressure yielded the pure, white, crystalline solid 5 (2.18 g, 87%). TLC $R_f$=0.48 (95% $CH_2Cl_2$—MeOH); 400 MHz $^1$H-NMR ($CDCl_3$) δ 1.47 (s, 9H), 1.57-1.69 (m, 1H), 1.82-1.85 (m, 0.5H), 1.86-1.88 (m, 0.5H), 2.50 (ddd, J=12.4, 10.0, 4.0 Hz, 1H), 2.62 (t, J=10.8 Hz, 1H), 2.76 (m, 1H), 3.47 (m, 1H), 4.12 (m, 1H), 4.32 (m, 1H), 6.35 (s, 1H), 7.38 (d, J=18.8 Hz, 2H); 125 MHz $^{13}$C-NMR ($CDCl_3$) δ 14.4, 20.2, 28.6, 40.2, 60.1, 70.1, 80.1, 109.5, 126.0, 139.7, 143.6, 154.9. HRMS Calcd. for $C_{14}H_{21}NO_4Na$ [M$^+$+Na]: 290.1368. Found: 290.1368.

General procedure for alkylation reactions (88-103). To a stirred suspension of sodium hydride (1.3 eq., 60% suspension in mineral oil) in dimethylformamide (8 mL) at 0° C. was added the alcohol 5 (usually 0.10 g, 0.4 mmol). Following stirring under inert atmosphere at room temperature for 1 h benzyl bromide (3 eq.) was added. The reaction mixture was heated to 40° C. and stirred under inert atmosphere for 48 h. To the reaction mixture was added ethyl acetate (40 mL) and water (20 mL). The layers were separated and the organic layer dried over anhydrous magnesium sulfate, and concentrated in vacuo. Purification by flash column chromatography (hexanes/EtOAc 5:1) yielded pure products 88-103 (Table 1).

TABLE 1

Yields and product characterization for the alkylation reaction.

| # | Name | % Yield | Calcd. HRMS | Found HRMS |
|---|---|---|---|---|
| 88 | 3-Benzyloxy-4-furan-3-yl-piperidine-1-carboxylic acid tert-butyl ester | 41 | 380.1838 [M$^+$ + Na] | 380.1840 |
| 89 | 3-(Biphenyl-4-ylmethoxy)-4-furan-3-yl-piperidine-1-carboxylic acid tert-butyl ester | 43 | 456.2151 [M$^+$ + Na] | 456.2146 |
| 90 | 4-Furan-3-yl-3-(naphthalen-2-ylmethoxy)-piperidine-1-carboxylic acid tert-butyl ester | 6 | 430.1994 [M$^+$ + Na] | 430.2094 |
| 91 | 4-Furan-3-yl-3-(naphthalen-1-ylmethoxy)-piperidine-1-carboxylic acid tert-butyl ester | 43 | 430.1994 [M$^+$ + Na] | 430.1988 |
| 92 | 4-Furan-3-yl-3-(4-phenoxy-benzyloxy)-piperidine-1-carboxylic acid tert-butyl ester | 56 | 472.2100 [M$^+$ + Na] | 472.2110 |
| 93 | 3-(4-tert-Butyl-benzyloxy)-4-furan-3-yl-piperidine-1-carboxylic acid tert-butyl ester | 68 | 436.2464 [M$^+$ + Na] | 436.2464 |
| 94 | 3-(Anthracen-9-ylmethoxy)-4-furan-3-yl-piperidine-1-carboxylic acid tert-butyl ester | 29 | 480.2151 [M$^+$ + Na] | 480.2159 |
| 95 | 4-Furan-3-yl-3-(3-methyl-benzyloxy)-piperidine-1-carboxylic acid tert-butyl ester | 74 | 394.1994 [M$^+$ + Na] | 394.2002 |
| 96 | 3-(3,5-Dimethoxy-benzyloxy)-4-furan-3-yl-piperidine-1-carboxylic acid tert-butyl ester | 59 | 440.2049 [M$^+$ + Na] | 440.2053 |
| 97 | 3-(4-Bromo-benzyloxy)-4-furan-3-yl-piperidine-1-carboxylic acid tert-butyl ester | 66 | 458.0943 [M$^+$ + Na] | 458.0966 |
| 98 | 4-Furan-3-yl-3-(4-methanesulfonyl-benzyloxy)-piperidine-1-carboxylic acid tert-butyl ester | 32 | 458.1613 [M$^+$ + Na] | 458.1633 |
| 99 | 4-Furan-3-yl-3-(2-methyl-allyloxy)-piperidine-1-carboxylic acid tert-butyl ester | 38 | 344.1838 [M$^+$ + Na] | 344.1831 |
| 100 | 3-Cyclohexylmethoxy-4-furan-3-yl-piperidine-1-carboxylic acid tert-butyl ester | 4 | 386.2307 [M$^+$ + Na] | 386.2306 |
| 101 | 3-(2-Cyclohexyl-ethoxy)-4-furan-3-yl-piperidine-1-carboxylic acid tert-butyl ester | 41 | 400.2461 [M$^+$ + Na] | 400.2455 |
| 102 | 4-Furan-3-yl-3-isobutoxy-piperidine-1-carboxylic acid tert-butyl ester | 9 | 346.1994 [M$^+$ + Na] | 346.1981 |
| 103 | 3-(2-Ethyl-butoxy)-4-furan-3-yl-piperidine-1-carboxylic acid tert-butyl ester | 4 | 374.2307 [M$^+$ + Na] | 374.2304 |

General procedure for $^t$Boc removal reaction (104-118). To 88-103 (usually 0.05 g) was added 4N HCl-dioxane (3 mL). The reaction mixture was stirred under inert atmosphere at room temperature for 30 min. Removal of solvent at reduced pressure followed by trituration with diethyl ether yielded pure products 104-118 (Table 2).

TABLE 2

Yields and product characterization for the ⁱBoc deprotection reaction.

| # | Name | % Yield | Calcd. HRMS | Found HRMS |
|---|------|---------|-------------|------------|
| 104 | 3-Benzyloxy-4-furan-3-yl-piperidine | 85 | 280.1313 [M⁺ + Na] | 280.1316 |
| 105 | 3-(Biphenyl-4-ylmethoxy)-4-furan-3-yl-piperidine | 98 | 334.1807 [M⁺ + H] | 334.1806 |
| 106 | 4-Furan-3-yl-3-(naphthalen-2-ylmethoxy)-piperidine | 99 | 330.1470 [M⁺ + Na] | 330.1463 |
| 107 | 4-Furan-3-yl-3-(naphthalen-1-ylmethoxy)-piperidine | 99 | 308.1650 [M⁺ + H] | 308.1651 |
| 108 | 4-Furan-3-yl-3-(4-phenoxy-benzyloxy)-piperidine | 99 | 350.1756 [M⁺ + H] | 350.1767 |
| 109 | 3-(4-tert-Butyl-benzyloxy)-4-furan-3-yl-piperidine | 89 | 314.2120 [M⁺ + H] | 314.2125 |
| 110 | 3-(Anthracen-9-ylmethoxy)-4-furan-3-yl-piperidine | 52 | 358.1807 [M⁺ + H] | 358.1815 |
| 111 | 4-Furan-3-yl-3-(3-methyl-benzyloxy)-piperidine | 99 | 272.1650 [M⁺ + H] | 272.1639 |
| 112 | 3-(3,5-Dimethoxy-benzyloxy)-4-furan-3-yl-piperidine | 99 | 318.1705 [M⁺ + H] | 318.1703 |
| 113 | 3-(4-Bromo-benzyloxy)-4-furan-3-yl-piperidine | 99 | 336.0599 [M⁺ + H] | 336.0610 |
| 114 | 4-Furan-3-yl-3-(2-methyl-allyloxy)-piperidine | 98 | 222.1494 [M⁺ + H] | 222.1498 |
| 115 | 3-Cyclohexylmethoxy-4-furan-3-yl-piperidine | 99 | 264.1963 [M⁺ + H] | 264.1950 |
| 116 | 3-(2-Cyclohexyl-ethoxy)-4-furan-3-yl-piperidine | 58 | 278.2120 [M⁺ + H] | 278.2126 |
| 117 | 4-Furan-3-yl-3-isobutoxy-piperidine | 73 | 224.1650 [M⁺ + H] | 224.1658 |
| 118 | 3-(2-Ethyl-butoxy)-4-furan-3-yl-piperidine | 93 | 252.1964 [M⁺ + H] | |

Examples for alkylation and ⁱBoc Deprotection Reactions:

3-Benzyloxy-4-furan-3-yl-piperidine-1-carboxylic acid tert-butyl ester (88). To a stirred suspension of sodium hydride (0.02 g, 0.5 mmol, 1.3 eq., 60% suspension in mineral oil) in dimethylformamide (8 mL) at 0° C. was added the alcohol 5 (0.10 g, 0.4 mmol). Following stirring under inert atmosphere at room temperature for 1 h benzyl bromide (0.13 mL, 1.1 mmol, 3 eq.) was added. The reaction mixture was heated to 40° C. and stirred under inert atmosphere for 48 h. To the reaction mixture was added ethyl acetate (40 mL) and water (20 mL). The layers were separated and the organic layer dried over anhydrous magnesium sulfate, and concentrated in vacuo. Purification by flash column chromatography (hexanes/EtOAc 5:1) yielded clear viscous liquid 6 (0.05 g, 41%). TLC $R_f$=0.22; 400 MHz ¹H-NMR (CDCl₃) δ 1.47 (S, 9H), 1.62 (ddd, J=16.8, 12.4, 4.4 Hz, 1H), 1.89 (m, 1H), 2.66 (m, 2H), 2.79 (t, J=12.4 Hz, 1H), 3.25 (s, 1H), 4.06 (m, 1H), 4.38 (d, J=11.2 Hz, 2H), 4.53 (s, 1H), 6.33 (s, 1H), 7.19 (d, J=7.2 Hz, 2H), 7.27 (m, 4H), 7.37 (s, 1H); 125 MHz ¹³C-NMR (CDCl₃) δ 28.6, 39.5, 72.1, 78.1, 78.0, 110.2, 126.5, 127.8, 128.0, 129.0, 138.3, 139.4, 142.8. HRMS Calcd. for C₂₁H₂₇NO₄Na [M⁺+Na]: 380.1838. Found: 380.1840.

3-(Biphenyl-4-ylmethoxy)-4-furan-3-yl-piperidine-1-carboxylic acid tert-butyl ester (89). Clear viscous liquid (43%). TLC $R_f$=0.21; 400 MHz ¹H-NMR (CDCl₃) δ 1.47 (s, 9H), 1.64 (m, 1H), 1.89 (m, 1H), 2.66 (m, 2H), 2.80 (t, J=12.0 Hz, 1H), 3.29 (s, 1H), 4.06 (m, 1H), 4.42 (d, J=11.2 Hz, 2H), 4.57 (s, 1H), 6.35 (s, 1H), 7.27 (m, 2H), 7.33 (m, 2H), 7.38 (m, 1H), 7.42 (m, 2H), 7.56 (m, 4H); 125 MHz ¹³C-NMR (CDCl₃) δ 28.6, 39.5, 71.9, 78.2, 80.0, 110.3, 126.5, 127.2, 127.3, 127.4, 128.4, 128.9,4, 137.3, 139.4, 140.8, 141.0, 142.8, 154.8. HRMS Calcd. for C₂₇H₃₁NO₄Na [M⁺+Na]: 456.2151. Found: 456.2146.

4-Furan-3-yl-3-(naphthalen-2-ylmethoxy)-piperidine-1-carboxylic acid tert-butyl ester (90). Clear viscous liquid (6%). TLC $R_f$=0.27; 400 MHz ¹H-NMR (CDCl₃) δ 1.44 (s, 9H), 1.63 (m, 1H), 1.89 (m, 1H), 2.69 (m, 2H), 2.80 (m, 1H), 3.30 (s, 1H), 4.09 (m, 1H), 4.54 (d, J=11.6 Hz, 2H), 4.68 (m, 1H), 6.33 (s, 1H), 7.25 (m, 1H), 7.28 (d, J=8.4 Hz, 2H), 7.32 (m, 2H), 7.62 (s, 1H), 7.78 (m, 3H); 125 MHz ¹³C-NMR (CDCl₃) δ 28.6, 39.6, 72.2, 78.2, 80.0, 110.3, 125.9, 126.0, 126.2, 126.5, 126.6, 127.8, 128.1, 128.3, 133.2, 133.4, 135.8, 139.5, 142.8. HRMS Calcd. for C₂₅H₂₉NO₄Na [M⁺+Na]: 430.1994. Found: 430.2094.

4-Furan-3-yl-3-(naphthalen-1-ylmethoxy)-piperidine-1-carboxylic acid tert-butyl ester (91). Clear viscous liquid (43%). TLC $R_f$=0.12; 400 MHz ¹H-NMR (CDCl₃) δ 1.46 (s, 9H), 1.63 (m, 1H), 1.86 (m, 1H), 2.65 (m, 2H), 2.77 (m, 1H), 3.36 (s, 1H), 4.06 (m, 1H), 4.51-5.12 (m, 3H), 6.26 (s, 1H), 7.27 (d, J=27.2 Hz, 2H), 7.40 (m, 3H), 7.78 (m, 4H); 125 MHz ¹³C-NMR (CDCl₃) δ 28.6, 39.5, 70.7, 78.1, 80.0, 109.9, 124.3, 125.3, 125.9, 126.2, 126.4, 126.9, 128.5, 129.0, 131.9, 133.6, 133.9, 139.5, 142.8. HRMS Calcd. for C₂₅H₂₉NO₄Na [M⁺+Na]: 430.1994. Found: 430.1988.

4-Furan-3-yl-3-(4-phenoxy-benzyloxy)-piperidine-1-carboxylic acid tert-butyl ester (92). Clear viscous liquid (56%). TLC $R_f$=0.16; 400 MHz ¹H-NMR (CDCl₃) δ 1.46 (s, 9H), 1.61 (m, 1H), 1.85 (m, 1H), 2.62 (m, 2H), 2.78 (t, J=12 Hz, 1H), 3.23 (m, 1H), 4.04 (m, 1H), 4.33 (d, J=11.6 Hz, 2H), 4.51 (m, 1H), 6.28 (s, 1H), 6.89 (m, 3H), 6.99 (m, 2H), 7.09 (t, J=7.2 Hz, 1H), 7.28 (m, 5H); 125 MHz ¹³C-NMR (CDCl₃) δ 28.6, 39.4, 71.6, 78.4, 80.0, 110.2, 118.1, 119.0, 122.5, 123.4, 126.4, 129.7, 129.9, 139.3, 140.4, 142.8, 154.7, 157.3, 157.5. HRMS Calcd. for C₂₇H₃₁NO₅Na [M⁺+Na]: 472.2100. Found: 472.2110.

3-(4-tert-Butyl-benzyloxy)-4-furan-3-yl-piperidine-1-carboxylic acid tert-butyl ester (93). Clear viscous liquid (68%). TLC $R_f$=0.21; 400 MHz ¹H-NMR (CDCl₃) δ 1.32 (s, 9H), 1.49 (s, 9H), 1.64 (ddd, J=16.8, 12.4, 4.4 Hz, 1H), 1.90 (m, 1H), 2.66 (m, 2H), 2.80 (t, J=12.4 Hz, 1H), 3.27 (s, 1H), 4.09 (m, 1H), 4.36 (d, J=10.8 Hz, 2H), 4.52 (m, 1H), 6.36 (s, 1H), 7.15 (d, J=8.0 Hz, 2H), 7.33 (m, 3H), 7.38 (t, J=1.6 Hz, 1H); 125 MHz ¹³C-NMR (CDCl₃) δ 14.3, 22.8, 28.6, 31.5, 34.7, 39.5, 72.0, 78.1, 80.0, 110.2, 125.4, 126.5, 127.8, 135.2, 139.4, 142.7, 150.763, 154.8. HRMS Calcd. for C₂₅H₃₅NO₄Na [M⁺+Na]: 436.2464. Found: 436.2464.

3-Benzyloxy-4-furan-3-yl-piperidine (104). To 6 (0.07 g, 0.2 mmol) was added 4N HCl-dioxane (4 mL). The reaction mixture was stirred under inert atmosphere for 30 min. Removal of solvent at reduced pressure followed by trituration with diethyl ether yielded pure, crystaline 22 (0.05 g, 85%); 400 MHz ¹H-NMR (CD₃OD) δ 2.02 (m, 1H), 2.22 (m, 1H), 2.99 (m, 2H), 3.12 (m, 1H), 3.60 (m, 0.5H), 3.68 (m, 1H), 3.75 (m, 0.5H), 3.82 (td, J 8.4, 3.6 Hz, 1H), 4.60 (d, J=11.2 Hz, 1H), 4.51 (d, J=11.2 Hz, 1H), 6.46 (s, 1H), 7.30 (m, 5H), 7.49 (m, 2H); 125 MHz ¹³C-NMR (CD₃OD) δ 27.4, 37.2, 43.8, 46.8, 73.9, 75.8, 104.2, 110.9, 129.1, 129.2, 129.5, 139.2, 141.2, 144.6. HRMS Calcd. for C₁₆H₁₉NO₂Na [M⁺+Na]: 280.1313. Found: 280.1316.

3-(Biphenyl-4-ylmethoxy)-4-furan-3-yl-piperidine (105). Solid (98%); 400 MHz ¹H-NMR (CD₃OD) δ 2.02 (m, 1H), 2.22 (m, 1H), 2.99 (m, 2H), 3.11 (m, 1H), 3.59 (m, 0.5H), 3.66 (m, 1H), 3.74 (m, 0.5H), 3.82 (m, J=8.0, 3.2 Hz, 1H), 4.54 (d, J=11.6 Hz, 1H), 4.62 (d, J=11.6 Hz, 1H), 6.46 (s, 1H), 7.34 (m, 2H), 7.43 (m, 3H); 7.49 (m, 2H), 7.58 (m, 4H); 125 MHz ¹³C-NMR (CD₃OD) δ 27.4, 37.2, 43.8, 46.8, 73.1, 75.8, 110.9, 128.0, 128.1, 128.6, 129.8, 130.0, 141.2, 144.7. HRMS Calcd. for $C_{22}H_{24}NO_2$ [M$^+$+H]: 334.1807. Found: 334.1806.

4-Furan-3-yl-3-(naphthalen-2-ylmethoxy)-piperidine (106). Solid (99%); 400 MHz $^1$H-NMR (CD$_3$OD) δ 1.99 (m, 1H), 2.24 (m, 1H), 3.03 (m, 2H), 3.11 (m, 1H), 3.59 (m, 0.5H), 3.67 (m, 1H), 3.75 (m, 0.5H), 3.83 (td, J=8.0, 3.2 Hz, 1H), 4.69 (d, J=11.6 Hz, 1H), 4.76 (d, J=11.6 Hz, 1H), 6.44 (s, 1H), 7.38 (d, J=8.4 Hz, 2H), 7.49 (m, 4H); 7.74 (s, 1H), 7.83 (m, 3H); 125 MHz $^{13}$C-NMR (CD$_3$OD) δ 27.3, 37.1, 43.8, 46.9, 68.2, 73.4, 110.8, 127.0, 127.2, 127.9, 128.7, 129.0, 129.2, 134.7, 141.2, 144.6. HRMS Calcd. for $C_{20}H_{21}NO_2$ [M$^+$+Na]: 330.1470. Found: 330.1463.

4-Furan-3-yl-3-(naphthalen-1-ylmethoxy)-piperidine (107). Solid (99%); 400 MHz $^1$H-NMR (CD$_3$OD) δ 1.98 (m, 1H), 2.12 (m, 1H), 2.91 (m, 2H), 3.03 (m, 1H), 3.46 (m, 1H), 3.63 (s, 1H), 3.86 (m, 1H), 4.91 (d, J=11.6 Hz, 1H), 4.96 (d, J=11.6 Hz, 1H), 6.36 (s, 1H), 7.42 (m, 5H), 7.84 (m, 3H); 125 MHz $^{13}$C-NMR (CD$_3$OD) δ 27.8, 37.4, 43.9, 47.0, 68.2, 71.9, 75.7, 110.6, 125.3, 126.3, 127.0, 127.3, 128.4, 130.0, 130.2, 134.4, 135.3, 141.3, 144.6. HRMS Calcd. for $C_{20}H_{21}NO_2$ [M$^+$+H]: 308.1650. Found: 308. 1651.

4-Furan-3-yl-3-(4-phenoxy-benzyloxy)-piperidine(108). Solid (99%); 400 MHz $^1$H-NMR (CD$_3$OD) δ 1.99 (m, 1H), 2.17 (m, 1H), 2.96 (m, 2H), 3.08 (m, 1H), 3.49 (m, 1H), 3.65 (s, 1H), 3.78 (m, 1H), 4.45 (d, J=11.6 Hz, 1H), 4.57 (d, J=11.6 Hz, 1H), 6.39 (s, 1H), 6.95 (m, 5H), 7.10 (t, J=7.2 Hz, 1H), 7.32 (m, 4H), 7.42 (s, 1H); 125 MHz $^{13}$C-NMR (CD$_3$OD) δ 27.4, 37.2, 43.9, 46.8, 72.9, 76.0, 110.8, 119.2, 119.3, 120.0, 123.8, 124.6, 125.9, 130.7, 131.0, 141.2, 141.3, 144.6, 158.6, 159.0. HRMS Calcd. for $C_{22}H_{24}NO_3$ [M$^+$+H]: 350.1756. Found: 350.1767.

3-(4-tert-Butyl-benzyloxy)-4-furan-3-yl-piperidine(109). Solid (89%); 400 MHz $^1$H-NMR (CD$_3$OD) δ 1.99 (m, 1H), 2.23 (m, 1H), 2.98 (m, 2H), 3.10 (m, 1H), 3.45 (m, 1H), 3.67 (s, 1H), 3.78 (m, 1H), 4.49 (d, J=11.6 Hz, 1H), 4.55 (d, J=11.6 Hz, 1H), 6.43 (s, 1H), 7.20 (d, J=8.0 Hz, 2H), 7.37 (d, J=8 Hz, 4H), 7.47 (d, J=15.6 Hz, 1H); 125 MHz $^{13}$C-NMR (CD$_3$OD) δ 27.3, 31.9, 35.5, 37.1, 43.8, 46.9, 68.3, 73.2, 75.5, 110.9, 126.0, 126.4, 129.2, 136.1, 141.2, 144.7, 152.3. HRMS Calcd. for $C_{20}H_{28}NO_2$ [M$^+$+H]: 314.2120. Found: 314.2125.

| Table of compounds |
|---|
| Products of alkylation reactions (88-103) |
| 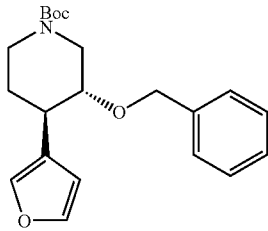 |
| 3-Benzyloxy-4-furan-3-yl-piperidine-1-carboxylic acid tert-butyl ester, 88, Exact Mass: 357.1940 |

| Table of compounds |
|---|
| *-continued* |
| 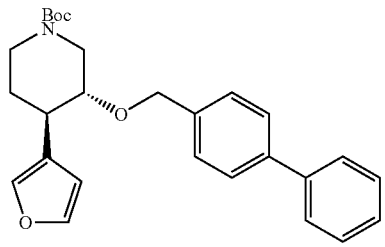 |
| 3-(Biphenyl-4-ylmethoxy)-4-furan-3-yl-piperidine-1-carboxylic acid tert-butyl ester, 89, Exact Mass: 433.2253 |
| 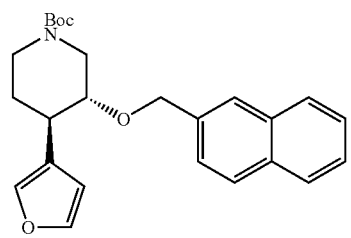 |
| 4-Furan-3-yl-3-(naphthalen-2-ylmethoxy)-piperidine-1-carboxylic acid tert-butyl ester, 90, Exact Mass: 407.2097 |
| 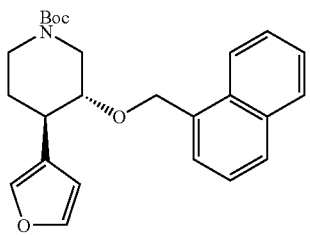 |
| 4-Furan-3-yl-3-(naphthalen-1-ylmethoxy)-piperidine-1-carboxylic acid tert-butyl ester, 91, Exact Mass: 407.2097 |
| 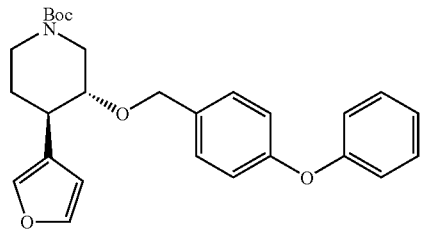 |
| 4-Furan-3-yl-3-(4-phenoxy-benzyloxy)-piperidine-1-carboxylic acid tert-butyl ester, 92, Exact Mass: 449.2202 |

Table of compounds

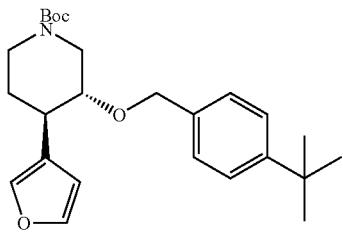

3-(4-tert-Butyl-benzyloxy)-4-
furan-3-yl-piperidine-1-
carboxylic acid tert-butyl ester, 93,
Exact Mass: 313.2042

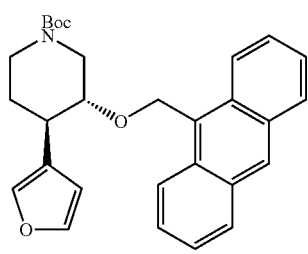

3-(Anthracen-9-ylmethoxy)-
4-furan-3-yl-piperidine-1-
carboxylic acid tert-butyl ester, 94,
Exact Mass: 457.2253

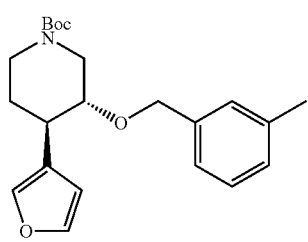

4-Furan-3-yl-3-(3-methyl-
benzyloxy)-piperidine-1-
carboxylic acid tert-butyl ester, 95,
Exact Mass: 371.2097

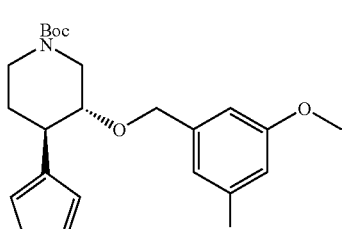

3-(3,5-Dimethoxy-benzyloxy)-
4-furan-3-yl-piperidine-1-
carboxylic acid tert-butyl ester, 96,
Exact Mass: 417.2151

Table of compounds

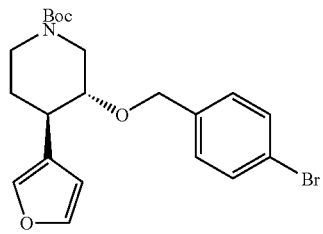

3-(4-Bromo-benzyloxy)-4-furan-
3-yl-piperidine-1-carboxylic
acid tert-butyl ester, 97,
Exact Mass: 435.1045

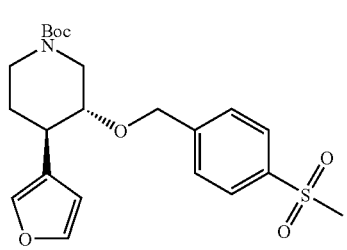

4-Furan-3-yl-3-(4-methane
sulfonyl-benzyloxy)-piperidine-
1-carboxylic acid tert-butyl ester, 98,
Exact Mass: 435.1716

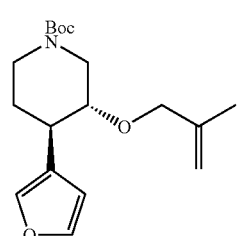

4-Furan-3-yl-3-(2-methyl-allyloxy)-
piperidine-1-carboxylic acid
tert-butyl ester, 99,
Exact Mass: 321.1940

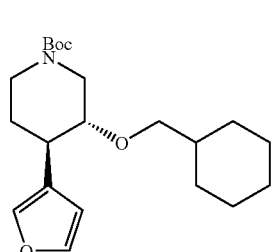

3-Cyclohexylmethoxy-4-
furan-3-yl-piperidine-1-
carboxylic acid tert-butyl ester, 100,
Exact Mass: 363.2410

Table of compounds

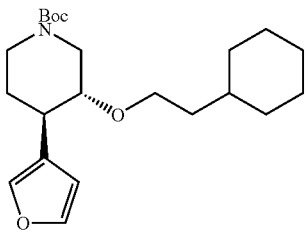

3-(2-Cyclohexyl-ethoxy)-
4-furan-3-yl-piperidine-1-
carboxylic acid tert-butyl ester, 101,
Exact Mass: 377.2566

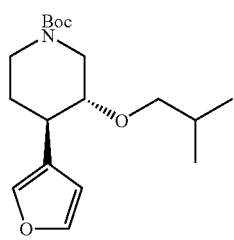

4-Furan-3-yl-3-isobutoxy-
piperidine-1-carboxylic
acid tert-butyl ester, 102,
Exact Mass: 323.2097

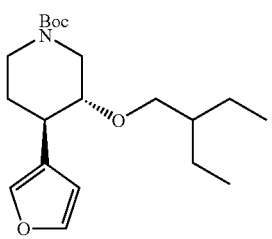

3-(2-Ethyl-butoxy)-4-furan-
3-yl-piperidine-1-carboxylic
acid tert-butyl ester, 103,
Exact Mass: 351.4804

Products of ¹Boc deprotection reactions (104-118)

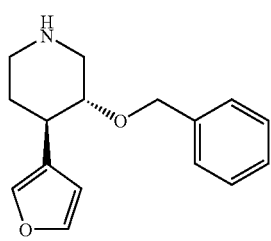

3-Benzyloxy-4-furan-3-
yl-piperidine, 104,
Exact Mass: 257.1416

Table of compounds

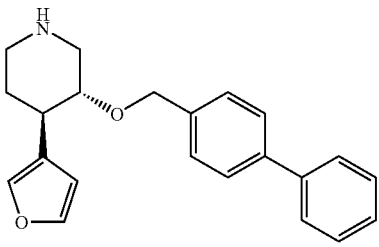

3-(Biphenyl-4-ylmethoxy)-4-
furan-3-yl-piperidine, 105,
Exact Mass: 333.1729

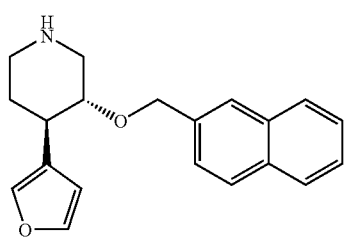

4-Furan-3-yl-3-(naphthalen-2-
ylmethoxy)-piperidine, 106,
Exact Mass: 307.1572

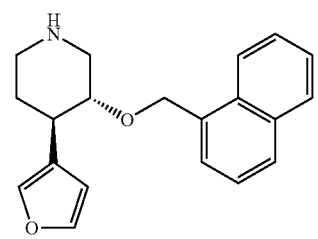

4-Furan-3-yl-3-(naphthalen-1-
ylmethoxy)-piperidine, 107,
Exact Mass: 307.1572

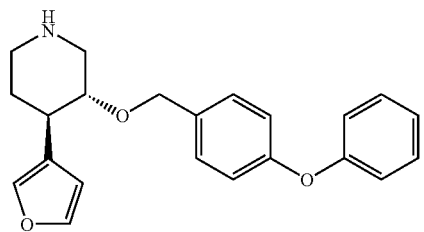

4-Furan-3-yl-3-(4-phenoxy-
benzyloxy)piperidine, 108,
Exact Mass: 349.1678

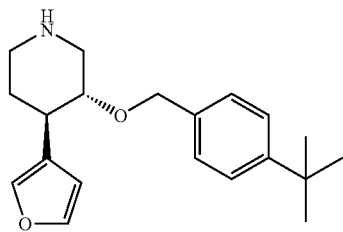

3-(4-tert-Butyl-benzyloxy)-4-

| Table of compounds |
|---|
| furan-3-yl-piperidine, 109,<br>Exact Mass: 313.2042 |
| 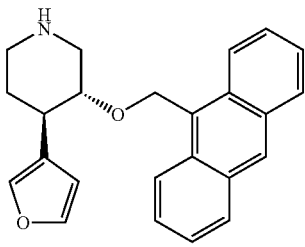<br>3-(Anthracen-9-ylmethoxy)-4-<br>furan-3-yl-piperidine, 110,<br>Exact Mass: 357.1729 |
| 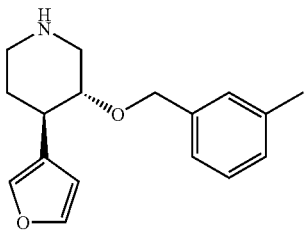<br>4-Furan-3-yl-3-(3-methyl-<br>benzyloxy)-piperidine, 111,<br>Exact Mass: 271.1572 |
| 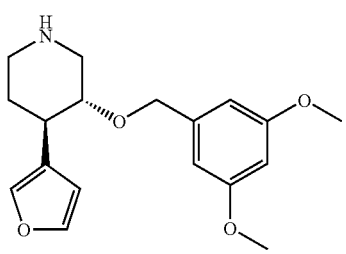<br>3-(3,5-Dimethoxy-benzyloxy)-4-<br>furan-3-yl-piperidine, 112,<br>Exact Mass: 317.1627 |
| 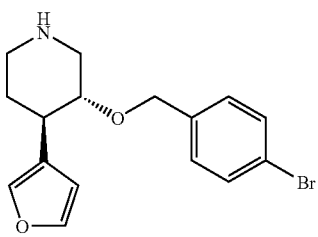<br>3-(4-Bromo-benzyloxy)-4-<br>furan-3-yl-piperidine, 113,<br>Exact Mass: 335.0521 |

| Table of compounds |
|---|
| 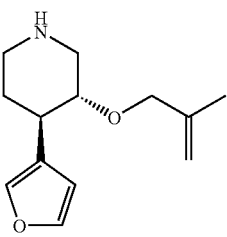<br>4-Furan-3-yl-3-(2-methyl-<br>allyloxy)-piperidine, 114,<br>Exact Mass: 221.1416 |
| 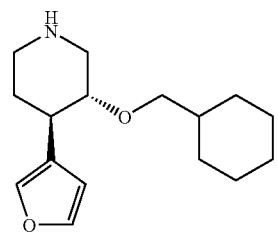<br>3-Cyclohexylmethoxy-4-furan-3-<br>yl-piperidine, 115,<br>Exact Mass: 263.1885 |
| 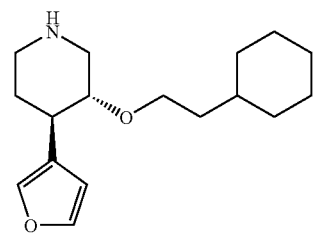<br>3-(2-Cyclohexyl-ethoxy)-4-<br>furan-3-yl-piperidine, 116,<br>Exact Mass: 277.2042 |
| 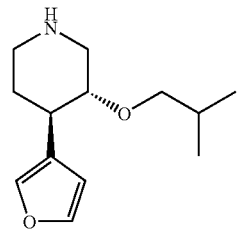<br>4-Furan-3-yl-3-isobutoxy-<br>piperidine, 117<br>Exact Mass: 223.1572 |

-continued

Table of compounds

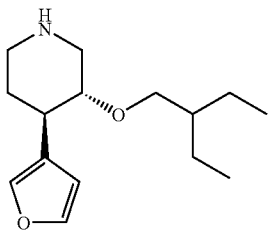

3-(2-Ethyl-butoxy)-4-furan-3-
yl-piperidine, 118,
Exact Mass: 251.1885

BIOLOGY EXAMPLES

Without further elaboration, it is believed that one skilled in the art can, using the preceding description, practice the invention to its fullest extent. The invention, however, may be better understood with reference to the following examples. These examples are intended to be representative of specific embodiments of the invention, and are not intended as limiting the scope of the invention.

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al, 1999, *Nature* 40:537-540) or recombinantly produced as the full-length enzyme (amino acids 1-501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaOAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an IC50 of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
                                            [SEQ ID NO: 1]
Biotin-SEVNL-DAEFRC[Oregon green]KK

[SEQ ID NO: 2]
Biotin-SEVKM-DAEFRC[Oregon green]KK

[SEQ ID NO: 3]
Biotin-GLNIKTEEISEISY-EVEFRC[Oregon green]KK

[SEQ ID NO: 4]
Biotin-ADRGLTTRPGSGLTNIKTEEISEVNLDAEFRC
[Oregon green]KK

[SEQ ID NO: 5]
Biotin-FVNQHLCoxGSHLVEALYLVCoxGERGFFYTPKA
[Oregon green]KK
```

The enzyme (0.1 nanomolar) and test compounds (0.001-100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001-100 micromolar compound inhibitor; 0.1 molar sodium acetate (pH 4.5); 150 nanomolar substrate;

0.1 nanomolar soluble beta-secretase; 0.001% Tween 20, and 2% DMSO. The assay mixture is incubated for 3 hours at 37 degrees C, and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm) The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an $IC_{50}$ of less than 50 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618. The P26-P4'SW substrate is a peptide of the sequence:

```
                                           [SEQ ID NO: 6]
(biotin) CGGADRGLTTRPGSGLTNIKTEEISEVNLDAEF The P26-P1 standard has the sequence:
                                           [SEQ ID NO: 7]
(biotin) CGGADRGLTTRPGSGLTNIKTEEISEVNL.
```

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays Using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, *Nature* 360:672-674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, *Nature* 373:523-527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1-30 mg/ml; preferably 1-10 mg/ml). After time, e.g., 3-10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

Example H

Biological Inhibition Activity

The biological activity of the compound prepared according to Example 29 was measured in accordance with the above described procedures

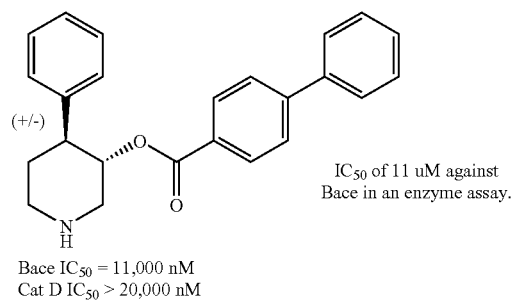

$IC_{50}$ of 11 uM against Bace in an enzyme assay.

Bace $IC_{50}$ = 11,000 nM
Cat D $IC_{50}$ > 20,000 nM

The invention has been described with reference to various specific and preferred embodiments and techniques. However, it should be understood that many variations and modifications may be made while remaining within the spirit and scope of the invention.

What is claimed is:

1. A compound of formula (I):

(I)

[chemical structure: six-membered ring with Z bearing $R_2$, $R_1$ and $R_3$ substituents at positions flanking Z, and NH in the ring]

or a pharmaceutically acceptable salt thereof,
wherein Z is CH;
wherein $R_1$ is
wherein $R_9$ is:
—$R_{C\text{-}aryl}$,
—$R_{C\text{-}aryl}$—$R_{C\text{-}aryl}$, or
—$R_{C\text{-}aryl}$—$R_{C\text{-}heterocycle}$, and where $R_{C\text{-}aryl}$ is phenyl, 1-naphthyl, 2-naphthyl, tetralinyl, indanyl, or dihydronaphthyl, optionally substituted with one, two or three of the following substituents which can be the same or different and are:
(1) $C_1$-$C_6$ alkyl, optionally substituted with one, two or three substituents selected from the group consisting of $C_1$-$C_3$ alkyl, —F, —Cl, —Br, —I, —OH, —SH, —S($C_{1-6}$ alkyl), —SO$_2$ ($C_{1-6}$ alkyl), —C≡N, —CF$_3$, $C_1$-$C_3$ alkoxy, and —NR$_{1\text{-}a}$R$_{1\text{-}b}$, where $R_{1\text{-}a}$ and $R_{1\text{-}b}$ are independently —H or $C_1$-$C_6$ alkyl,
(2) —OH,
(3) —NO$_2$,
(4) —F, —Cl, —Br, —I,
(5) —CO—OH,
(6) —C≡N,
(7) —(CH$_2$)$_{0-4}$—CO—NR$_{N\text{-}2}$R$_{N\text{-}3}$, where $R_{N\text{-}2}$ and $R_{N\text{-}3}$ are independently —H or $C_1$-$C_6$ alkyl,
(8) —(CH$_2$)$_{0-4}$—CO—($C_1$-$C_{12}$ alkyl),
(9) —(CH$_2$)$_{0-4}$—CO—R$_{1\text{-}aryl}$, where R$_{1\text{-}aryl}$ is phenyl,
(10) —(CH$_2$)$_{0-4}$—CO—O—R$_{N\text{-}5}$, where R$_{N\text{-}5}$ is $C_1$-$C_6$ alkyl or —(CH$_2$)$_{0-2}$—(R$_{1\text{-}aryl}$), where R$_{1\text{-}aryl}$ is phenyl.
(11) —(CH$_2$)$_{0-4}$—SO$_2$—($C_1$-$C_{12}$ alkyl),
(12) —(CH$_2$)$_{0-4}$—NR$_{N\text{-}2}$R$_{N\text{-}3}$,
(13) —(CH$_2$)$_{0-4}$—O—CO—($C_1$-$C_6$ alkyl),
(14) —(CH$_2$)$_{0-4}$—O—CO—N(R$_{N\text{-}5}$)$_2$,
(15) —(CH$_2$)$_{0-4}$—O—(R$_{N\text{-}5}$)$_2$,
(16) —(CH$_2$)$_{0-4}$—S—(R$_{N\text{-}5}$)$_2$, or
(17) —(CH$_2$)$_{0-4}$—O—($C_1$-$C_6$ alkyl optionally substituted with one, two, three, four, or five of —F); and $R_{C\text{-}heterocycle}$ is selected from the group consisting of: morpholinyl, thiomorpholinyl, piperazinyl, pyrrolidinyl, pyrrolinyl, tetrahydropyranyl, piperidinyl, tetrahydrofuranyl, and tetrahydrothienyl; and wherein $R_2$ is phenyl, optionally substituted with one, two or three radicals selected from CF$_3$, OCF$_3$, hydroxyl, halo, $C_1$-$C_2$-alkyl, $C_1$-$C_2$-haloalkyl, cyano, carboxyl, $C_1$-$C_2$-alkoxycarbonyl, $C_1$-$C_2$-hydroxyalkyl, thioalkyl, aminosulfonyl, $C_1$-$C_2$-alkylaminosulfonyl, methyl $C_1$-$C_2$-haloalkoxy, amino, $C_1$-$C_2$-alkylamino, phenylamino, nitro, $C_1$-$C_2$-alkoxy-$C_1$-$C_2$-alkyl, $C_1$-$C_2$-alkylsulfinyl, $C_1$-$C_2$-alkoxy and $C_1$-$C_3$-alkylthio.

2. A compound according to claim 1, wherein $R_2$ is an optionally substituted phenol.

3. A compound according to claim 1, having the formula:

[chemical structure: piperidine with NH, bearing a 4-fluorophenyl substituent and an ester-linked biphenylcarboxylate group]

4. A compound according to claim 1, having the formula:

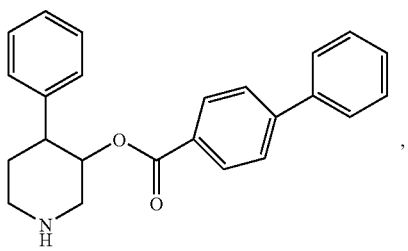
,

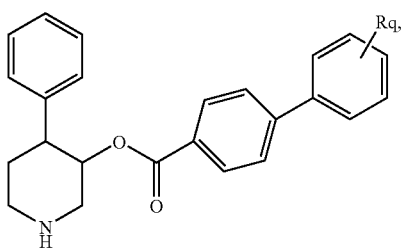

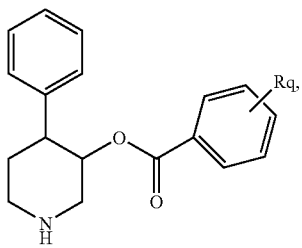

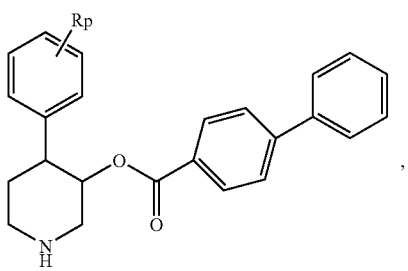
,

-continued

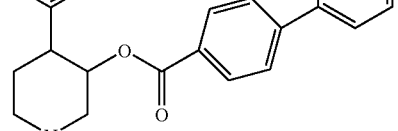 or

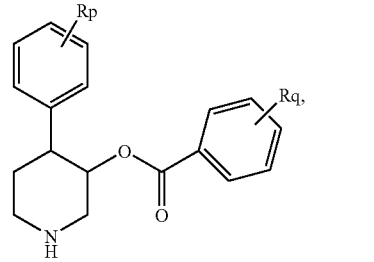

wherein

Rp is one, two or three radicals selected from $CF_3$, $OCF_3$, hydroxyl, halo, $C_1$-$C_2$-alkyl, $C_1$-$C_2$-haloalkyl, cyano, carboxyl, $C_1$-$C_2$-alkoxycarbonyl, $C_1$-$C_2$-hydroxyalkyl, thioalkyl, aminosulfonyl, $C_1$-$C_2$-alkylaminosulfonyl, methyl $C_1$-$C_2$-haloalkoxy, amino, $C_1$-$C_2$-alkylamino, phenylamino, nitro, $C_1$-$C_2$-alkoxy-$C_1$-$C_2$-alkyl, $C_1$-$C_2$-alkylsulfinyl, $C_1$-$C_2$-alkoxy and $C_1$-$C_3$-alkylthio, and Rq is one, two, three or four of the substituents listed as substituents on $R_{C\text{-}aryl}$ in claim 1.

5. A compound or salt of the formula:

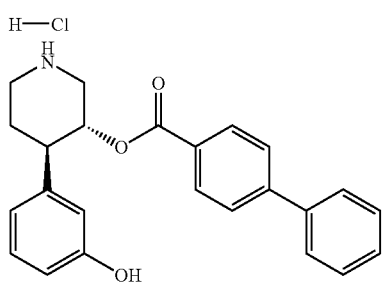

(+/−)-(3R,4R)-4-(3-hydroxyphenyl)piperidin-3-yl 1,1'-biphenyl-4-carboxylate hydrochloride

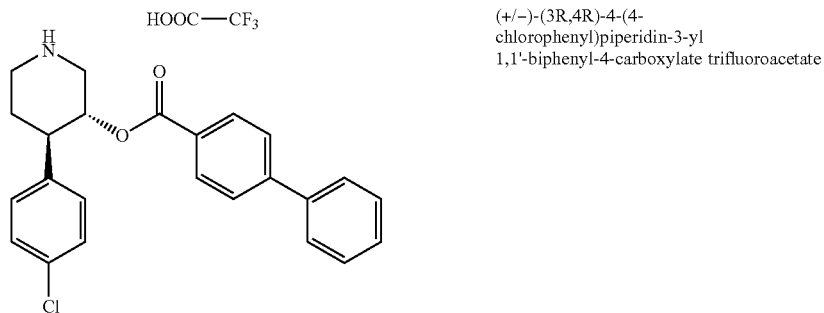
(+/−)-(3R,4R)-4-(4-chlorophenyl)piperidin-3-yl 1,1'-biphenyl-4-carboxylate trifluoroacetate
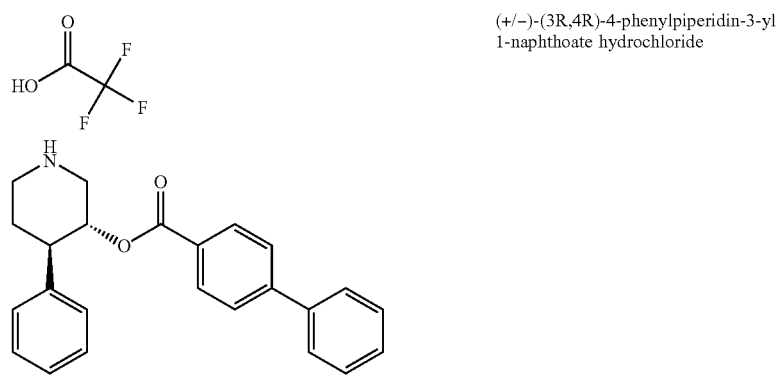
(+/−)-(3R,4R)-4-phenylpiperidin-3-yl 1-naphthoate hydrochloride
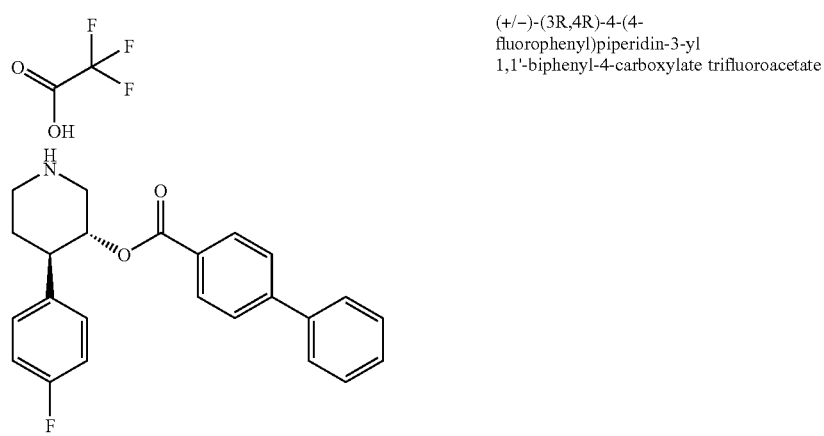
(+/−)-(3R,4R)-4-(4-fluorophenyl)piperidin-3-yl 1,1'-biphenyl-4-carboxylate trifluoroacetate
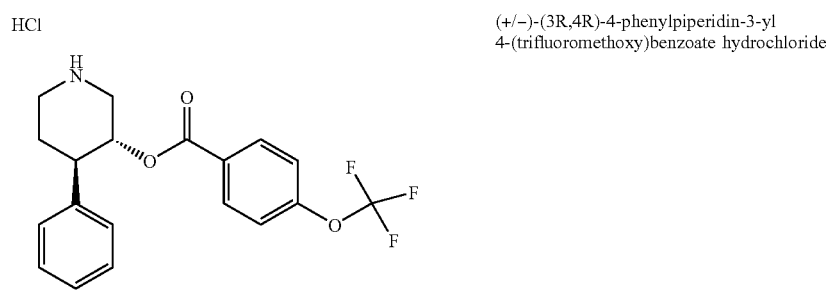
(+/−)-(3R,4R)-4-phenylpiperidin-3-yl 4-(trifluoromethoxy)benzoate hydrochloride

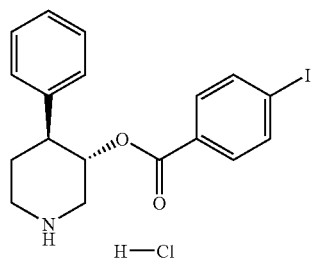 (+/−)-(3S,4S)-4-phenylpiperidin-3-yl 4-iodobenzoate hydrochloride
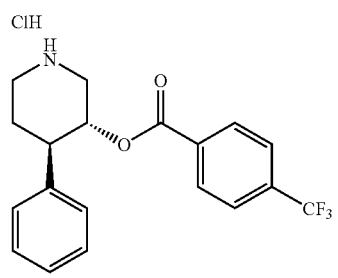 (+/−)-(3R,4R)-4-phenylpiperidin-3-yl 4-(trifluoromethyl)benzoate hydrochloride
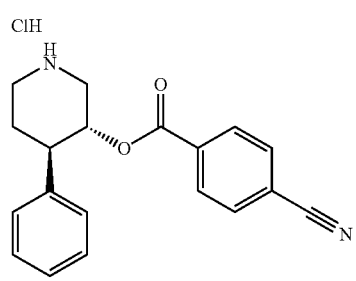 (+/−)-(3R,4R)-4-phenylpiperidin-3-yl 4-cyanobenzoate hydrochloride
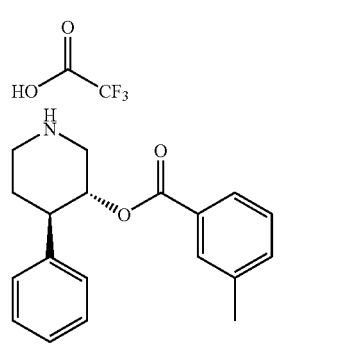 (+/−)-(3R,4R)-4-phenylpiperidin-3-yl 3-methylbenzoate trifluoroacetate
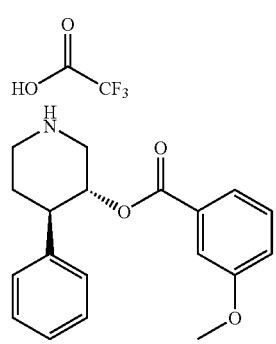 (+/−)-(3R,4R)-4-phenylpiperidin-3-yl 3-methoxybenzoate trifluoroacetate -continued
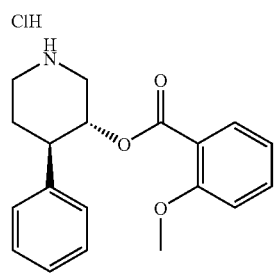
(+/−)-(3R,4R)-4-phenylpiperidin-3-yl 2-methoxybenzoate hydrochloride
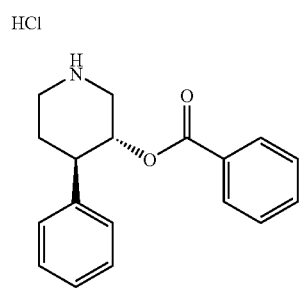
(+/−)-(3R,4R)-4-phenylpiperidin-3-yl benzoate hydrochloride
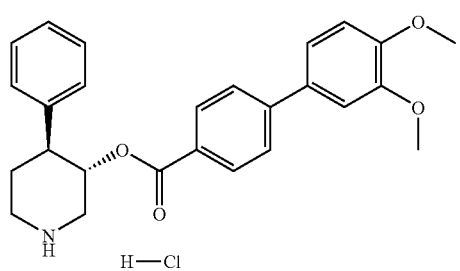
(+/−)-(3S,4S)-4-phenylpiperidin-3-yl 3',4'-dimethoxy-1,1'-biphenyl-4-carboxylate hydrochloride
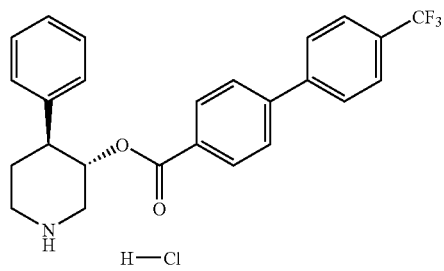
(+/−)-(3S,4S)-4-phenylpiperidin-3-yl 4'-(trifluoromethyl)-1,1'-biphenyl-4-carboxylate hydrochloride
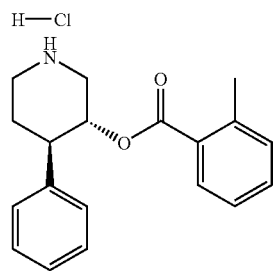
(+/−)-(3R,4R)-4-phenylpiperidin-3-yl 2-methylbenzoate hydrochloride -continued
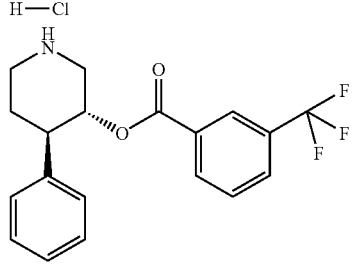
(+/−)-(3R,4R)-4-phenylpiperidin-3-yl 3-(trifluoromethyl)benzoate hydrochloride
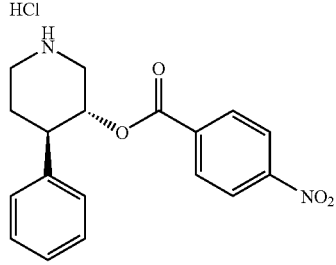
(+/−)-(3R,4R)-4-phenylpiperidin-3-yl 4-nitrobenzoate hydrochloride
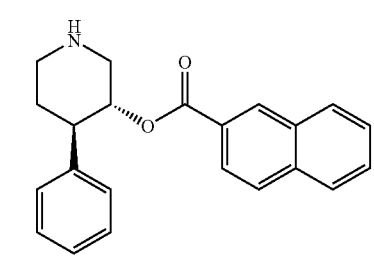
(+/−)-(3R,4R)-4-phenylpiperidin-3-yl 2-naphthoate hydrochloride
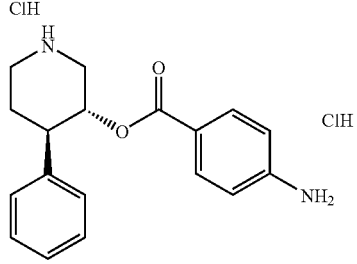
(+/−)-(3R,4R)-4-phenylpiperidin-3-yl 4-aminobenzoate dihydrochloride
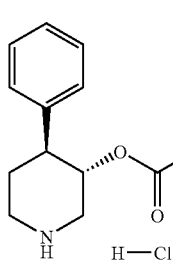
(+/−)-(3S,4S)-4-phenylpiperidin-3-yl 4'-(methylthio)-1,1'-biphenyl-4-carboxylate hydrochloride

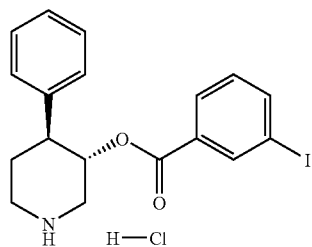
(+/−)-(3S,4S)-4-phenylpiperidin-3-yl 3-iodobenzoate hydrochloride
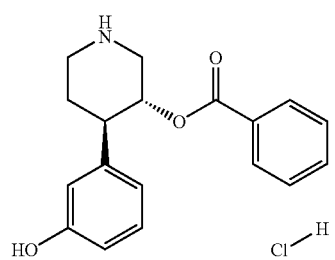
(+/−)-(3R,4R)-4-(3-hydroxyphenyl)piperidin-3-yl benzoate hydrochloride
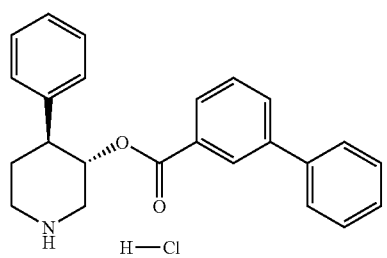
(+/−)-(3S,4S)-4-phenylpiperidin-3-yl 1,1'-biphenyl-3-carboxylate hydrochloride
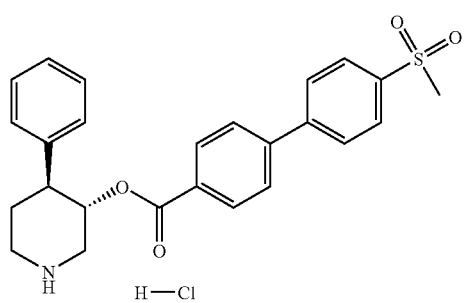
(+/−)-(3S,4S)-4-phenylpiperidin-3-yl 4'-(methylsulfonyl)-1,1'-biphenyl-4-carboxylate hydrochloride
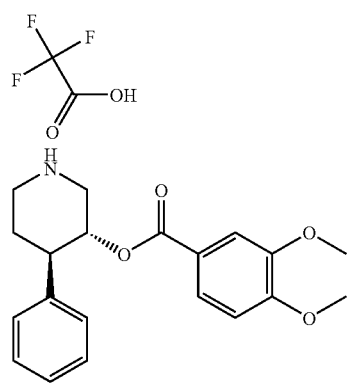
(+/−)-(3R,4R)-4-phenylpiperidin-3-yl 3,4-dimethoxybenzoate trifluoroacetate -continued

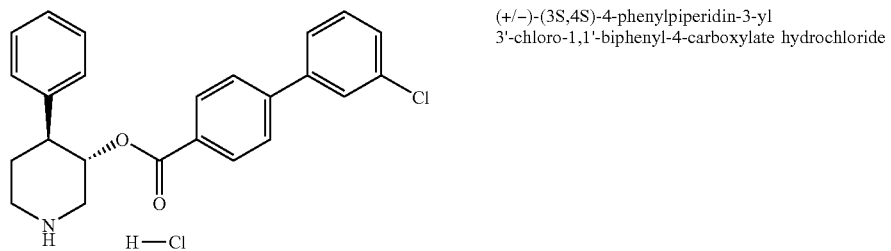 (+/−)-(3S,4S)-4-phenylpiperidin-3-yl 3'-chloro-1,1'-biphenyl-4-carboxylate hydrochloride

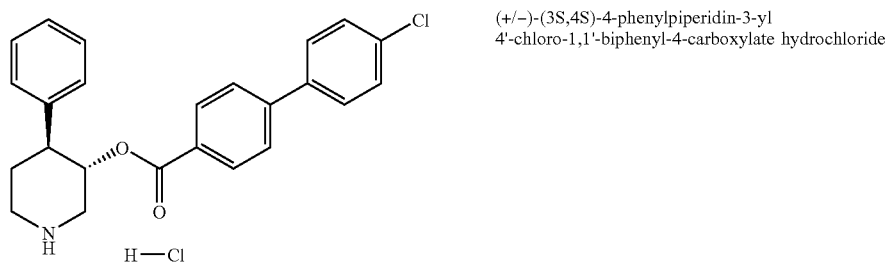 (+/−)-(3S,4S)-4-phenylpiperidin-3-yl 4'-chloro-1,1'-biphenyl-4-carboxylate hydrochloride

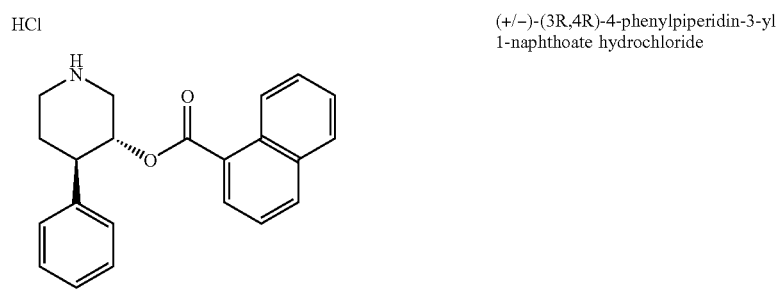 (+/−)-(3R,4R)-4-phenylpiperidin-3-yl 1-naphthoate hydrochloride

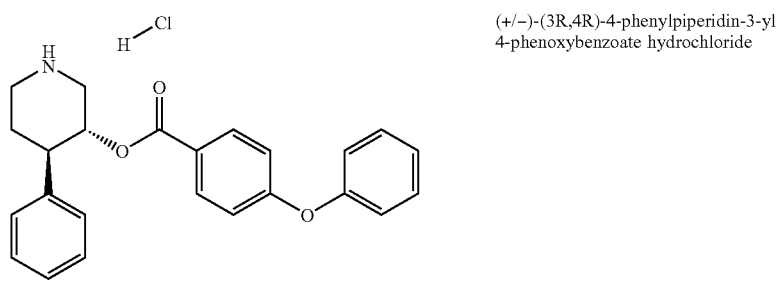 (+/−)-(3R,4R)-4-phenylpiperidin-3-yl 4-phenoxybenzoate hydrochloride

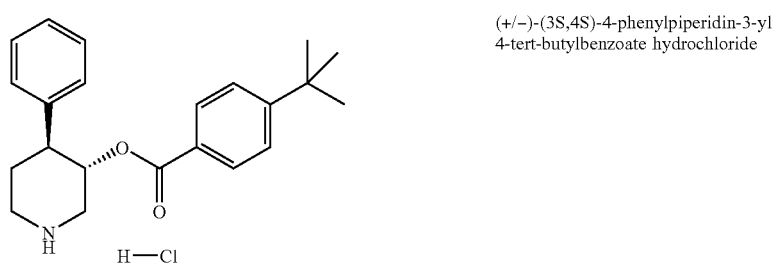 (+/−)-(3S,4S)-4-phenylpiperidin-3-yl 4-tert-butylbenzoate hydrochloride

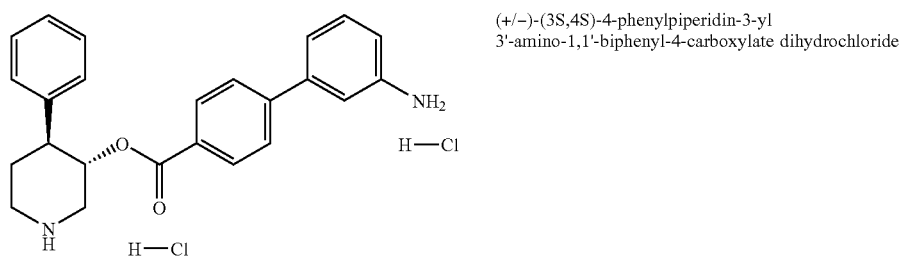 (+/−)-(3S,4S)-4-phenylpiperidin-3-yl 3'-amino-1,1'-biphenyl-4-carboxylate dihydrochloride

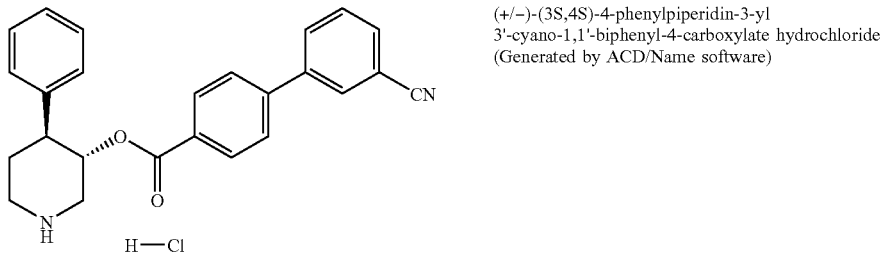

(+/−)-(3S,4S)-4-phenylpiperidin-3-yl 3'-cyano-1,1'-biphenyl-4-carboxylate hydrochloride (Generated by ACD/Name software)

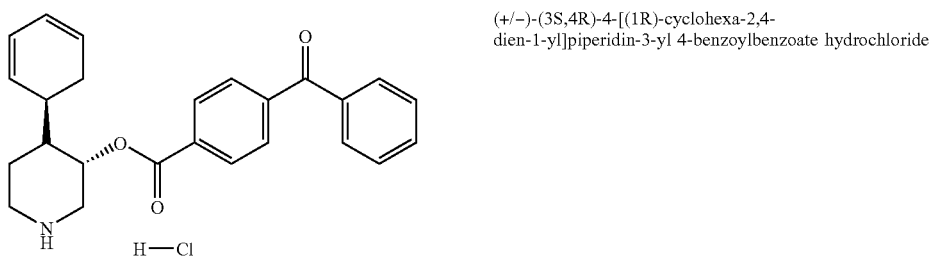

(+/−)-(3S,4R)-4-[(1R)-cyclohexa-2,4-dien-1-yl]piperidin-3-yl 4-benzoylbenzoate hydrochloride

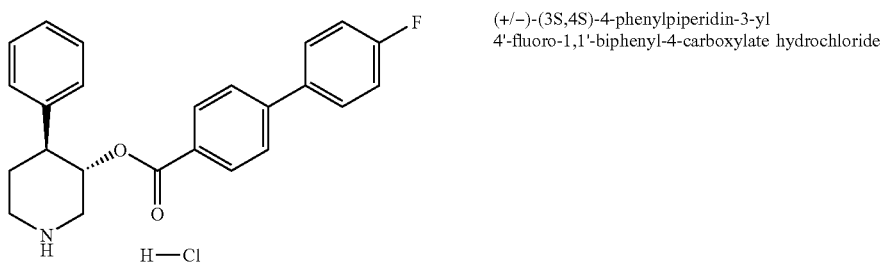

(+/−)-(3S,4S)-4-phenylpiperidin-3-yl 4'-fluoro-1,1'-biphenyl-4-carboxylate hydrochloride

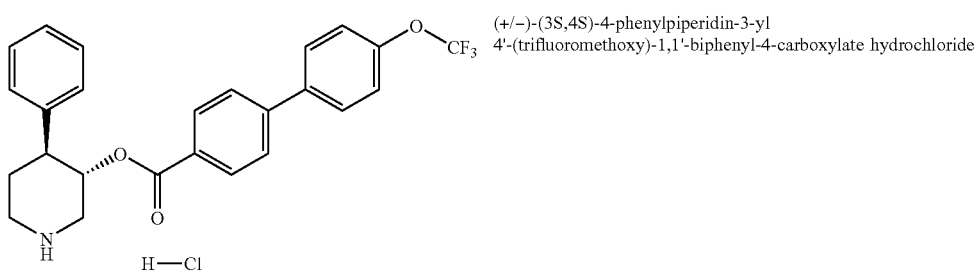

(+/−)-(3S,4S)-4-phenylpiperidin-3-yl 4'-(trifluoromethoxy)-1,1'-biphenyl-4-carboxylate hydrochloride

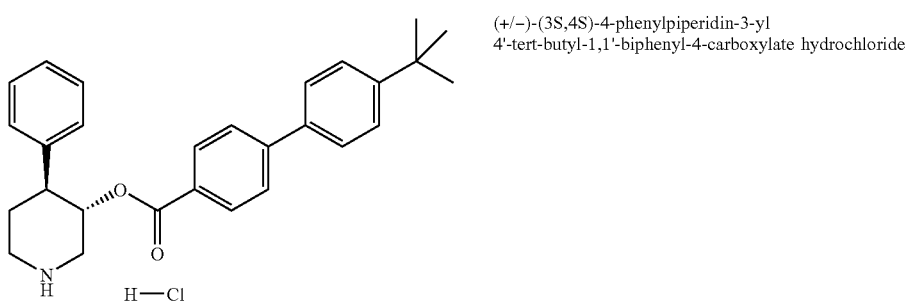

(+/−)-(3S,4S)-4-phenylpiperidin-3-yl 4'-tert-butyl-1,1'-biphenyl-4-carboxylate hydrochloride -continued

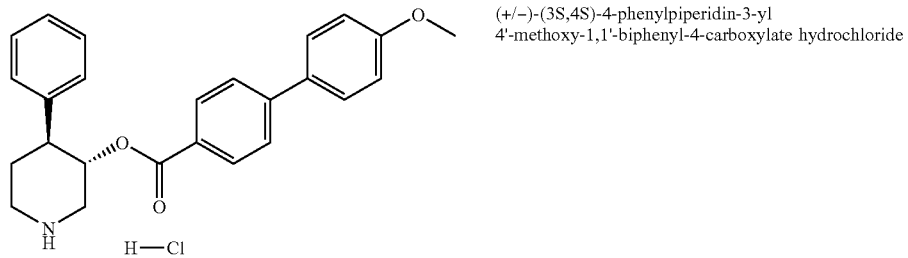

(+/−)-(3S,4S)-4-phenylpiperidin-3-yl 4'-methoxy-1,1'-biphenyl-4-carboxylate hydrochloride or

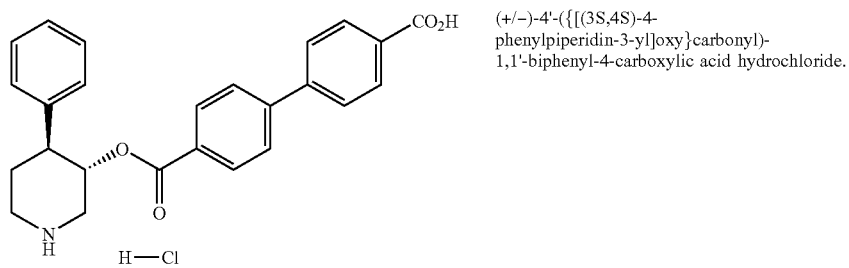

(+/−)-4'-({[(3S,4S)-4-phenylpiperidin-3-yl]oxy}carbonyl)-1,1'-biphenyl-4-carboxylic acid hydrochloride.

6. A compound according to claim 1, having the formula:

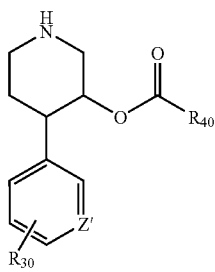

or a pharmaceutically acceptable salt thereof wherein Z' is CH;

wherein $R_{30}$ is absent, —OH, or halo;

wherein $R_{40}$ is aryl, substituted aryl, phenyl or substituted phenyl.

7. A compound according to claim 6, wherein $R_{30}$ is absent, —OH, or Cl, Br, I or F.

8. A compound according to claim 7, wherein $R_{40}$ is selected from the group consisting essentially of -Ph-Ph-CO$_2$H, -Ph-Ph-OCH$_3$, -Ph-Ph-C(CH$_3$)$_3$, -Ph-Ph-OCF$_3$, -Ph-Ph-F, -Ph-C(=O)-Ph, -Ph-Ph-CN, -Ph-Ph-NH$_2$, -Ph-C(CH$_3$)$_3$, Ph-O-Ph, naphthalene, -Ph-Ph-Cl, -Ph-(OCH$_3$)$_2$, Ph-Ph-S(=O)$_2$CH$_3$,-Ph-Ph, Ph, Ph-I, -Ph-Ph-S—CH$_3$, Ph-NH$_2$, -Ph-NO$_2$, -Ph-CF$_3$, -Ph-CH$_3$, -Ph-Ph-CF$_3$, -Ph-Ph-(OCH$_3$)$_2$, -Ph-OCH$_3$, -Ph-CN, and -Ph-OCF$_3$.

9. A compound according to claim 8, wherein a single substituent attached to a Ph-ring is in the meta position.

10. A composition comprising a compound of claim 1 or a pharmaceutically acceptable salt thereof; and a pharmaceutically acceptable diluent, carrier, or excipient.

* * * * *